US009532997B2

(12) United States Patent
Katajisto et al.

(10) Patent No.: US 9,532,997 B2
(45) Date of Patent: Jan. 3, 2017

(54) COMPOSITIONS AND METHODS FOR PROMOTING INTESTINAL STEM CELL FUNCTION

(71) Applicant: Whitehead Institute for Biomedical Research, Cambridge, MA (US)

(72) Inventors: Pekka Katajisto, Cambridge, MA (US); Michael Pacold, Boston, MA (US); David M. Sabatini, Cambridge, MA (US); Omer Yilmaz, Ann Arbor, MI (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 0 days.

(21) Appl. No.: 14/390,731

(22) PCT Filed: Apr. 3, 2013

(86) PCT No.: PCT/US2013/035145
§ 371 (c)(1),
(2) Date: Oct. 3, 2014

(87) PCT Pub. No.: WO2013/152120
PCT Pub. Date: Oct. 10, 2013

(65) Prior Publication Data
US 2015/0258124 A1 Sep. 17, 2015

Related U.S. Application Data

(60) Provisional application No. 61/619,864, filed on Apr. 3, 2012.

(51) Int. Cl.
| | | |
|---|---|---|
| A61K 31/675 | (2006.01) | |
| A61K 45/06 | (2006.01) | |
| A61K 31/436 | (2006.01) | |
| A61K 31/7076 | (2006.01) | |
| A61K 31/7088 | (2006.01) | |
| A61K 38/46 | (2006.01) | |
| A61K 31/713 | (2006.01) | |

(52) U.S. Cl.
CPC ........... *A61K 31/675* (2013.01); *A61K 31/436* (2013.01); *A61K 31/7076* (2013.01); *A61K 31/7088* (2013.01); *A61K 31/713* (2013.01); *A61K 38/46* (2013.01); *A61K 45/06* (2013.01); *C12Y 301/00* (2013.01)

(58) Field of Classification Search
CPC .................................................. A61K 31/675

USPC .......................................................... 514/81
See application file for complete search history.

(56) References Cited

FOREIGN PATENT DOCUMENTS

| | | |
|---|---|---|
| WO | WO 2009/046436 A1 | 4/2009 |
| WO | WO 2009/111648 A1 | 9/2009 |

OTHER PUBLICATIONS

Yilmaz et al. Nature, 486(28, 2012.*
Harris et al. Cell Metabolism 16, Jul. 3, 2012, p. 6-8.*
Kim et al. Current Biology vol. 22 No. 14, R579-R580Jul. 24, 2012.*
Blagosklonny, "Raoamysin-induced glucose intolerance. Hunger or starvation diabetes," *Cell Cycle*, 10(24), 4217-4224; 2011.
Myers et al., "Rapamycin-induced tumor vasculature remodeling in rhabdomyosarcoma xenografts increases the effectiveness of adjuvant ionizing radiation," *Journal of Pediatric Surgery*, 41(1), 183-189; 2012.
Nuhrenberg, T.G., et al., "Rapamycin attenuates vascular wall inflammation and progenitor cell promoters after angioplasty," *The Journal of the Federation of American Societies for Experimental Biology*, 19(2), 246-248; 2005.
Podesta et al., "Concentrative uptake of cyclic ADP-ribose generated by BST-1+ stroma stimulates proliferation of human hematopoietic progenitors," *The Journal of Biological Chemistry*, 280(7), 5343-5349; 2005.
Sato et al., "Paneth cells constitute the niche for Lgr5 stem cells in intestinal crypts," *Nature*, 469(733), 415-418; 2011.
Zhuang et al., "Induction of autophagy promotes differentiation of glioma-initiating cells and their radiosensitivity," *International Journal of Cancer*, 129(11), 2720-2731; 2011.
Zoncu et al., mTOR: From growth signal integration to cancer, diabetes and ageing, *Nature Reviews. Molecular Cell Biology*, 12(1), 21-35; 2011.
International Search Report for International Application PCT/US2013/035145, dated Oct. 18, 2013.

* cited by examiner

*Primary Examiner* — Nizal Chandrakumar
(74) *Attorney, Agent, or Firm* — Lisa M. Warren, Esq.; Morse, Barnes-Brown & Pendleton, P.C.

(57) ABSTRACT

Disclosed herein are novel methods and compositions useful for promoting intestinal stem cell function. The methods and compositions are particularly useful for stimulating the proliferation of and/or self-renewal of intestinal stem cells, as well as for minimizing, preventing, or ameliorating cellular damage resulting from incidental or accidental exposure to radiation (e.g., cancer radiation therapy).

7 Claims, 30 Drawing Sheets

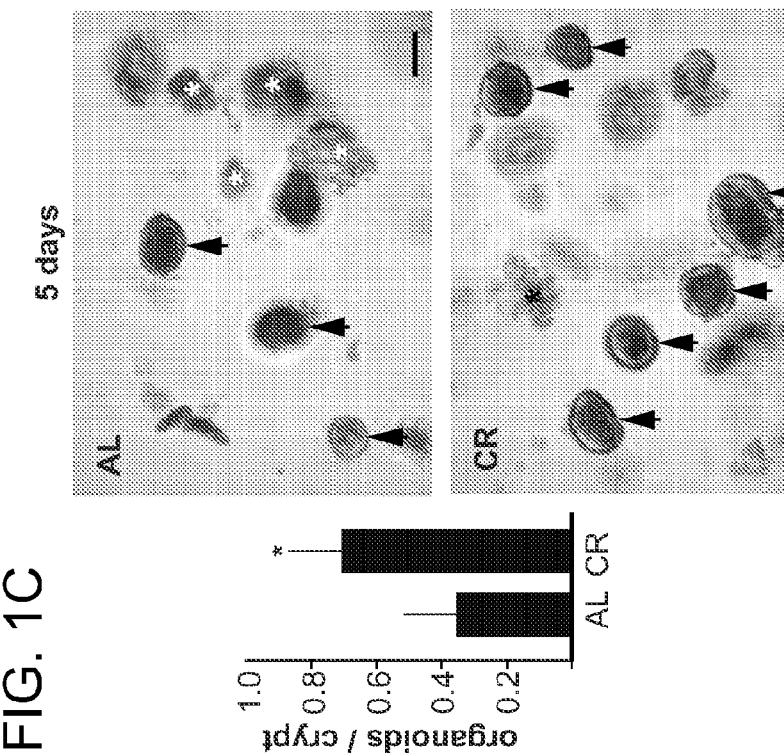
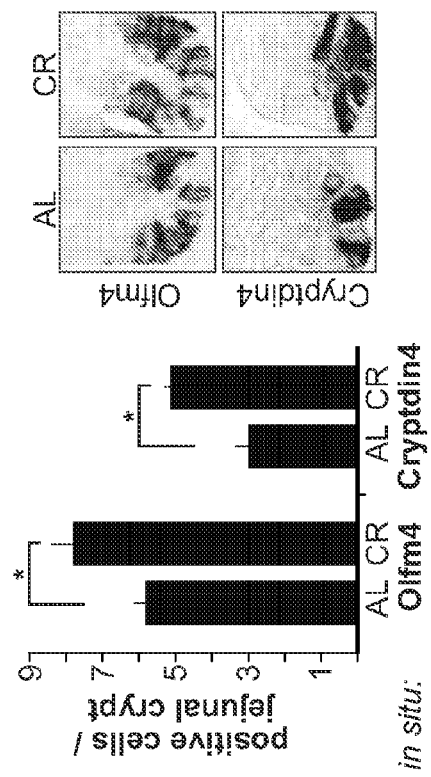
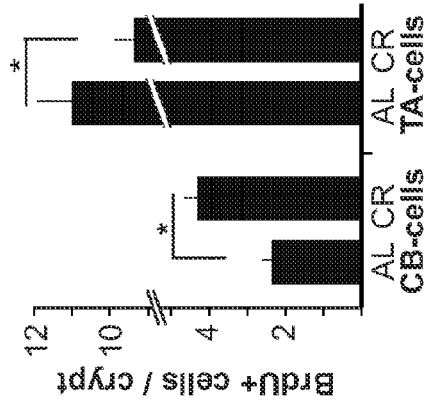
FIG. 1A
FIG. 1B
FIG. 1C

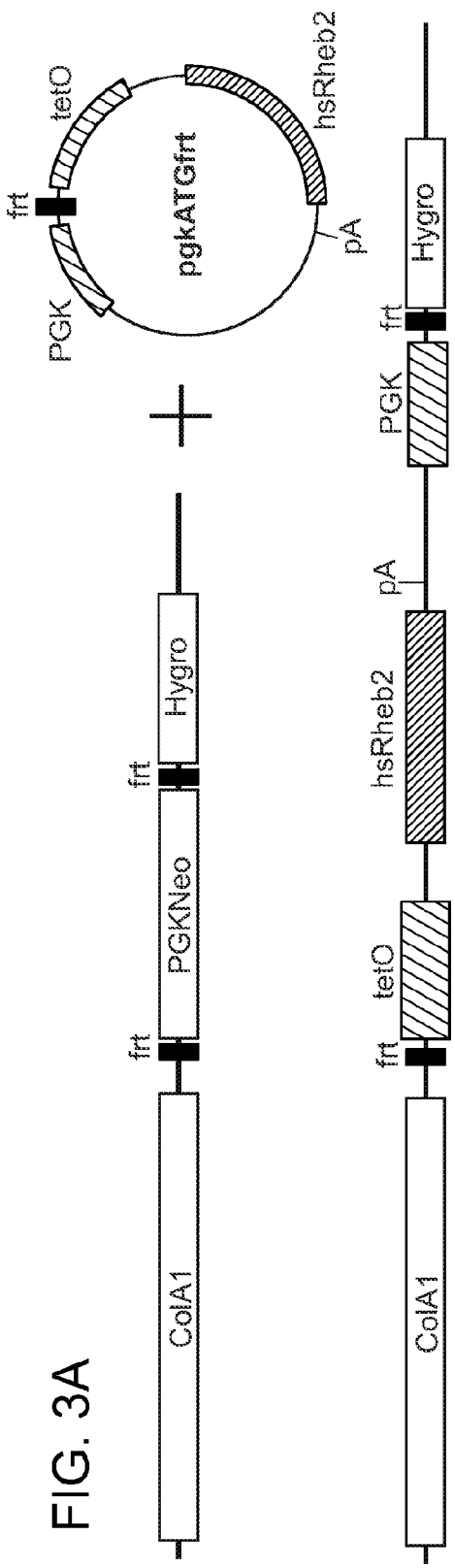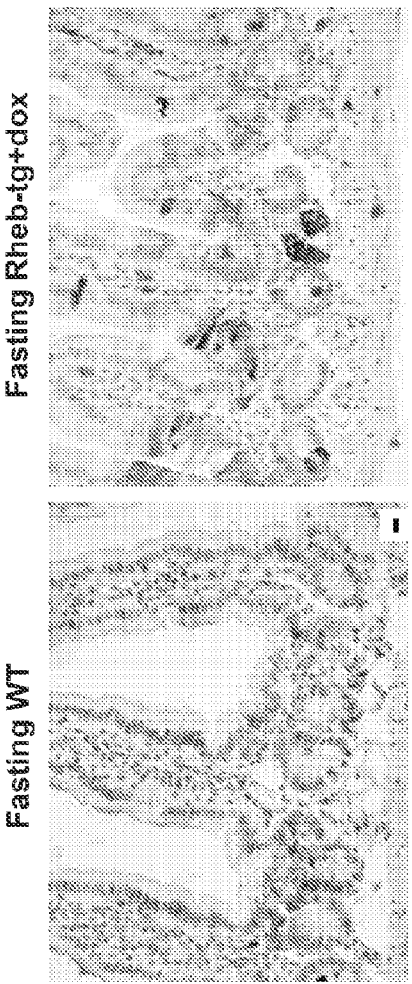
FIG. 3A
FIG. 3B
FIG. 3C

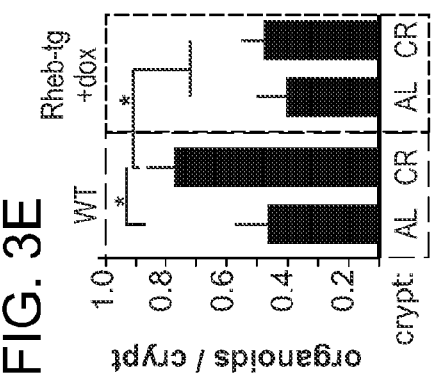
FIG. 3E
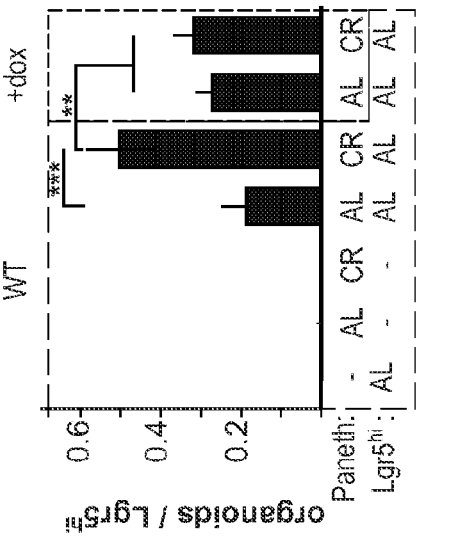
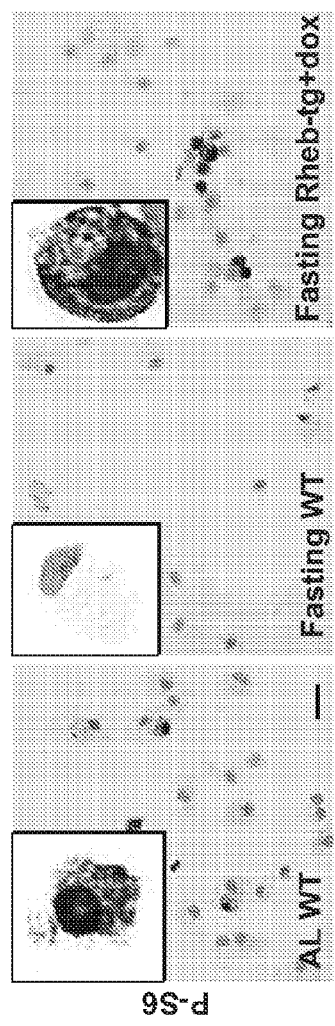
FIG. 3D
FIG. 3F

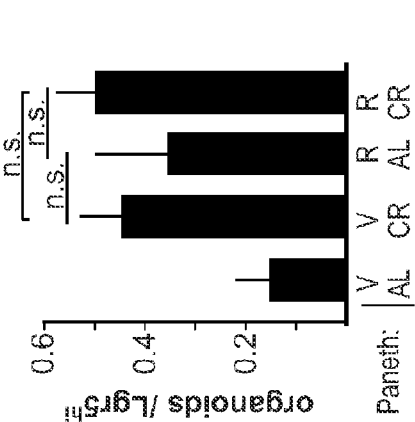
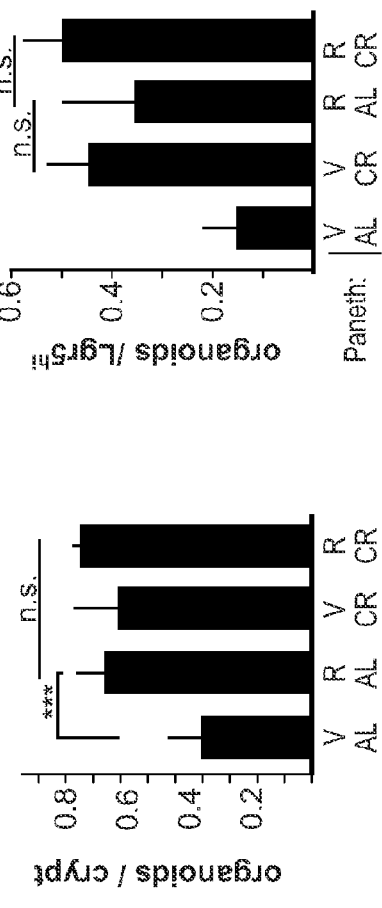
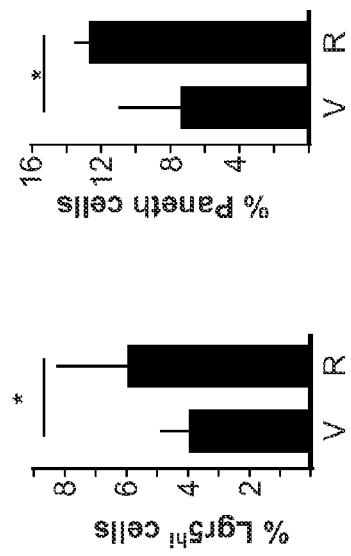
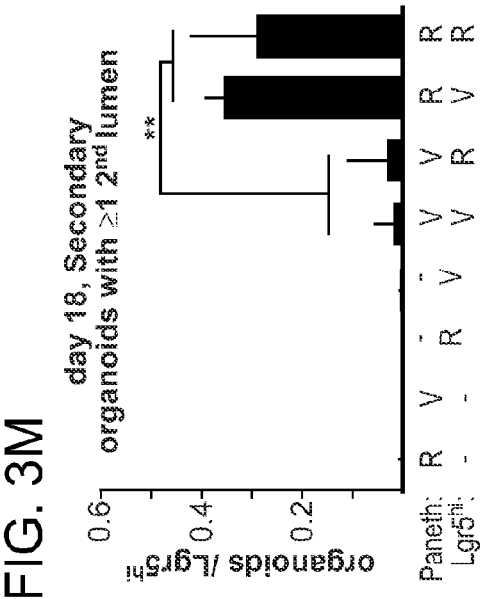
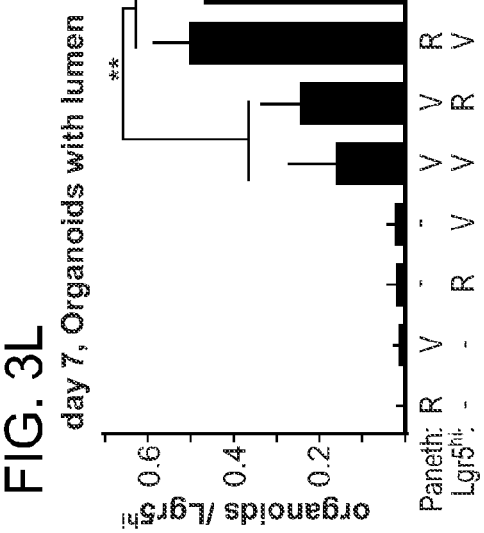
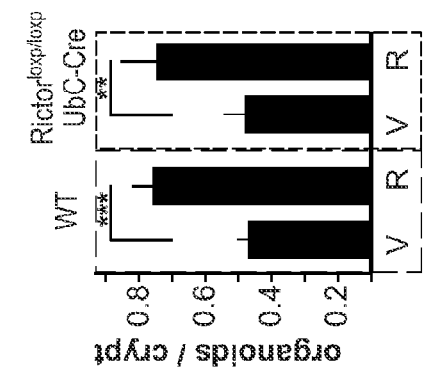
FIG. 3G  FIG. 3H  FIG. 3I  FIG. 3J  FIG. 3K  FIG. 3L  FIG. 3M

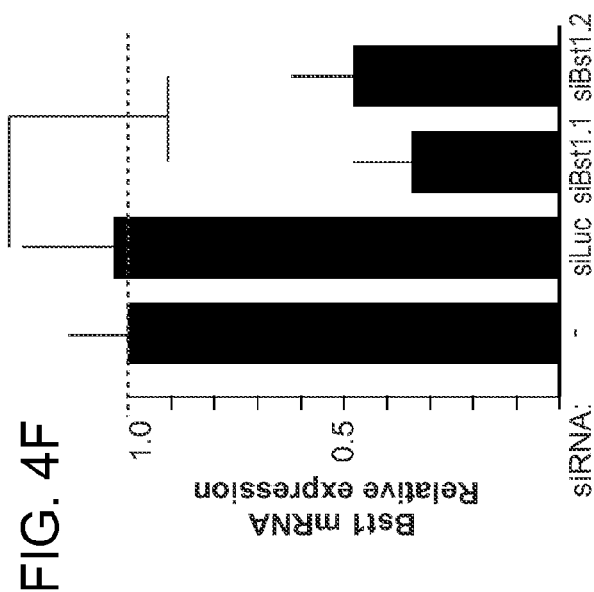
FIG. 4F
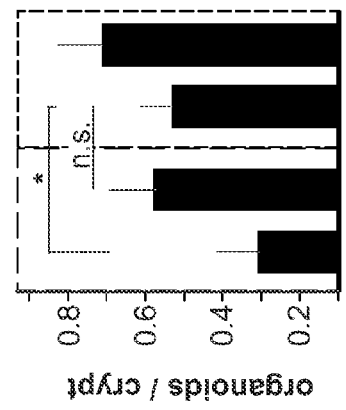
FIG. 4E
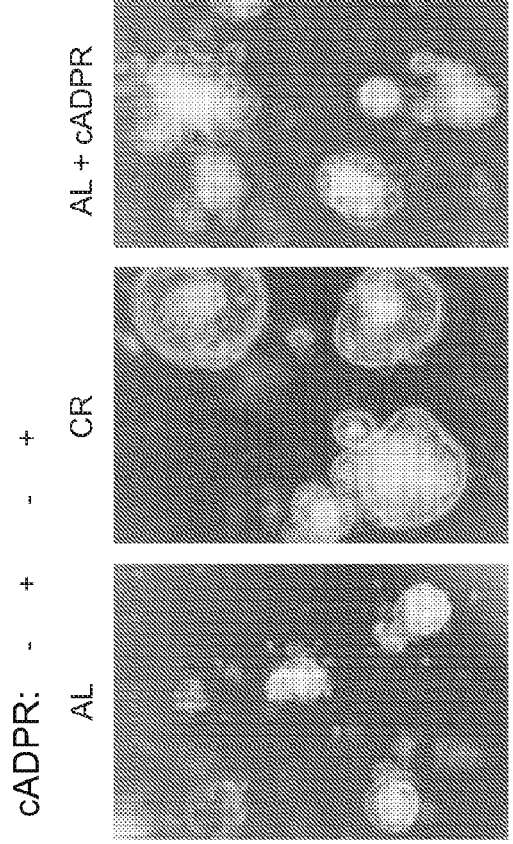

COMPOSITIONS AND METHODS FOR PROMOTING INTESTINAL STEM CELL FUNCTION

CROSS-REFERENCE TO RELATED APPLICATION

This application is a national stage filing under 35 U.S.C. 371 of International Application No. PCT/US2013/035145, filed Apr. 3, 2013, which claims the benefit of U.S. Provisional Application No. 61/619,864, filed Apr. 3, 2012. The entire teachings of the above application(s) are incorporated herein by reference. International Application PCT/US2013/035145 was published under PCT Article 21(2) in English.

GOVERNMENT SUPPORT

This invention was made with government support under NIH-5R01CA103866 and NIH-5RO1CA129105 awarded by the National Institutes of Health. The government has certain rights in the invention.

BACKGROUND OF THE INVENTION

Adult stem cells maintain tissues for the life of an organism by achieving equilibrium between self-renewal and differentiation. These stem cells often require cues from their microenvironment or "niche" for their maintenance and function. In the mammalian intestine, for example, most intestinal stem cells (ISCs) reside at the bottom of the crypts and are adjacent to Paneth cells, which constitute a key component of the stem cell niche.

Intestinal atrophy or damage affects a significant portion of hospitalized patients in the US, including those suffering from inflammatory bowel disease, vascular disease, cancer, infection or malnourishment, as well as those exposed to ionizing radiation. Accordingly, there remains a need for therapies capable of modulating the processes of intestinal cell proliferation and remodeling.

SUMMARY OF THE INVENTION

The present invention relates in some aspects to novel methods, agents, and compositions useful for promoting intestinal stem cell function. Certain of the methods, agents, and compositions are particularly useful for stimulating the proliferation and/or self-renewal of intestinal stem cells in mammalian intestinal tissue, for example, by contacting a population of Paneth cells or Paneth-like cells in the mammalian intestinal tissue with an effective amount of a calorie restriction mimetic, which may be useful for ameliorating afflictions characterized by intestinal atrophy, as well as for preventing or ameliorating harmful effects of ionizing radiation, particularly during radiation cancer therapy or upon accidental or incidental exposure to ionizing radiation.

In some aspects, methods of stimulating the proliferation and/or self-renewal of one or more intestinal stem cells in mammalian intestinal tissue are disclosed, such method comprising contacting a population of Paneth cells or Paneth-like cells in the mammalian intestinal tissue with an effective amount of a calorie restriction mimetic.

In some embodiments the calorie restriction mimetic comprises an agent that inhibits the level and/or activity of mTORC1. In some embodiments the agent attenuates intrinsic kinase activity of mTOR. In some embodiments the agent interferes with interaction between mTOR and a phosphorylation target of mTOR. In some embodiments the agent prevents mTOR from phosphorylating serine and threonine residues. In some embodiments the agent is selected from the group consisting of an antisense nucleic acid, an oligopeptide, an aptamer, a ribozyme, a small molecule, an intrabody, an antibody or a fragment thereof. In some embodiments the agent comprises sirolimus or a derivative or analog thereof. In some embodiments the agent is selected from the group consisting of temsirolimus, everolimus, and ridaforolimus.

In some embodiments the calorie restriction mimetic comprises an agent that increases the level and/or activity of bone stromal antigen 1 (Bst-1) or a product of Bst-1. In some embodiments the agent stimulates intracellular release of $Ca^{2+}$. In some embodiments the agent induces the ryanodine receptor to release $Ca^{2+}$ into the cytosol. In some embodiments the product of Bst-1 comprises cyclic ADP ribose. In some embodiments the agent comprises cluster of differentiation 38 (CD38) protein, a functional variant of CD38, fragment of CD38, a nucleic acid having a sequence that encodes a functional CD38 protein or a functional fragment thereof, or a CD38 mimetic. In some embodiments the agent is a nucleic acid sequence that encodes Bst-1, a functional fragment of a nucleic acid sequence that encodes Bst-1, a sequence homologous to a nucleic acid sequence that encodes Bst-1, a Bst-1 protein or a variant thereof, a functional domain or fragment of Bst-1 protein, a functional homolog of Bst-1, and a fusion protein comprising Bst-1.

In some aspects, methods of treating afflictions characterized by intestinal atrophy are disclosed, such methods comprising stimulating the proliferation and/or self-renewal of intestinal stem cells in the patient. In some embodiments stimulating the intestinal stem cells in the patient comprises administering to the patient an effective amount of a calorie restriction mimetic.

In some embodiments the calorie restriction mimetic comprises an agent that inhibits the level and/or activity of mTORC1 in the patient. In some embodiments the agent comprises sirolimus or a derivative or analog thereof. In some embodiments the calorie restriction mimetic comprises an appetite suppressant optionally combined with a nutritional supplement. In some embodiments the calorie restriction mimetic comprises an agent that increases the level and/or activity of Bst-1 or a product of Bst-1. In some embodiments the product of Bst-1 comprises cyclic ADP ribose (cADPR). In some embodiments the affliction is selected from the group consisting of an inflammatory disease, an autoimmune disease, vascular disease, cancer, infection, short bowel syndrome, drug-induced or toxin-induced intestinal injury, an affliction treatable by parenteral nutrition (PN) or life-long parenteral nutrition, an affliction treatable by parenteral nutrition, and exposure to ionizing radiation.

In some aspects, radioprotective agents are disclosed, such agents comprising agents that inhibit the level and/or activity of mTORC1 or increase the level and/or activity of Bst-1, cADPR, or CD38. In some embodiments the agent comprises sirolimus or derivative or analog thereof. In some embodiments the derivative is selected from the group consisting of temsirolimus, everolimus, and ridaforolimus. In some embodiments the radioprotective agent prevents or ameliorates the harmful effects of ionizing radiation on mammalian cells. In some embodiments the radioprotective agent prevents or ameliorates the harmful effects of ionizing radiation on gastrointestinal cells. In some embodiments the radioprotective agent stimulates the proliferation and/or self-renewal of intestinal stem cells. In some embodiments the radioprotective agent preserves the normal morphology of Paneth cells. In some embodiments the agent stimulates the proliferation of Paneth cells. In some embodiments the radioprotective agent inhibits the level and/or activity of mTORC1 in mammalian Paneth cells.

In some aspects, compositions are disclosed, such compositions comprising radioprotective agents of the present invention and a pharmaceutically acceptable carrier, diluent, or excipient. In some embodiments the composition is administered in combination with a therapy selected from the group consisting of chemotherapy, radiotherapy, proton therapy, surgery, and combinations thereof. In some embodiments the compositions further comprise a chemotherapeutic agent. In some embodiments the compositions further comprise a radiotherapeutic agent. In some embodiments the compositions further comprise an insulin inhibitor. In some embodiments the compositions further comprise an appetite suppressant and a vitamin supplement. In some embodiments the compositions further comprise an antioxidant. In some embodiments the compositions are formulated for administration as an enema.

In some aspects, methods of minimizing the risk of exposure to ionizing radiation sources are disclosed, such methods comprising administering to an individual an effective amount of a calorie restriction mimetic. In some embodiments the calorie restriction mimetic comprises an agent that inhibits the level and/or activity of mTORC1. In some embodiments the agent is sirolimus or a derivative or analog thereof. In some embodiments the calorie restriction mimetic comprises an agent that increases the level and/or activity of Bst-1 or a product of Bst-1. In some embodiments the agent comprises CD38 or an analog of CD38. In some embodiments the agent comprises Bst-1 protein or a nucleic acid sequence encoding the Bst-1 protein. In some embodiments the product of Bst-1 comprises cADPR. In some embodiments the ionizing radiation source is a source of accidental or incidental ionizing radiation. In some embodiments the ionizing radiation source is a nuclear power plant. In some embodiments the ionizing radiation source is a nuclear weapon. In some embodiments the ionizing radiation source is space or cosmic radiation. In some embodiments the individual is an individual that is being administered, or about to be administered, radiotherapy.

In some aspects, methods of treating an individual exposed to harmful ionizing radiation are disclosed, such methods comprising administering to the individual an effective amount of a calorie restriction mimetic. In some embodiments the calorie restriction mimetic is an agent that inhibits the level and/or activity of mTORC1. In some embodiments the calorie restriction mimetic is an agent that increases the level and/or activity of Bst-1 or a product of Bst-1. In some embodiments the calorie restriction mimetic is cADPR or a derivative or analog thereof. In some embodiments the calorie restriction mimetic is CD38 or a derivative or analog thereof.

In some aspects methods of increasing tolerance to ionizing radiation in an individual are disclosed, such methods comprising administering to the individual an effective amount of a calorie restriction mimetic, wherein the calorie restriction mimetic increases the threshold dose of lethal ionizing radiation to above 8 Gy. In some embodiments the threshold dose of lethal ionizing radiation is increased to about 15 Gy.

In some aspects, methods of treating cancer are disclosed, such methods comprising administering an effective amount of ionizing radiation to a patient in need thereof, and administering to the patient an effective amount of a calorie restriction mimetic. In some embodiments the calorie restriction mimetic comprises an agent that inhibits the level and/or activity of mTORC1. In some embodiments the agent comprises sirolimus or a derivative thereof or analog thereof. In some embodiments calorie restriction mimetic comprises an agent that increases the level and/or activity of Bst-1 or a product of Bst-1. In some embodiments the product of Bst-1 comprises cADPR. In some embodiments the calorie restriction mimetic comprises CD38. In some embodiments the calorie restriction mimetic is administered to the patient prior to administering the ionizing radiation to the patient. In some embodiments the calorie restriction mimetic is co-administered to the patient with the ionizing radiation. In some embodiments the calorie restriction mimetic is administered to the patient after administering the ionizing radiation to the patient.

In some aspects, methods for expanding and activating a population of intestinal stem cells are disclosed, such methods comprising contacting a population of Paneth cells or Paneth-like cells, in cellular communication with the intestinal stem cells, with an effective amount of an agent that inhibits the level and/or activity of mTORC1. In some embodiments the agent comprises sirolimus or a derivative or analog thereof. In some embodiments the method is performed in vitro. In some embodiments the method is performed ex vivo.

The practice of the present invention will typically employ, unless otherwise indicated, conventional techniques of cell biology, cell culture, molecular biology, transgenic biology, microbiology, recombinant nucleic acid (e.g., DNA) technology, immunology, and RNA interference (RNAi) which are within the skill of the art. Non-limiting descriptions of certain of these techniques are found in the following publications: Ausubel, F., et al., (eds.), *Current Protocols in Molecular Biology, Current Protocols in Immunology, Current Protocols in Protein Science*, and *Current Protocols in Cell Biology*, all John Wiley & Sons, N.Y., edition as of December 2008; Sambrook, Russell, and Sambrook, *Molecular Cloning: A Laboratory Manual, 3$^{rd}$ ed.*, Cold Spring Harbor Laboratory Press, Cold Spring Harbor, 2001; Harlow, E. and Lane, D., Antibodies—A Laboratory Manual, Cold Spring Harbor Laboratory Press, Cold Spring Harbor, 1988; Freshney, R. I., "Culture of Animal Cells, A Manual of Basic Technique", 5th ed., John Wiley & Sons, Hoboken, N.J., 2005. Non-limiting information regarding therapeutic agents and human diseases is found in Goodman and Gilman's The Pharmacological Basis of Therapeutics, 11th Ed., McGraw Hill, 2005, Katzung, B. (ed.) Basic and Clinical Pharmacology, McGraw-Hill/Appleton & Lange; 10$^{th}$ ed. (2006) or 11th edition (July 2009). Non-limiting information regarding genes and genetic disorders is found in McKusick, V. A.: Mendelian Inheritance in Man. A Catalog of Human Genes and Genetic Disorders. Baltimore: Johns Hopkins University Press, 1998 (12th edition) or the more recent online database: Online Mendelian Inheritance in Man, OMIM™. McKusick-Nathans Institute of Genetic Medicine, Johns Hopkins University (Baltimore, Md.) and National Center for Biotechnology Information, National Library of Medicine (Bethesda, Md.), as of May 1, 2010, World Wide Web URL: http://www.ncbi.nlm.nih.gov/omim/ and in Online Mendelian Inheritance in Animals (OMIA), a database of genes, inherited disorders and traits in animal species (other than human and mouse), at http://omia.angis.org.au/contact.shtml. All patents, patent applications, and other publications (e.g., scientific articles, books, websites, and databases) mentioned herein are incorporated by reference in their entirety. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

BRIEF DESCRIPTION OF THE DRAWINGS

The patent or application file contains at least one drawing executed in color. Copies of this patent or patent application publication with color drawings will be provided by the Office upon request and payment of the necessary fee.

FIGS. 1a-1m. Caloric restriction extrinsically augments the capacity of Paneth cells to boost intestinal stem cell (ISC) function. Calorie restriction (CR) increased the frequency of intestinal stem cells and of their Paneth cell niche (a, f) compared to ad libitum (AL) fed mice. (a) Increase of Olfactomedin-4+ (Olfm4) intestinal stem cells and Cryptdin4+ Paneth cells in CR mice (in situ hybridization, proximal jejunum, n=3). (b) While crypt base columnar cells (CB-cells, which are adjacent to Paneth cells at the bottom of crypts) of CR mice showed a 2-fold increase in BrdU incorporation after 4 hours (n=3), more differentiated transient amplifying cells (TA-cells) demonstrated a reduction in BrdU positivity (11.0±0.9 vs. 9.4±0.5). (c) Crypts isolated from CR mice were nearly 2-fold more capable of forming organoid bodies in culture compared to those from AL controls (n=8). Representative AL and CR-derived organoid bodies 5 days after plating (red arrowhead marks organoids and yellow asterisk indicates aborted, non-functional crypts; scale bar 50 µm). Clonogenicity (colony-forming efficiency) was calculated by plating 50 to 400 crypts and assessing organoid formation 3 to 7 days after initiation of cultures. (d, e) CR increased the number of surviving (d) and proliferating (e, Ki67+) clonogenic crypts after gamma irradiation induced damage in vivo. AL and CR mice were exposed to 15 Gy of gamma irradiation and sacrificed after 72 hours. The number of surviving crypts per length of the intestine was enumerated from H&E-stained sections. (f) Schematic demonstrating dark green Lgr5$^{hi}$ cells that are adjacent to red Paneth cells at the base of the crypt and light green EGFP$^{low}$ progenitors located higher up in the crypt. As determined by flow cytometry, CR revealed a 1.5-fold increase in ISCs (dark green box, Lgr5-EGFPhiEpcam+CD24$^{low}$/-CD31-Ter119-CD45-) and in Paneth cells (red box, CD24$^{hi}$SideScatter$^{hi}$Lgr5-EGFP-Epcam-CD31-Ter119-D45-) compared to those from AL mice (n=40-50). However, CR reduced the frequency of more differentiated intestinal progenitor cells (light green box, GFP$^{low}$Epcam+CD24$^{low}$/-CD31-Ter119-CD45-) by 20% compared to those from AL controls. Dead cells were excluded from the analysis with the viability dye 7-AAD. (g) A schematic illustrating the mixing of ISCs (dark green) with Paneth cells (red) in matrigel and subsequent organoid body formation. (h) Organoid formation per Lgr5hi ISCs cocultured with Paneth cells from CR mice was significantly increased compared to Paneth cells from AL mice (n=5). In contrast, CR had no direct effect on ISC function as CR or AL ISCs behaved similarly in culture. Representative primary organoid bodies derived from AL and CR Paneth cells at day 7. (i) Dissociated organoid bodies derived from CR Paneth cells gave rise to larger, complex secondary organoid bodies with more than one lumen compared to those derived from AL Paneth cells at day 18 (n=5). (j) Sorted ISC-Paneth cell doublets plated at clonal density (50-100 doublets per 30 ul droplet of matrigel) demonstrated that doublets from CR mice were nearly 3-fold more clonogenic than those from AL controls (n=3). (k) EGFP$^{low}$ intestinal progenitors, unlike ISCs and irrespective of whether combined with AL or CR Paneth cells, harbored little organoid body forming potential (n=4). (l) Subcloning of individual organoid bodies derived from CR Paneth cells gave rise to on average 3-fold more secondary organoid bodies (9 organoids from 3 independent mice per condition, n=9, shades of grey or blue denote separate mice). (m) Paneth cells isolated from mice that had been on CR, but were returned to an AL diet for 3 days, also retain an augmented capacity to promote organoid formation. Values are mean±s.d., scale bar 50 µm * indicates p<0.05,  p<0.01, and * p<0.001).

FIGS. 3a-m. mTORC1 signaling in Paneth cells mediates the effects of calorie restriction on ISC function. (a) Schematic illustrating the Rosa26-rtTA/doxycycline (Tet-ON) inducible human Rheb2 gene (Rheb-tg). (b) Administration of doxycycline (dox) in the water induced Rheb2 protein (compare to nonspecific background (B.G.)) and led to the phosphorylation S6 ribosomal protein (P-S6, compare to S6), an mTORC1 reporter, in the liver. (c, d) Immunostains for P-S6 was induced in fasted Rheb-tg mice upon intraperitoneal dox injections and was confirmed in cytospun preparations of sorted Paneth cells. (e, f) Induction of Rheb2 from the start of calorie restriction (CR) abrogated the enhancement in organoid formation per crypt (e) and per Lgr5hi ISC (f) when mixed with CR Paneth cells from induced Rheb-tg+dox mice (n=3-5). Representative images (f) illustrating decreased numbers of organoid bodies with Rheb2 induction in CR Paneth cells. (g, h) Rapamycin administration for 4 weeks increased the frequency of Lgr5$^{hi}$ ISCs (Lgr5-EGFP$^{hi}$Epcam+CD24$^{low}$/-CD31-Ter119-CD45- live cells) (g) and Paneth cells (CD24hiSideScatter$^{hi}$Lgr5-EGFP-Epcam+CD31-Ter119-CD45- live cells) (h) compared to vehicle (V) treated controls as measured by flow cytometry (n=13-14). (i, j) Organoids per intestinal crypts (i) and AL Lgr5hi ISCs (j) isolated from or mixed with Paneth cells from Rapamycin, CR, or CR+R treated mice were increased nearly 2-fold compared to vehicle-treated mice (V, n=3-5). The combination of CR and rapamycin was non-additive in crypt (i) or ISC-Paneth cell coculture experiments (j). (k) Enhancement in organoid formation by rapamycin was independent of mTOR complex 2. Administration of rapamycin 1 to 3 weeks after Rictor-deletion in Rictorfl/flUBC-CreERT2 mice increased crypt clonogenicity to a similar extent as those isolated from rapamycin treated wild-type (WT) mice. (l) Organoid formation of Lgr5hi ISCs combined with Paneth cells from rapamycin-treated mice was significantly increased vs. Paneth cells from vehicle-treated mice (n=3-5). Rapamycin had no direct effect on ISC function, as ISCs from Rapamycin-treated and vehicle-treated mice were similarly clonogenic in culture. (m) Secondary organoid bodies derived from rapamycin-treated Paneth cells were larger and more complex than those from vehicle-treated Paneth cells. Rapamycin was administered in vivo to mice at 4 mg/kg daily for 1 to 4 weeks prior to analysis. * indicates p<0.05 and  p<0.01, * p<0.001. Values are mean±s.d., scale bars 20 µm.

FIGS. 4a-i. Calorie restriction enhances expression of bone stromal antigen 1 (Bst-1) in Paneth cells, whose product cyclic ADP ribose (cADPR) enhances ISC function. CR modulates gene expression in Paneth cells. (a) Transcriptional profiling of Paneth cells from CR and AL treated mice (n=4 and 3 respectively) demonstrated significant changes in expression of 401 genes (p<0.01, fold change>1.2), 57 of which encode for plasma membrane associated or secreted proteins. (b) Validation of the increased transcription of Bst-1 by qRT-PCR. Bst-1 was enhanced by over 5-fold, while genes involved with Wnt/β-catenin pathway were unchanged (n=3). (c, d) Concordant with transcriptional upregulation, Bst-1 protein expression increased in crypts isolated from CR mice and Rapamycin-treated mice by immunoblots (c) and in Paneth cells by immunostains (d). CR and Rapamycin also affected the SDS-PAGE mobility of Bst-1, suggesting CR-modulated processing. (e) Addition of cADPR (50 µM), a product of Bst-1, to the culture media increased the organoid forming potential of AL crypts to an extent similar to those of CR crypts. (f, g) inhibition of Bst-1 by siRNA mediated knock-down (f) abrogated the enhanced potential of CR-derived crypts to form organoids (g). (h) Addition of Dipyridamole (100 nM), an inhibitor of the cADPR nucleoside transporter, reduced the organoid forming capacity of AL and CR-derived crypts to a similar level. (i) A model illustrating how calorie restriction, by attenuating mTORC1 activity in the Paneth cells, modulates intestinal adaptation by non-autonomous regulation of ISC self-renewal. CR increases expression of Bst-1, whose paracrine product cADPR promotes ISC self-renewal.

DETAILED DESCRIPTION OF CERTAIN EMBODIMENTS

Figure 1D:
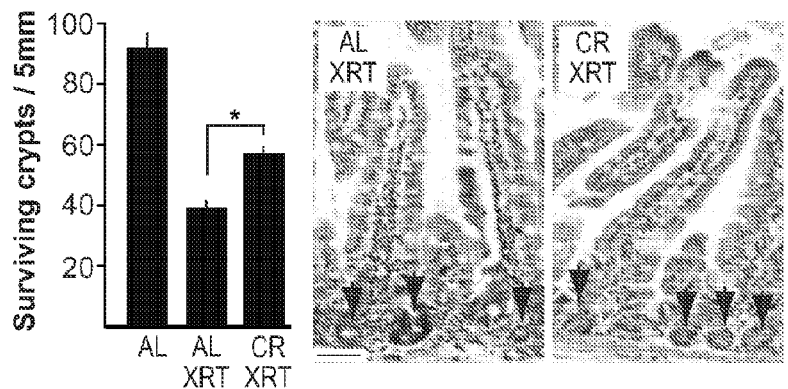

Disclosed herein are methods for stimulating the proliferation and/or self-renewal of one or more intestinal stem cells in mammalian intestinal tissue, such methods comprising contacting a population of Paneth cells or Paneth-like cells in the mammalian intestinal tissue with an effective amount of a calorie restriction mimetic. As used herein, a "population of cells" (e.g., a population of Paneth cells) can be a single cell or can comprise multiple cells in various embodiments. In some embodiments a population of cells comprises at least 10, $10^2$, $10^3$, $10^4$, $10^5$, $10^6$, $10^7$, $10^8$, $10^9$, $10^{10}$, $10^{11}$ cells, or more, or any range therebetween. In some embodiments of any relevant aspect herein a population of cells refers to multiple cells in a culture vessel such as a culture plate or dish. In some embodiments a population of cells refers to multiple cells exposed in parallel to the same agents or conditions. In some embodiments a population of cells refers to cells in a mammalian intestine in vivo. One of ordinary skill in the art will appreciate that a "population of cells" of a given type, such as population of Paneth cells at the base of the small intestinal crypts, or having particular characteristic(s) comprises at least one cell of such type or having such characteristic(s) and may or may not further comprise one or more cells of different type(s) and/or lacking such characteristic(s). In various embodiments a population of cells is selected or purified to a desired level of uniformity or homogeneity with respect to type and/or characteristic(s). For example, in various embodiments a population of cells contains at least 10%, 20%, 30%, 40%, 50%, 60%, 70%, 80%, 90%, 95%, or more cells of such type and/or having such characteristic(s). It will be understood that many of the methods described herein are often practiced using populations of cells comprising multiple cells, e.g., in vitro or in vivo. In some instances, ex vivo methods described herein are performed using populations of cells. Thus references to "a cell" should be understood as including embodiments in which the cell is a member of a population of cells. References to "cells" should be understood as including embodiments applicable to individual cells within a population comprising multiple cells and embodiments applicable to individual isolated cells. As will be understood by those of ordinary skill in the art, the number of members and/or one or more characteristic(s) of a population of cells may change over time, e.g., during a culture period. For example, at least some cells in the population may divide once or more and/or some cells may die. Hence, if a population of cells is maintained and/or subjected to one or more manipulations or steps, it should be understood that the population may have changed over time, and the term "population of cells" may thus refer to the population as it exists at the relevant time, e.g., the population resulting from the previous manipulation or step. It will also be appreciated that, in general, any manipulation or step performed on a population of cells may be performed on a subpopulation. For example, cells may be passaged, and only a portion of the cells retained for subsequent manipulation or steps, or a population may be divided into multiple aliquots, which may be used for different purposes.

Also disclosed is a method for stimulating the proliferation of Paneth cells and/or Paneth-like cells, such method comprising contacting a population of Paneth cells or Paneth-like cells with an effective amount of a calorie restriction mimetic.

The present invention also contemplates a method for preserving the normal morphology of Paneth cells and/or Paneth-like cells, such method comprising contacting a population of Paneth cells or Paneth-like cells with an effective amount of a calorie restriction mimetic.

As used herein, "calorie restriction mimetic" refers to an agent that attempts to reproduce one or more of the physiological effects that calorie restriction has on a mammal. As used herein, "calorie restriction" (CR), refers to the protocol of reducing caloric intake while maintaining adequate nutrition of a mammal. Surprisingly, the present inventors observed that calorie restriction promotes intestinal stem cell function, including, for example, increased proliferation and/or self-renewal of the intestinal stem cells. Without wishing to be bound by theory, it is believed that CR stimulates proliferation and self-renewal of intestinal stem cells, in part, by inhibiting the level and/or activity of mTORC1 in Paneth cells.

Mammalian target of rapamycin (mTOR) is a serine/threonine kinase that is evolutionarily conserved and integrates multiple physiological pathways, such as nutrients (e.g., amino acids and glucose), growth factors (e.g., insulin like growth factor 1), hormones (e.g., leptin), and stresses, including for example starvation, hypoxia, and damage to DNA, in order to regulate various cell functions, namely translation, transcription, cellular growth, metabolism, survival, energy balance and response to stress. (Watanabe, et al. J. Nucl. Med. 52(4):497-500, 2011). mTOR pathway dysregulation is implicated with various disease (e.g., cancer). mTORC1 is a multi-subunit kinase that possesses a large scaffolding protein known as regulatory associated protein of mTOR (Raptor), a small WD-40 repeat protein known as mLST8, as well as two regulatory proteins known as pRAs40 and DEPTOR, in addition to mTOR, which serves as the catalytic subunit for mTORC1. mTORC1 is responsible for phosphorylating S6K and 4E-BP1 (which may be used to assay for mTORC1 activity), and regulates numerous physiological processes, including, for example, translation, autophagy, growth, lipid biosynthesis, mitochondria biogenesis, and ribosome biogenesis. mTOR interacts with a specific component of mTORC1, known as Raptor, via binding to an N-terminal HEAT domain. Raptor serves as a scaffolding protein, and recruits SK6 and 4E-BP1 for the promotion of protein synthesis via direct phosphorylation by mTORC1 of S6K and 4E-BP1. A more detailed description of mTORC1, its mechanism of action, and various modulators of mTORC1 can be found in Liu et al. (Liu, et al. Drug Discov Today Ther Strateg. 6(2):47-55, 2009).

In some embodiments, CR stimulates the proliferation and self-renewal of intestinal stem cells, in part, by preserving the normal morphology of Paneth cell (or Paneth-like cells) and/or stimulating the proliferation of Paneth cells (or Paneth-like cells), thereby stimulating the proliferation and self-renewal of intestinal stem cells.

In some embodiments, a calorie restriction mimetic comprises an agent that inhibits the level and/or activity of mTORC1. "Agent" as used herein encompasses proteins, small molecules, nucleic acids, lipids, supramolecular complexes, entities such as viruses or portions thereof, and other biological or chemical entities that can be contacted with cells ex vivo or administered to a subject. An "agent" may comprise multiple different agents of distinct structure or sequence. The term "agent" may be used interchangeably with the term "compound" herein. In general, an agent disclosed herein can be prepared or obtained using any of a variety of methods. Methods suitable for preparation of particular agents or types of agents are known to those of ordinary skill in the art. For example, in various embodiments an agent is isolated from an organism that naturally contains or produces it (e.g., plants, animals, fungi, bacteria). In some embodiments an agent is at least partly synthesized, e.g., using chemical or biological methods. In some embodiments recombinant nucleic acid technology is used to produce an agent, e.g., a gene expression product such as an RNA or protein. Methods for generating genetically modified cells or organisms, e.g., cells (prokaryotic or eukaryotic) or organisms (e.g., animals, plants) that can serve as sources of the agent are known to those of ordinary skill in the art. Exemplary methods are described in various references cited herein. In some embodiments a protein or nucleic acid has or comprises a naturally occurring sequence. In some embodiments a protein or nucleic acid comprises or has a sequence that is at least in part invented or generated by man and/or not known to be found in nature. In some embodiments an agent or composition herein comprises a naturally occurring polypeptide. For purposes herein, a polypeptide is said to be "naturally occurring" if it has the amino acid sequence of a polypeptide found in nature. For example, a recombinantly produced polypeptide identical in sequence to a polypeptide found in nature is said to be a "naturally occurring" polypeptide. In some embodiments, a variant of a naturally occurring polypeptide is used. In some embodiments an agent disclosed herein or used in a method or composition herein (i.e., any such agent) is an isolated or purified agent.

The present invention contemplates the use of any agent which is capable of inhibiting the level and/or activity of mTORC1. "Inhibit", and derivations thereof, may be used interchangeably with terms such as "suppress", "decrease", "reduce" and like terms, as appropriate in the context. It will be understood that the extent of inhibition may vary. For example, inhibition may refer to a reduction of the relevant level by at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99%. In some embodiments inhibition refers to a decrease of 100%, e.g., to background levels or undetectable levels. The term "inhibitor" encompasses agents that inhibit (decrease, reduce) the expression or activity of a target. The term "inhibitor" encompasses agents that inhibit expression and/or inhibit one or more activities of a molecule or complex of interest (the "target"). For example, in various embodiments an agent is an "inhibitor" of a target if one or more activities of the target is reduced in the presence of the compound, or as a consequence of its use, as compared with in the absence of the compound, and/or if the level or amount of the target is reduced in the presence of the compound, or as a consequence of its use, as compared with in the absence of the compound. In certain embodiments, an inhibitor acts directly on a target in that it physically interacts with the target. In some embodiments, an inhibitor acts indirectly, e.g., by inhibiting a second molecule that is needed for synthesis or activity of the target. In some embodiments, an inhibitor is an antagonist. Methods of inhibiting encompass methods that result in a decreased amount of a target and methods that interfere with one or more functions (activities) of a target. In some embodiments, a target is inhibited by inhibiting or interfering with its expression or post-translational processing, so that a decreased amount of functional target is produced, resulting in a decreased overall activity of the target in a cell or system. A variety of methods useful for inhibiting or interfering with expression can be used in various embodiments. In general, such methods result in decreased synthesis of a mRNA and/or polypeptide and as a result, a reduction in the total level of activity present. Other means of inhibition include interfering with proper localization, secretion, or co- or post-translational processing, or promoting increased degradation. Methods of inhibiting activity can include binding to a target or to a receptor or co-receptor for the target and thereby blocking the target from interacting with its receptor(s) or with other molecule(s) needed for activity of the target. In some embodiments an inhibitor binds to an active site or catalytic residue or substrate binding site of an enzyme or blocks dimerization or other protein-protein interactions, etc. For example, in some embodiments a protein that acts as a dimer is inhibited using an agent that blocks dimerization. In some embodiments, an inhibitor comprises an RNAi agent, e.g., an siRNA or shRNA, or an antisense oligonucleotide, that inhibits expression of a target. In some embodiments, an inhibitor comprises an antibody or aptamer or small molecule that binds to and inhibits a target. In some embodiments an inhibitor comprises an agent that acts in a dominant negative fashion to inhibit a target. A dominant negative agent may comprise a fragment of a target molecule that lacks one or more domains necessary for function. For example, in some embodiments a dominant negative form of a TF comprises a DNA binding domain and/or dimerization domain but lacks an activation domain.

In some embodiments, an agent that inhibits the level and/or activity of mTORC1 attenuates the intrinsic kinase activity of mTOR. In some embodiments, the agent interferes with interaction between mTOR and a phosphorylation target of mTOR. In some embodiments, the agent prevents mTOR from phosphorylating serine and threonine residues. In some embodiments, the agent is selected from the group consisting of an anti sense nucleic acid, an oligopeptide, an aptamer, a ribozyme, a small molecule, an intrabody, an antibody or a fragment thereof. In some embodiments, the agent interferes with assembly of mTORC1. In some embodiments the agent inhibits synthesis of Raptor.

In some embodiments, the agent that inhibits the level and/or activity of mTORC1 comprises sirolimus or a derivative or analog thereof. The chemical structure of sirolimus, which is also known as rapamycin, is shown in Formula (I) below:

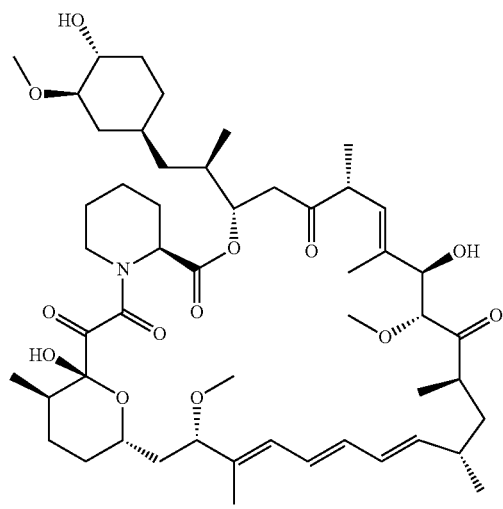

(I)

Rapamycin analogs, are also known as "rapalogs". Extensive literature on analogs, homologs, derivatives and other compounds structurally related to rapamycin ("rapalogs"), see, e.g., WO/2007143212 and references cited therein.

Non-limiting examples of suitable sirolimus derivatives which can be used as agents for inhibiting the level and/or activity of mTORC1 include temsirolimus, everolimus, and ridaforolimus.

Formula (II) below shows the chemical structure of temsirolimus:

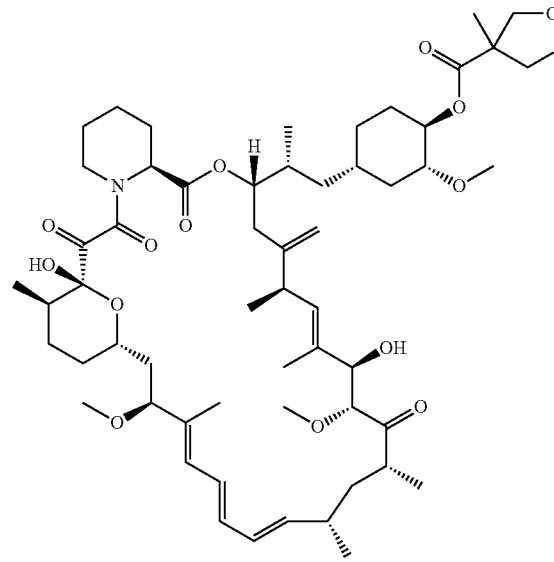

(II)

Formula (III) below shows the chemical structure of everolimus:

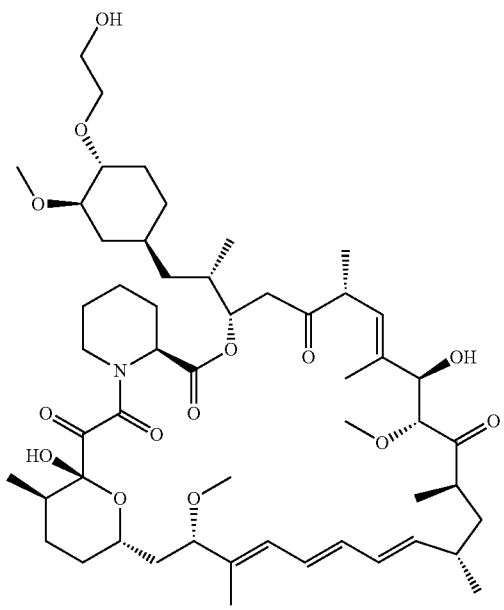

(III)

Formula (IV) below shows the chemical structure of ridaforolimus:

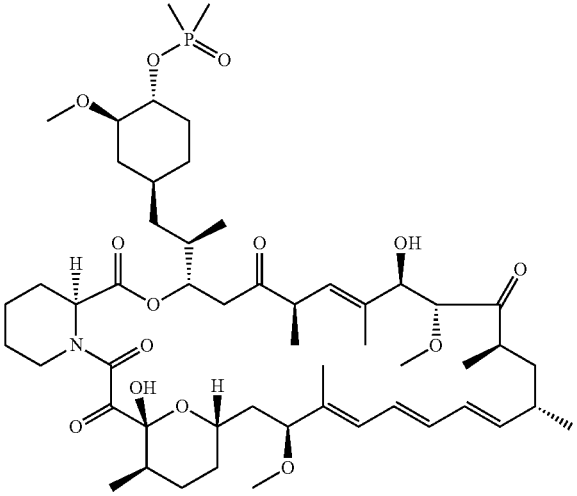

(IV)

In some embodiments, a sirolimus analog comprises a compound of Formula (V) below:

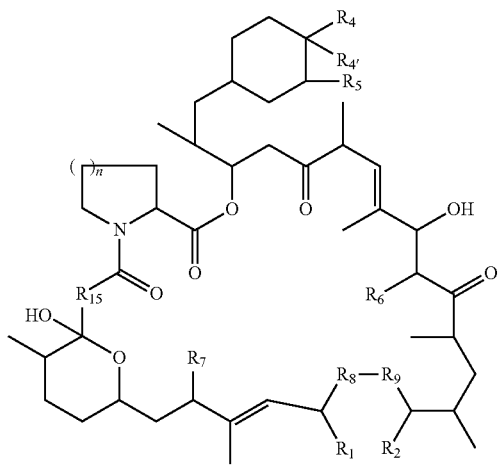

(V)

wherein: $R_1$ and $R_2$ are different, independent groups and are selected from the group consisting of $OR_3$ and $N(R_{3'})(R_{3''})$; or $R_1$ and $R_2$ are different, are connected through a single bond, and are selected from the group consisting of O and $NR_3$; $R_3$, $R_{3'}$, and $R_{3''}$ are independently selected from the group consisting of H, $C_1$ to $C_6$ alkyl, substituted $C_1$ to $C_6$ alkyl, $C_3$ to $C_8$ cycloalkyl, substituted $C_3$ to $C_8$ cycloalkyl, $C_6$ to $C_{20}$ aryl, substituted $C_6$ to $C_{20}$ aryl, heteroaryl, and substituted heteroaryl; $R_4$ and $R_{4'}$ are: (a) independently selected from the group consisting of H, OH, $O(C_1$ to $C_6$ alkyl), O(substituted $C_1$ to $C_6$ alkyl), O(acyl), O(aryl), O(substituted aryl), and halogen; or (b) taken together to form a double bond to O; $R_5$, $R_6$, and $R_7$ are independently selected from the group consisting of H, OH, and $OCH_3$; $R_8$ and $R_9$ are connected through a double bond and are CH; $R_{15}$ is selected from the group consisting of C=O, CHOH, and $CH_2$; n is 1 or 2; wherein the acyl group is HC(O)— or a —C(O)R'''— group, wherein R''' is selected from $C_1$ to $C_6$ alkyl, substituted $C_1$ to $C_6$ alkyl, and alkoxy; wherein the heteroaryl group consists of a monocyclic, saturated, partially saturated, or wholly unsaturated ring of 6-20 carbon atoms and one to four heteroatoms independently selected from N, S and O; wherein the substituents for the substituted $C_1$ to $C_6$ alkyl, $C_6$ to $C_{20}$ aryl, heteroaryl or acyl consist of one or more substituents independently selected from halogen, CN, OH, $NO_2$, amino, $C_6$ to $C_{20}$ aryl, a heterocyclic ring consisting of a monocyclic, saturated, partially saturated, or wholly unsaturated 4- to 7-membered ring having 1 to 4 heteroatoms independently selected from N, S, and O, alkoxy, aryloxy, alkylcarbonyl, alkylcarboxy, and arylthio; or a pharmaceutically acceptable salt thereof. Methods of synthesizing compounds of Formula (V) are described in U.S. Pat. No. 7,560,457, the teachings of which are incorporated herein by reference.

In some embodiments, a sirolimus derivative comprises a compound of Formula (VI):

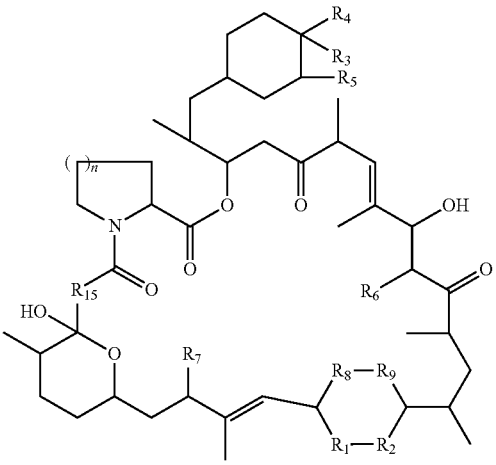

(VI)

wherein: $R_1$ and $R_2$ are the same or different and are selected from the group consisting of $CR_{16}R_{17}$ and $CR_{18}R_{19}$; $R_3$ and $R_4$ are: (a) independently selected from the group consisting of H, OH, $O(C_1$ to $C_6$ alkyl), O(substituted $C_1$ to $C_6$ alkyl), O(acyl), O(aryl), O(substituted aryl), and halogen; or (b) taken together to form a double bond to O; $R_5$, $R_6$, and $R_7$ are independently selected from the group consisting of H, OH, and $OCH_3$; $R_8$ and $R_9$ are connected though a (i) single bond and are $CH_2$ or (ii) double bond and are CH; $R_{15}$ is selected from the group consisting of C=O, CHOH, and $CH_2$; $R_{16}$ and $R_{17}$ are independently selected from the group consisting of H, $C_1$ to $C_6$ alkyl, $C_1$ to $C_6$ substituted alkyl, aryl, substituted aryl, acyl, $CF_3$, CN, and $NO_2$; $R_{18}$ and $R_{19}$ are independently selected from the group consisting of H, $C_1$ to $C_6$ alkyl, $C_1$ to $C_6$ substituted alkyl, aryl, substituted aryl, acyl, $CF_3$, CN, and $NO_2$; or $R_{17}$ and $R_{18}$ are taken together to form a monocyclic, saturated, partially unsaturated, or wholly unsaturated 5- to 7-membered ring optionally containing one to 4 heteroatoms independently selected from N, S and O; n is 1 or 2; wherein the acyl group is HC(O)— or a —C(O)R'''— group, wherein R''' is selected from the group consisting of alkyl, substituted alkyl, and alkoxy; wherein the substituents for the substituted alkyl, aryl, or acyl consist of one or more substituents independently selected from the group consisting of halogen, CN, OH, $NO_2$, amino, aryl, a heterocyclic ring consisting of a monocyclic, saturated, partially unsaturated, or wholly unsaturated 4- to 7-membered ring having 1 to 4 heteroatoms independently selected from N, S and O, alkoxy, aryloxy, alkylcarbonyl, alkylcarboxy, and arylthio; or a pharmaceutically acceptable salt thereof. Methods of synthesizing compounds of Formula (VI) are described in U.S. Pat. No. 7,273,874, the teachings of which are incorporated herein by reference.

In some embodiments, the agent that inhibits the level and/or activity of mTORC1 comprises any of a large number of small molecule inhibitors of mTOR kinase, for example, kinase inhibitors that binds to the ATP binding domain of mTOR and/or competitively inhibit mTOR kinase. Non-limiting examples of allosteric mTOR small molecule inhibitors comprise any of the compounds of Formula (VII) below:

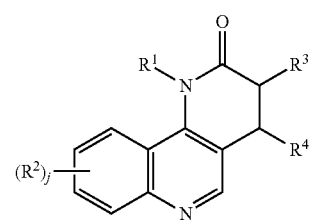

(VII)

wherein:

$R^1$ is an optionally substituted group selected from the group consisting of 6-10-membered aryl; $C_{7-15}$ arylalkyl; $C_{6-15}$ heteroarylalkyl; $C_{1-12}$ heteroaliphatic; $C_{1-12}$ aliphatic; 5-10-membered heteroaryl having 1-4 heteroatoms independently selected from the group consisting of nitrogen, oxygen, and sulfur; and 4-7-membered heterocyclic having 1-2 heteroatoms independently selected from the group consisting of nitrogen, oxygen, and sulfur; each occurrence of $R^2$ is independently halogen, —$NR_2$—OR, —SR, or an optionally substituted group selected from the group consisting Of $C_{1-j2}$ acyl; 6-10-membered aryl; $C_{7-I5}$ arylalkyl; $C_{6-I5}$ heteroarylalkyl; $C_{1-12}$ heteroaliphatic; $C_{1-12}$ aliphatic; 5-10-membered heteroaryl having 1-4 heteroatoms independently selected from the group consisting of nitrogen, oxygen, and sulfur; and 4-7-membered heterocyclic having 1-2 heteroatoms independently selected from the group consisting of nitrogen, oxygen, and sulfur; j is an integer from 1 to 4, inclusive;

$R^3$ and $R^4$ are independently hydrogen, hydroxyl, alkoxy, halogen, or optionally substituted $Cj_{-6}$ aliphatic, with the proviso that $R^3$ and $R^4$ are not taken together to form a ring; and each R is independently hydrogen, an optionally substituted group selected from the group consisting of $C_{1-12}$ acyl; 6-10-membered aryl; $C_{7-}J_5$ arylalkyl; $C_{6-15}$ heteroarylalkyl; $C_{1-12}$ aliphatic; 5-10-membered heteroaryl having 1-4 heteroatoms independently selected from the group consisting of nitrogen, oxygen, and sulfur; 4-7-membered heterocyclic having 1-2 heteroatoms independently selected from the group consisting of nitrogen, oxygen, and sulfur; and $C_{1-}J_2$ heteroaliphatic having 1-2 heteroatoms independently selected from the group consisting of nitrogen, oxygen, and sulfur; or: two R on the same nitrogen atom are taken with the nitrogen to form a 4-7-membered heterocyclic ring having 1-2 heteroatoms independently selected from the group consisting of nitrogen, oxygen, and sulfur. Methods of synthesizing sirolimus derivatives of Formula (VII) are described in PCT Application Publication WO 2010/044885.

Additional examples of small molecule mTOR inhibitors can be found in Liu et al. (2009). Additional non-limiting examples of ATP-competitive inhibitors that directly target the catalytic site of mTOR and result in significant inhibition of mTOR can be found in Hall M N, et al. (Hall et al. *Nat Rev Drug Discov.*, 10(11):868-80, 2011).

In some embodiments, an agent that inhibits the level and/or activity of mTORC1 comprises an AMP-activated protein kinase (AMPK) activator. AMPK protein kinase complex serves as an energy sensor that responds to rises in AMP levels by activating ATP-producing pathways and inhibiting ATP-consuming pathways. In some embodiments, an AMPK activator of the present invention comprises a member of the thienopyridone family of molecules. In some embodiments, the AMPK activator comprises small molecule A-769662 (Carling et al. Biol Chem. 282(45):32539-48, 2007). Cool et al. have described the identification and characterization of A-769662 (Cool et al. Cell Metab. June; 3(6):403-16, 2006). High-throughput assays for screening for additional AMPK activators that are capable of inhibiting the level and/or activity of mTORC1 are apparent to those skilled in the art.

In some embodiments, an agent that inhibits the level and/or activity of mTORC1 comprises a biguanidine. In some embodiments, a biguanidine comprises metformin or an analog or derivative thereof. In some embodiments, a biguanidine comprises phenformin. In some embodiments, the biguanidine comprises an AMPK activator. In some embodiments, the biguanidine acts independently of AMPK. In some instances, metformin can be used to inhibit the level and/or activity of mTORC1 in a rag GTPase-dependent manner (Thomas et al. Cell Metab. 11(5):390-401, 2010). High-throughput assays for screening for additional biguanidines that are capable of inhibiting the level and/or activity of mTORC1 are apparent to those skilled in the art.

In some embodiments, an agent that inhibits the level and/or activity of mTORC1 comprises an inhibitor of Rag GTPases. Rag GTPases reside upstream of mTOR in the mTORC1 signaling pathway, and bind Raptor to mediate amino acid signaling to mTORC1 (Sabatini et al. Science. 320(5882):1496-1501, 2008). In some embodiments, an inhibitor of Rag GTPases comprises metformin. High-throughput assays for screening for additional Rag GTPase inhibitors that are capable of inhibiting the level and/or activity of mTORC1 are apparent to those skilled in the art.

In some embodiments, agents that inhibit the level and/or activity of mTORC1 comprises agents that phenocopy TSC1 (Genbank Accession: EAW88021) and/or TSC2 (GenBank Accession: AAI50301). In some embodiments, agents that phenocopy TSC1 and/or TSC2 comprise TSC1 and/or TSC2 protein, and nucleic acids encoding TSC1 and/or TSC2 protein. TSC1 and TSC2 are negative regulators of mTORC1, namely the gene products of TSC1 and TSC2 interact to form a complex that functions as a GTPase activating protein (GAP) for rheb GTPase, blocking rheb-GTP-dependent stimulation of cellular growth via mTOR. It has been observed that in cells lacking TSC1 or TSC2, p70 S6K and ribosomal protein S6, the downstream targets of mTOR, are constitutively phosphorylated. (Nellist et al. BMC Med. Genetics. 9:10, 2008). High-throughput assays for screening for agents that phenocopy TSC1 and/or TSC2 and that are capable of inhibiting the level and/or activity of mTORC1 are apparent to those skilled in the art.

One of ordinary skill in the art will appreciate that some of the agents that inhibit the level and/or activity of mTORC1 may appropriately qualify as multiple types of mTORC1 inhibitors. Accordingly, the listing of an agent in one or more categories is not to be considered limiting.

Without wishing to be bound by theory, it is also believed that CR stimulates proliferation and self-renewal of intestinal stem cells, in part, by increasing the level and/or activity of bone stromal antigen 1 (Bst-1) or a product of Bst-1 in Paneth cells. Accordingly, in some embodiments, the calorie restriction mimetic comprises an agent that increases the level and/or activity of bone stromal antigen 1 (Bst-1, Gene ID: 683) or a product of Bst-1. Bst-1, is also known as ADP-ribosyl cyclase 2 and is a glycosylphosphatidylinositol-anchored molecule derived from stromal cells that is known to facilitate pre-B-cell growth. The amino acid sequence of Bst-1 protein (Accession EAW92744) is about 33% identical to cluster of differentiation 38 (CD38).

In some embodiments, the agent stimulates intracellular release of $Ca^{2+}$ from the sarcoplasmic reticulum. Any agent that is capable of stimulating intracellular release of $Ca^{2+}$ from the sarcoplasmic reticulum may be used in various embodiments. In some embodiments, the agent induces the ryanodine receptor to release calcium ions into the cytosol. The present invention contemplates the use of any ryanodine receptor agonist, for example, the class of compounds known as xanthines (e.g., caffeine), can induce the ryanodine receptor by potentiating its sensitivity to its native calcium ligand.

In some embodiments, the product of Bst-1 comprises cyclic ADP ribose. In some embodiments, the agent that increases the level and/or activity of Bst-1 is a nucleic acid sequence that encodes Bst-1. "Nucleic acid" is used interchangeably with "polynucleotide" and encompasses polymers of nucleotides. "Oligonucleotide" refers to a relatively short nucleic acid, e.g., typically between about 4 and about 100 nucleotides (nt) long, e.g., between 8-60 nt or between 10-40 nt long. Nucleotides include, e.g., ribonucleotides or deoxyribonucleotides. In some embodiments a nucleic acid comprises or consists of DNA or RNA. In some embodiments a nucleic acid comprises or includes only standard nucleobases (often referred to as "bases"). The standard bases are cytosine, guanine, adenine (which are found in DNA and RNA), thymine (which is found in DNA) and uracil (which is found in RNA), abbreviated as C, G, A, T, and U, respectively. In some embodiments a nucleic acid may comprise one or more non-standard nucleobases, which may be naturally occurring or non-naturally occurring (i.e., artificial; not found in nature) in various embodiments. In some embodiments a nucleic acid may comprise chemically or biologically modified bases (e.g., alkylated (e.g., methylated) bases), modified sugars (e.g., 2'-O-alkyribose (e.g., 2'-O methylribose), 2'-fluororibose, arabinose, or hexose), modified phosphate groups (e.g., phosphorothioates or 5'-N-phosphoramidite linkages). In some embodiments a nucleic acid comprises subunits (residues), e.g., nucleotides, that are linked by phosphodiester bonds. In some embodiments, at least some subunits of a nucleic acid are linked by a non-phosphodiester bond or other backbone structure. In some embodiments, a nucleic acid comprises a locked nucleic acid, morpholino, or peptide nucleic acid. A nucleic acid may be linear or circular in various embodiments. A nucleic acid may be single-stranded, double-stranded, or partially double-stranded in various embodiments. An at least partially double-stranded nucleic acid may be blunt-ended or may have one or more overhangs, e.g., 5' and/or 3' overhang(s). Nucleic acid modifications (e.g., base, sugar, and/or backbone modifications), non-standard nucleotides or nucleosides, etc., such as those known in the art as being useful in the context of RNA interference (RNAi), aptamer, or antisense-based molecules for research or therapeutic purposes may be incorporated in various embodiments. Such modifications may, for example, increase stability (e.g., by reducing sensitivity to cleavage by nucleases), decrease clearance in vivo, increase cell uptake, or confer other properties that improve the potency, efficacy, specificity, or otherwise render the nucleic acid more suitable for an intended use. Various non-limiting examples of nucleic acid modifications are described in, e.g., Deleavey G F, et al., Chemical modification of siRNA. Curr. Protoc. Nucleic Acid Chem. 2009; 39:16.3.1-16.3.22; Crooke, S T (ed.) Antisense drug technology: principles, strategies, and applications, Boca Raton: CRC Press, 2008; Kurreck, J. (ed.) Therapeutic oligonucleotides, RSC biomolecular sciences. Cambridge: Royal Society of Chemistry, 2008; U.S. Pat. Nos. 4,469,863; 5,536,821; 5,541,306; 5,637,683; 5,637,684; 5,700,922; 5,717,083; 5,719,262; 5,739,308; 5,773,601; 5,886,165; 5,929, 226; 5,977,296; 6,140,482; 6,455,308 and/or in PCT application publications WO 00/56746 and WO 01/14398. Different modifications may be used in the two strands of a double-stranded nucleic acid. A nucleic acid may be modified uniformly or on only a portion thereof and/or may contain multiple different modifications. It will be appreciated that naturally-occurring allelic variants of the reference sequence for a particular nucleic acid or protein may exist in the population, and such variants may be used in certain embodiments. It will also be appreciated that variants arising due to alternative splicing may exist, which are encompassed herein in various embodiments. In some embodiments, the agent is a functional fragment of a nucleic acid sequence that encodes Bst-1. In some embodiments, the agent is a variant of a nucleic acid sequence that encodes Bst-1. In some embodiments, the agent is a nucleic acid comprising a sequence that is homologous to a nucleic acid sequence that encodes Bst-1.

In some embodiments, the agent is a Bst-1 protein. A "polypeptide" refers to a polymer of amino acids linked by peptide bonds. A protein is a molecule comprising one or more polypeptides. A peptide is a relatively short polypeptide, typically between about 2 and 100 amino acids (aa) in length, e.g., between 4 and 60 aa; between 8 and 40 aa; between 10 and 30 aa. The terms "protein", "polypeptide", and "peptide" may be used interchangeably. In general, a polypeptide may contain only standard amino acids or may comprise one or more non-standard amino acids (which may be naturally occurring or non-naturally occurring amino acids) and/or amino acid analogs in various embodiments. A "standard amino acid" is any of the 20 L-amino acids that are commonly utilized in the synthesis of proteins by mammals and are encoded by the genetic code. A "non-standard amino acid" is an amino acid that is not commonly utilized in the synthesis of proteins by mammals. Non-standard amino acids include naturally occurring amino acids (other than the 20 standard amino acids) and non-naturally occurring amino acids. In some embodiments, a non-standard, naturally occurring amino acid is found in mammals. For example, ornithine, citrulline, and homocysteine are naturally occurring non-standard amino acids that have important roles in mammalian metabolism. Exemplary non-standard amino acids include, e.g., singly or multiply halogenated (e.g., fluorinated) amino acids, D-amino acids, homo-amino acids, N-alkyl amino acids (other than proline), dehydroamino acids, aromatic amino acids (other than histidine, phenylalanine, tyrosine and tryptophan), and $\alpha,\alpha$ disubstituted amino acids. An amino acid, e.g., one or more of the amino acids in a polypeptide, may be modified, for example, by addition, e.g., covalent linkage, of a moiety such as an alkyl group, an alkanoyl group, a carbohydrate group, a phosphate group, a lipid, a polysaccharide, a halogen, a linker for conjugation, a protecting group, etc. Modifications may occur anywhere in a polypeptide, e.g., the peptide backbone, the amino acid side-chains and the amino or carboxyl termini. A given polypeptide may contain many types of modifications. Polypeptides may be branched or they may be cyclic, with or without branching. Polypeptides may be conjugated with, encapsulated by, or embedded within a polymer or polymeric matrix, dendrimer, nanoparticle, microparticle, liposome, or the like. Modification may occur prior to or after an amino acid is incorporated into a polypeptide in various embodiments. Polypeptides may, for example, be purified from natural sources, produced in vitro or in vivo in suitable expression systems using recombinant DNA technology (e.g., by recombinant host cells or in transgenic animals or plants), synthesized through chemical means such as conventional solid phase peptide synthesis, and/or methods involving chemical ligation of synthesized peptides (see, e.g., Kent, S., J Pept Sci., 9(9):574-93, 2003 or U.S. Pub. No. 20040115774), or any combination of the foregoing. One of ordinary skill in the art will understand that a protein may be composed of a single amino acid chain or multiple chains associated covalently or noncovalently. In some embodiments, the agent is a functional domain or fragment of Bst-1 protein. In some embodiments, the agent is a functional homolog of Bst-1 protein. In some embodiments, the agent is a fusion protein comprising Bst-1. In some embodiments, the agent is a variant of Bst-1 protein.

A "variant" of a particular polypeptide or polynucleotide has one or more alterations (e.g., additions, substitutions, and/or deletions, which may be referred to collectively as "mutations") with respect to the polypeptide or polynucleotide, which may be referred to as the "original polypeptide" or "original polynucleotide", respectively. An addition may be an insertion or may be at either terminus. A variant may be shorter or longer than the original polypeptide or polynucleotide. The term "variant" encompasses "fragments". A "fragment" is a continuous portion of a polypeptide or polynucleotide that is shorter than the original polypeptide. In some embodiments a variant comprises or consists of a fragment. In some embodiments a fragment or variant is at least 20%, 30%, 40%, 50%, 60%, 70%, 80%, 90%, 95%, 96%, 97%, 98%, 99%, or more as long as the original polypeptide or polynucleotide. A fragment may be an N-terminal, C-terminal, or internal fragment. In some embodiments a variant polypeptide comprises or consists of at least one domain of an original polypeptide. In some embodiments a variant polynucleotide hybridizes to an original polynucleotide under stringent conditions, e.g., high stringency conditions, for sequences of the length of the original polypeptide. In some embodiments a variant polypeptide or polynucleotide comprises or consists of a polypeptide or polynucleotide that is at least 50%, 60%, 70%, 80%, 90%, 95%, 96%, 97%, 98%, 99%, or more identical in sequence to the original polypeptide or polynucleotide over at least 20%, 30%, 40%, 50%, 60%, 70%, 80%, 90%, 95%, 96%, 97%, 98%, 99%, or 100% of the original polypeptide or polynucleotide. In some embodiments a variant polypeptide comprises or consists of a polypeptide that is at least 50%, 60%, 70%, 80%, 90%, 95%, 96%, 97%, 98%, 99%, or more identical in sequence to the original polypeptide over at least 20%, 30%, 40%, 50%, 60%, 70%, 80%, 90%, 95%, 96%, 97%, 98%, 99%, or 100% of the original polypeptide, with the proviso that, for purposes of computing percent identity, a conservative amino acid substitution is considered identical to the amino acid it replaces. In some embodiments a variant polypeptide comprises or consists of a polypeptide that is at least 50%, 60%, 70%, 80%, 90%, 95%, 96%, 97%, 98%, 99%, or more identical to the original polypeptide over at least 20%, 30%, 40%, 50%, 60%, 70%, 80%, 90%, 95%, 96%, 97%, 98%, 99%, or 100% of the original polypeptide, with the proviso that any one or more amino acid substitutions (up to the total number of such substitutions) may be restricted to conservative substitutions. In some embodiments a percent identity is measured over at least 100; 200; 300; 400; 500; 600; 700; 800; 900; 1,000; 1,200; 1,500; 2,000; 2,500; 3,000; 3,500; 4,000; 4,500; or 5,000 amino acids. In some embodiments the sequence of a variant polypeptide comprises or consists of a sequence that has N amino acid differences with respect to an original sequence, wherein N is any integer between 1 and 10 or between 1 and 20 or any integer up to 1%, 2%, 5%, or 10% of the number of amino acids in the original polypeptide, where an "amino acid difference" refers to a substitution, insertion, or deletion of an amino acid. In some embodiments a difference is a conservative substitution. Conservative substitutions may be made, e.g., on the basis of similarity in side chain size, polarity, charge, solubility, hydrophobicity, hydrophilicity and/or the amphipathic nature of the residues involved. In some embodiments, conservative substitutions may be made according to Table A, wherein amino acids in the same block in the second column and in the same line in the third column may be substituted for one another other in a conservative substitution. Certain conservative substitutions are substituting an amino acid in one row of the third column corresponding to a block in the second column with an amino acid from another row of the third column within the same block in the second column.

TABLE A

| Aliphatic | Non-polar | G A P |
|---|---|---|
| | | I L V |
| | Polar - uncharged | C S T M |
| | | N Q |
| | Polar - charged | D E |
| Aromatic | | K R |
| | | H F W Y |

In some embodiments, an agent that increases the level and/or activity of the product of Bst-1 is cluster of differentiation 38 (CD38) protein (GenBank Accession BAA18966). CD38, an ADP-ribosyl cyclase, is a glycoprotein which is located on the surface of various immune cells, and is involved a role in cell adhesion, signal transduction, and calcium signaling. CD38 is a multifunctional ectoenzyme that is responsible for catalyzing synthesis of cADPR. In some embodiments, the agent is a nucleic acid having a sequence that encodes a functional CD38 protein or a functional fragment thereof.

It should be appreciated that the nucleic acids and proteins of the present invention (e.g., Bst-1 and CD38) can include stability and expression enhancing modifications. Suitable stability and expression enhancing modifications are apparent to those of ordinary skill in the art.

Disclosed herein is a method of treating an affliction characterized by intestinal atrophy comprising stimulating the proliferation and/or self-renewal of intestinal stem cells in the patient. "Treat", "treating" and similar terms refer to providing medical and/or surgical management of a subject. Treatment can include, but is not limited to, administering an agent or composition (e.g., a pharmaceutical composition) to a subject. Treatment is typically undertaken in an effort to alter the course of a disease, disorder, or undesirable condition in a manner beneficial to the subject. The effect of treatment can generally include reversing, alleviating, reducing severity of, delaying the onset of, curing, inhibiting the progression of, and/or reducing the likelihood of occurrence or reoccurrence of the disease, disorder, or condition to which such term applies, or one or more symptoms or manifestations of such disease, disorder or condition. In some embodiments an agent or composition is administered to a subject who has developed a disease or condition or is at increased risk of doing so relative to a member of the general population. In some embodiments an agent or composition is administered prophylactically, i.e., before development of any symptom or manifestation of a condition. Typically in this case the subject will be at risk of developing the condition. It will be understood that "administering" encompasses self-administration. "Preventing" can refer to administering an agent or composition (e.g., a pharmaceutical composition) to a subject who has not developed a disease or condition, so as to reduce the likelihood that the disease or condition will occur or so as to reduce the severity of the disease or condition should it occur. The subject may be identified as at risk of developing the disease or condition (e.g., at increased risk relative to many most other members of the population (who may be matched with respect to various demographic factors such as age, sex, ethnicity, etc.) or as having one or more risk factors that increases likelihood of developing the disease or condition. Stimulating the proliferation and/or self-renewal of intestinal stem cells in the patient can be achieved by administering to the patient an effective amount of a calorie restriction mimetic. It should be appreciated that, in some instances, it may be advantageous to place the patient on a CR intervention concomitantly with administration of the calorie restriction mimetic. In certain instances, it may be advantageous to place the patient on a CR intervention alone to stimulate the proliferation and/or self-renewal of intestinal stem cells in the patient. For example, a CR regimen may be appropriate before administering a calorie restriction mimetic to the patient, and the number of Paneth cells and intestinal stem cells in the patient can be assayed for an increase in the number of Paneth cells and intestinal stem cells. The results of the assay can thus be used as a quantitative measure of the success of the CR regimen alone, and to determine whether it may be advantageous to administer a calorie restriction mimetic. It may also be advantageous to place the patient on a CR regimen if, for example, the patient is taking medication which is contraindicated for the calorie restriction mimetic. It is believed that stimulating the proliferation and/or self-renewal of intestinal stem cells may ameliorate intestinal atrophy by regenerating intestinal tissue as the intestinal stem cells in the intestine proliferate and self-renew. In some embodiments, a method of treating an affliction characterized by intestinal atrophy comprises preserving the normal morphology of Paneth cells in a patient, comprising administering to the patient an effective amount of a calorie restriction mimetic. In some embodiments, a method of treating an affliction characterized by intestinal atrophy comprises stimulating the proliferation of Paneth cells in a patient, comprising administering to the patient an effective amount of a calorie restriction mimetic.

An "effective amount" or "effective dose" of an agent (or composition containing such agent) generally refers to the amount sufficient to achieve a desired biological and/or pharmacological effect, e.g., when contacted with a cell in vitro or administered to a subject according to a selected administration form, route, and/or schedule. As will be appreciated by those of ordinary skill in the art, the absolute amount of a particular agent or composition that is effective may vary depending on such factors as the desired biological or pharmacological endpoint, the agent to be delivered, the target tissue, etc. Those of ordinary skill in the art will further understand that an "effective amount" may be contacted with cells or administered in a single dose, or through use of multiple doses, in various embodiments. It will be understood that agents, compounds, and compositions herein may be employed in an amount effective to achieve a desired biological and/or therapeutic effect.

In some embodiments, a method of treating an affliction characterized by intestinal atrophy can be achieved by administering an effective amount of an agent that inhibits the level and/or activity of mTORC1 to the patient, for example, sirolimus or a derivative or analog thereof, thereby stimulating the proliferation and/or self-renewal of intestinal stem cells in the patient.

In some embodiments, a method of treating an affliction characterized by intestinal atrophy can be achieved by administering an effective amount of an appetite suppressant to the patient. Suitable appetite suppressants are apparent to the skilled person. In some instances, vitamin supplementation may help maintain adequate nutrition while the patient is taking the appetite suppressant.

In some embodiments, a method of treating an affliction characterized by intestinal atrophy is achieved by administering an effective amount of an agent that increases the level and/or activity of Bst-1 to the patient, or a product of Bst-1, such as cyclic ADP ribose, for example. In an embodiment, an agent that increases the level and/or activity of a product of Bst-1 (i.e., cyclic ADP ribose) comprises CD38.

Non-limiting examples of afflictions that are characterized by intestinal atrophy and for which a calorie restriction mimetic of the present invention may provide a useful remedy include inflammatory diseases (e.g, inflammatory bowel disease, e.g., Crohn's disease, ulcerative colitis), autoimmune diseases, vascular disease, cancer, infection, drug-induced or toxin-induced intestinal injury (e.g., cancer chemotherapy induced GI damage), an affliction treatable by parenteral nutrition (PN) or life-long parenteral nutrition, and exposure to ionizing radiation.

In some embodiments, the present invention contemplates compositions, agents, and methods for treating colitis, and particularly contemplates any suitable therapy for treating any type of colitis. Illustrative examples of the types of colitis that can be treated by the compositions, agents, and methods of the present invention include, but are not limited to infectious colitis, vascular colitis (e.g., ischemic colitis), pseudomembranous colitis (e.g., caused by bacteria, such as *Clostridium difficile*, for example), microscopic colitis, drug-induced colitis, allergic colitis, colitis related to diverticular disease, and intestinal lesions (e.g., ulcers) resulting from any of foregoing, or intestinal lesions resulting from any other cause whether causes by any other factors (e.g., genetics, physical injury, stress, to name only a few). In some embodiments, a calorie restriction mimetic, a composition comprising the calorie restriction mimetic, and/or an agent or composition comprising an agent of the present invention can be used to treat pseudomembranous colitis (e.g., microorganism induced colitis, e.g., bacteria, e.g., *C. difficile*). In some embodiments, a method for treating colitis resulting at least in part from infection by a pathogen, e.g., pseudomembranous colitis resulting at least in part from infection by a pathogen comprises: (a) administering an effective amount of an antibiotic to an agent, wherein the antibiotic rids or helps rid the patient of a pathogen; and (b) grafting gastrointestinal tissue generated ex vivo into the patient; and optionally (c) administering to the patient and effective amount of a calorie restriction mimetic. In some embodiments, such method further comprises (d) placing the patient on a CR intervention. In some embodiments, the gastrointestinal tissue comprises crypts generated ex vivo in accordance with the ex vivo methods described infra. In some embodiments, the gastrointestinal tissue generated ex vivo replaces damaged intestinal lining. In some embodiments, the gastrointestinal tissue generated ex vivo replaces denuded intestinal lining. In some embodiments, the calorie restriction mimetic is administered to the patient for a pre-determined period of time prior to administration of the antibiotic and/or grafting the gastrointestinal tissue generated ex vivo into the patient. Administering the calorie restriction mimetic to the patient prior to administration of the antibiotic and/or grafting the gastrointestinal tissue can advantageously serve as a way to prime the gastrointestinal cells of the patient (Paneth or Paneth-like cells, and or ISCs) to minimize drug induced injury resulting from administration of the antibiotic, as well as, to prime the existing gastrointestinal tissue to facilitate the grafting of the gastrointestinal tissue generated ex vivo, for example, to aid the process of healing of the tissue as the existing tissue and the grafted tissue become whole. The pre-determined period of time can range widely, for example, from up to one month prior to administration of the antibiotic agent and/or grafting of the ex vivo produced gastrointestinal tissue, until as little as a few hours prior thereto (e.g., 1-4 hours). It should be appreciated that any antibiotic agent that is known to treat the bacterial infection can be used to rid the patient of pathogens, for example, C. difficile can be treated with the antibiotics metronidazole and vanocin.

In some embodiments, a calorie restriction mimetic can be employed in combination with PN treatment.

In some embodiments, a calorie restriction mimetic can be used to treat short bowel syndrome (SBS). SBS in infants and children include necrotizing enterocolitis, midgut volvulus, intestinal atresia, and gastroschisis. In adults, SBS typically occurs as a post-surgical event post resection of substantial portions of the small intestine, such as, for example, surgery due to cancer, gastrointestinal bleeding (e.g., repeated or intractable, inflammatory bowel disease, trauma, etc). In some embodiments, a method for treating SBS comprises administering to a patient in need thereof an effective amount of a calorie restriction mimetic, and administering to the patient parenteral nutrition (PN). In some embodiments, such method for treating SBS further comprises administering to the patient an effective amount of glucagon-like peptide-2 (GLP-2) or an analog of GLP-2, for example, teduglutide (Tee et al. Clin. Exper. Gastroenterology. 4: 189-196, 2011).

The present invention contemplates agents useful for stimulating the proliferation of Paneth cells or Paneth-like cells, preserving the normal morphology of Paneth cells or Paneth-like cells, and/or stimulating the proliferation and/or self-renewal of ISCs, which may be useful for the treatment of afflictions characterized by intestinal atrophy, degeneration, and/or injury. In some embodiments, the agent comprises an agent that inhibits the level and/or activity of mTORC1, for example, sirolimus or a derivative or analog thereof. In some embodiments, the agent comprises an agent that increases the level and/or activity of Bst-1. In some embodiments, the agent is an agent that increases the level and/or activity of cADPR. In some embodiments, the agent is an analog of cADPR. Examples of cADPR analogs (e.g., cADPR-2'-P, 2'-deoxy-cADPR, and 3'-deoxy-cADPR), as well as chemical and enzymatic routes of synthesizing cADPR can be found in Walseth and Lee (Walseth T. F. and Lee, H. C. (2002) Pharmacology of cyclic ADP-ribose and NAADP. Synthesis and properties of analogs. In *Cyclic ADP-Ribose and NAADP. Structures, Metabolism and Functions*. Lee, H. C. (ed), pp. 121-142, Dordrecht: Kluwer). Walseth and Lee also describe the synthesis of various hydrolysis-resistant cADPR analogs, which may be employed in the compositions and methods of the present invention. Non-limiting examples of such analogs include cArisDPR, cADPcR, 7-deaza-cADPR, and 3-deaza-cADPR. (Id.). In some embodiments, an agent that increases the level and/or activity of cADPR is CD38. In some embodiments, the agent is an agent that increases the release of intracellular calcium ions. In some embodiments, the agent is an agent that activates the ryanodine receptor.

Figure 13A:
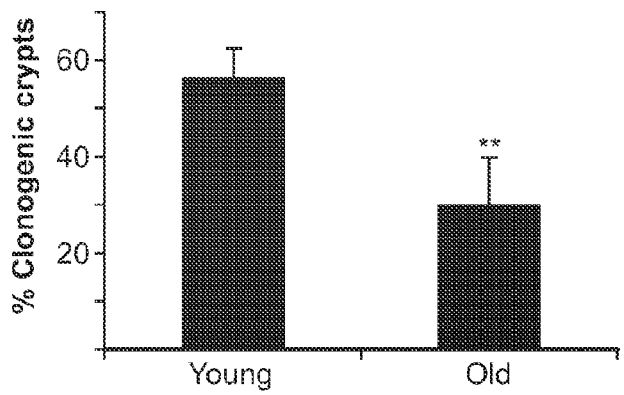
FIGS. 13a-c. Intestinal stem cell function declines with age and is enhanced cell-extrinsically by Paneth cells in response to CR or Rapamycin treatment. (a) Clonogenicity of small intestinal crypts isolated from 3 or 18 month old mice. (b, c) Clonogenicity of ISCs co-cultured with Paneth cells from CR mice (b) or Rapamycin-treated mice (c) is significantly increased vs. Paneth cells from ad-libitum (AL) fed mouse.
Figure 13B:
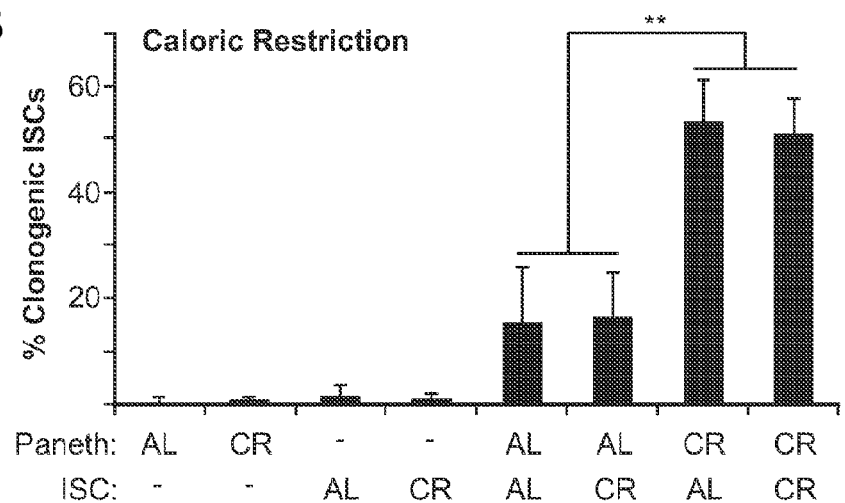
Figure 13C:
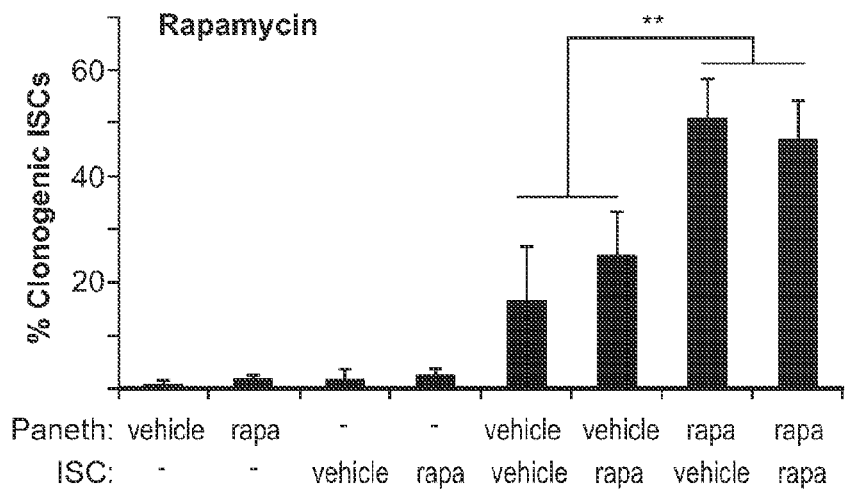
Figure 14B:
FIGS. 14a-c. 6 Increase in the number of morphologically normal Paneth cells with Rapamycin treatment before and after treatment with ionizing radiation. (a) Control animal treated with 10 Gy ionizing radiation. (b, c) 10 Gy ionizing radiation followed by Rapamycin (a) and after Rapamycin treatment followed by 10 Gy ionizing radiation followed by Rapamycin. There is an increase in the number of morphologically normal Paneth cells (b, c, arrows).
Figure 14C:
Figure 14A:
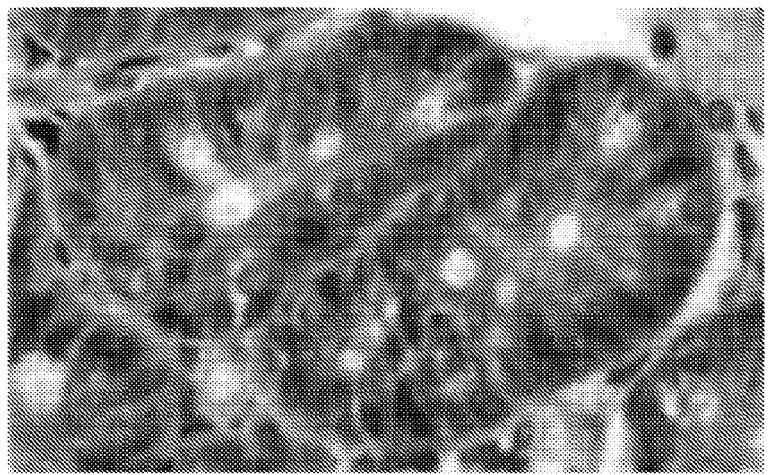

In work described herein it has been demonstrated caloric restriction and treatment with rapamycin are both capable of increasing normal intestinal stem cell (ISC) and Paneth cell number and function, and that rapamycin treatment is capable of protecting Paneth cells in the small intestine of mice from high doses of ionizing radiation. Paneth cells are essential to the survival of Lgr5+ intestinal stem cells. Crypts from aged mice exhibit a decline in the clonogenicity of their crypts (FIG. 13a). The clonogenicity of ISCs is enhanced by co-culturing of these cells with Paneth cells from mice treated with caloric restriction or rapamycin (FIG. 13a). Mice were pre-treated with rapamycin (4 mg/kg IP daily for 1 week) followed by a 10 Gy dose of gamma rays from a 137 Cs source, followed by intermittent treatment with rapamycin at the same dose for two weeks, after which mice were sacrificed before they exhibited distress from GI syndrome. Mice were also treated with 10 Gy of radiation followed by intermittent treatment with rapamycin over the two weeks. Histologic examination of the intestines revealed significantly higher numbers of Paneth cells in both the pre- and post-treated mice, and the post-treated mice in comparison to a control mouse that received an identical dose of ionizing radiation but did not receive rapamycin (FIG. 14). These results provide the first evidence that rapamycin may serve as a radioprotector in the small intestine likely by mimicking the effects of caloric restriction. Accordingly, rapamycin and derivatives or analogs or other agents thereof which inhibit mTOR, and/or and caloric restriction can be employed as agents for increasing the number and function of intestinal stem cells and Paneth cells, and as radioprotective agents against the acute and late toxicities of deliberate and accidental exposure to ionizing radiation.

In some embodiments, the agent is a radioprotective agent useful for protecting cells from ionizing radiation. In some embodiments, the radioprotective agent preserves the normal morphology of Paneth cells. In some embodiments, the radioprotective agent preserves the normal morphology of Paneth-like cells. In some embodiments, the radioprotective agent stimulates the proliferation of Paneth cells. In some embodiments, the radioprotective agent stimulates the proliferation of Paneth-like cells. In some embodiments, the radioprotective agent stimulates the proliferation of intestinal stem cells. In some embodiments, the radioprotective agent stimulates the self-renewal of intestinal stem cells. In some embodiments, the radioprotective agent is an agent that inhibits the level and/or activity of mTORC1. In some embodiments, a radioprotective agent of the present invention comprises sirolimus or a derivative or analog thereof. As noted above, suitable derivatives of sirolimus include, but are not limited to temsirolimus, everolimus, and ridaforolimus. In embodiments disclosed herein, a radioprotective agent of the present invention may prevent or ameliorate the harmful effects of ionizing radiation on mammalian cells (e.g., damage to gastrointestinal cells). In embodiments disclosed herein, the radioprotective agent stimulates the proliferation and/or self-renewal of intestinal stem cells and/or Paneth cells or Paneth-like cells. It should be appreciated that any agent that inhibits the level and/or activity of mTORC1 may serve as a radioprotective agent. In some embodiments, the radioprotective agent inhibits the level and/or activity of mTORC1 in mammalian Paneth cells. In some embodiments, the radioprotective agent is an agent that increases the level and/or activity of Bst-1. In some embodiments, the radioprotective agent is an agent that increases the level and/or activity of cADPR. In some embodiments, the agent is an analog of cADPR. In some embodiments, an agent that increases the level and/or activity of cADPR is CD38. In some embodiments, the radioprotective agent is an agent that increases the release of intracellular calcium ions. In some embodiments, the radioprotective agent is an agent that activates the ryanodine receptor.

In some embodiments, an agent of the present invention is administered in combination with a cancer therapeutic agent. It should be appreciated that the combined administration of an agent of the present invention and a cancer therapeutic agent can be achieved by formulating the cancer therapeutic agent and agent in the same composition or by administering the cancer therapeutic agent and agent separately (e.g., before, after, or interspersed with doses or administration of the cancer therapeutic agent). In some embodiments, the an agent of the present invention (e.g., a radioprotective agent) is administered to a patient undergoing conventional chemotherapy and/or radiotherapy e.g., to prevent, minimize or ameliorate harmful effects to the patient as a result of drug induced GI toxicity or damage, and/or exposure to the cancer therapeutic agent or ionizing radiation of the radiotherapy. In some embodiments, the cancer therapeutic agent is a chemotherapeutic agent. In some embodiments, the cancer therapeutic agent is an immunotherapeutic agent. In some embodiments, the cancer therapeutic agent is a radiotherapeutic agent. Exemplary chemotherapeutic agents that can be administered in combination with the agents of the present invention (e.g., a radioprotective agent) include alkylating agents (e.g. cisplatin, carboplatin, oxaloplatin, mechlorethamine, cyclophosphamide, chorambucil, nitrosureas); anti-metabolites (e.g. methotrexate, pemetrexed, 6-mercaptopurine, dacarbazine, fludarabine, 5-fluorouracil, arabinosycytosine, capecitabine, gemcitabine, decitabine); plant alkaloids and terpenoids including vinca alkaloids (e.g. vincristine, vinblastine, vinorelbine), podophyllotoxin (e.g. etoposide, teniposide), taxanes (e.g. paclitaxel, docetaxel); topoisomerase inhibitors (e.g. notecan, topotecan, amasacrine, etoposide phosphate); antitumor antibiotics (dactinomycin, doxorubicin, epirubicin, and bleomycin); ribonucleotides reductase inhibitors; antimicrotubules agents; and retinoids. (See, e.g., Cancer: Principles and Practice of Oncology (V. T. DeVita, et al., eds., J. B. Lippincott Company, 9$^{th}$ ed., 2011; Brunton, L., et al. (eds.) Goodman and Gilman's The Pharmacological Basis of Therapeutics, 12$^{th}$ Ed., McGraw Hill, 2010).

Exemplary immunotherapeutic agents include cytokines, such as, for example interleukin-1 (IL-1), IL-2, IL-4, IL-5, IL-β, IL-7, IL-10, IL-12, IL-I5, IL-18, CSF-GM, CSF-G, IFN-γ, IFN-α, TNF, TGF-β but not limited thereto.

In some embodiments, an agent of the present invention can be linked or conjugated to a delivery vehicle, which may also contain cancer therapeutic. Suitable delivery vehicles include liposomes (Hughes et al. Cancer Res 49(22):6214-20, 1989, which is hereby incorporated by reference in its entirety), nanoparticles (Farokhzad et al. Proc Nat'l Acad Sci USA 103(16):6315-20, 2006, which is hereby incorporated by reference in its entirety), biodegradable microspheres, microparticles, and collagen minipellets. The delivery vehicle can contain any of the radioprotective, chemotherapeutic, radiotherapeutic, or immunotherapeutic agents described supra.

In one embodiment, an agent of the present invention can be conjugated to a liposome delivery vehicle (Sofou and Sgouros, Exp Opin Drug Deliv. 5(2):189-204, 2008, which is hereby incorporated by reference in its entirety). Liposomes are vesicles comprised of one or more concentrically ordered lipid bilayers which encapsulate an aqueous phase. Suitable liposomal delivery vehicles are apparent to those skilled in the art. Different types of liposomes can be prepared according to Bangham et al. J. Mol. Biol. 13:238-52, 1965; U.S. Pat. No. 5,653,996 to Hsu; U.S. Pat. No. 5,643,599 to Lee et al.; U.S. Pat. No. 5,885,613 to Holland et al.; U.S. Pat. No. 5,631,237 to Dzau & Kaneda; and U.S. Pat. No. 5,059,421 to Loughrey et al., which are hereby incorporated by reference in their entirety.

These liposomes can be produced such that they contain, in addition to the therapeutic agents of the present invention, other therapeutic agents, such as immunotherapeutic cytokines, which would then be released at the target site (e.g., Wolff et al., Biochim. Biophys. Acta. 802:259-73, 1984, which is hereby incorporated by reference in its entirety).

The present invention also contemplates a composition comprising an agent of the present invention (e.g., an agent that stimulates the proliferation and/or self-renewal of ISCs, e.g., a radioprotective agent) and a pharmaceutically acceptable carrier, diluent, or excipient. Therapeutic formulations of the agents of the present invention can be prepared having the desired degree of purity with optional pharmaceutically acceptable carriers, excipients or stabilizers (REMINGTON'S PHARMACEUTICAL SCIENCES (A. Osol ed. 1980), which is hereby incorporated by reference in its entirety), in the form of lyophilized formulations or aqueous solutions. Acceptable carriers, excipients, or stabilizers are nontoxic to recipients at the dosages and concentrations employed, and include buffers such as acetate, Tris-phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; tonicifiers such as trehalose and sodium chloride; sugars such as sucrose, mannitol, trehalose or sorbitol; surfactant such as polysorbate; salt-forming counter-ions such as sodium; metal complexes (e.g., Zn-protein complexes); and/or non-ionic surfactants such as TWEEN®, PLURONICS® or polyethylene glycol (PEG).

The active therapeutic ingredients of the pharmaceutical compositions (e.g., radioprotective agents alone or in combination with or linked to a cancer therapeutic agent or radiotherapeutic agent) can be entrapped in microcapsules prepared using coacervation techniques or by interfacial polymerization, e.g., hydroxymethylcellulose or gelatin-microcapsules and poly-(methylmethacylate) microcapsules, respectively, in colloidal drug delivery systems (e.g., liposomes, albumin microspheres, microemulsions, nano-particles and nanocapsules) or in macroemulsions. Such techniques are disclosed in REMINGTON'S PHARMACEUTICAL SCIENCES (A. Osol ed. 1980), which is hereby incorporated by reference in its entirety. In some embodiments, the radioprotective agents of the present invention can be conjugated to the microcapsule delivery vehicle to target the delivery of the therapeutic agent to the site of the cells exposed to toxic effects of ionizing radiation. Sustained-release preparations may be prepared. Suitable examples of sustained-release preparations include semipermeable matrices of solid hydrophobic polymers containing the antibody or polypeptide, which matrices are in the form of shaped articles, e.g., films or microcapsules. Examples of sustained-release matrices include polyesters, hydrogels (for example, poly(2-hydroxyethyl-methacrylate), or poly(vinylalcohol)), polylactides, copolymers of L-glutamic acid and .gamma. ethyl-L-glutamate, non-degradable ethylene-vinyl acetate, degradable lactic acid-glycolic acid copolymers such as the LUPRON DEPOT® (injectable microspheres composed of lactic acid-glycolic acid copolymer and leuprolide acetate), and poly-D-(−)-3-hydroxybutyric acid.

In some embodiments, an agent of the present invention (e.g., a radioprotective agent) can be provided with an enteric coating or otherwise protected from hydrolysis or low stomach pH. In some embodiments, an agent of the present invention can be formulated for release in the small intestine, for example, lectins, can be used to target agents to the gastrointestinal tract, and particularly can recognize and bind to villus and crypt cells in the intestines (see, e.g., Handbook of plant lectins: properties and biomedical applications, Els J. M. Van Damme, et al., eds., John Wiley and Sons, 1998).

The therapeutically effective compositions containing the agents of the present invention are administered to a subject, in accordance with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. In some embodiments, a radioprotective agent comprises a radioprotective agent. In some embodiments, an agent (e.g., radioprotective agent) or composition of the present invention is administered as an enema. Administration of the agents and compositions (e.g., radioprotective agents and compositions thereof) as an enema may be advantageous, for example, administration as an enema facilitates local, rather than systemic, delivery to the targeted area (GI system) where the agent exerts its biological effects, as well as avoids factors which result in diminished or insufficient absorption of a drug and its ultimate transport to its biological target resulting from elimination and metabolism of drugs that are administered systemically (e.g., oral administration). Accordingly, administration of the agents and compositions of the present invention as an enema may result in an enhanced therapeutic effect while minimizing side effects. In some embodiments, a method of treating or preventing harm resulting from exposure to ionizing radiation comprises administering an effective amount of agent or composition of the present invention (e.g., a radioprotective agent, e.g., sirolimus or a derivative or analog thereof) to a patient in need thereof, wherein the agent or composition is administered as an enema.

Other therapeutic regimens may be combined with the administration of the agents of the present invention. The combined administration includes co-administration, using separate formulations or a single pharmaceutical formulation, and consecutive administration in either order, wherein preferably there is a time period while both (or all) active agents simultaneously exert their biological activities. Preferably such combined therapy results in a synergistic therapeutic effect. In some embodiments, a composition of the present invention is administered in combination with a therapy selected from the group consisting of chemotherapy, radiotherapy, proton therapy, surgery, and combinations thereof.

The composition can include any number of additional active ingredients which can act in concert to provide a therapeutic effect, (e.g., a synergistic therapeutic effect), such as a chemotherapeutic agent, a radiotherapeutic agent, an insulin inhibitor, an appetite suppressant, a nutritional supplement (e.g. vitamins), an antioxidant, and combinations thereof.

The present invention also relates to a method of minimizing the risk of exposure to an ionizing radiation source, such method comprising administering to an individual an effective amount of a calorie restriction mimetic that inhibits the level and/or activity of mTORC1 (e.g., rapamycin or a derivative or analog thereof), and/or a calorie restriction mimetic that increases the level and/or activity of Bst-1 or a product of Bst-1 (e.g., cADPR). The calorie restriction mimetic can be used to minimize the risk of exposure to any ionizing radiation source, including any source of accidental or incidental ionizing radiation, such as radioactive material, a nuclear power plant, a nuclear weapon, or cosmic radiation, to name but a few. In some embodiments, the ionizing radiation source is cosmic radiation in outer space. In some embodiments, the cosmic radiation is cosmic radiation that has not penetrated the Earth's atmosphere. In some embodiments, the cosmic radiation has penetrated at least a portion of the Earth's atmosphere. In some embodiments, the calorie restriction mimetic can be used to minimize the risk of exposure to cosmic radiation in the ionosphere. In some embodiments, the calorie restriction mimetic can be used to minimize the risk of exposure to cosmic radiation in the thermosphere. In some embodiments, the calorie restriction mimetic can be used to minimize the risk of exposure to cosmic radiation in the mesosphere. In some embodiments, the calorie restriction mimetic can be used to minimize the risk of exposure to cosmic radiation in the stratosphere. In some embodiments, the calorie restriction mimetic can be used to minimize the risk of exposure to cosmic radiation in the troposphere. In some embodiments, the calorie restriction mimetic can be used to minimize the risk of exposure to cosmic radiation at sea level. The calorie restriction mimetic can also be administered to an individual that is being administered radiotherapy, or an individual that is about to be administered radiotherapy, to minimize the risk of exposure to the ionizing radiation administered during the radiotherapy. In some instances, a method of minimizing the risk of exposure to an ionizing radiation source comprises placing the individual on a CR regimen for a pre-determined period of time prior to exposure to the ionizing radiation source. In some embodiments, the pre-determined period of time for placing an individual on a CR regimen prior to exposure to an ionizing radiation source can range from hours to weeks (e.g., from about 1 hour, about 2 hours, about 3 hours, about 4 hours, about 5 hours, about 6 hours, about 12 hours, about 1 day, about 2 days, about 3 days, about 4 days, about 5 days, about 6 days, about 1 week, about a week and half, about two weeks, about three weeks, about a month, and any interval therebetween). In certain instances, the method of minimizing the risk of exposure to an ionizing radiation source comprises placing the individual on a CR regimen prior to exposure to an ionizing radiation source, and administering to the individual an effective amount of a calorie restriction mimetic.

It should be appreciated that any of the circumstances noted above for which a calorie restriction mimetic can be used to minimize the risk of exposure to a source of ionizing radiation can also be useful in a method of treating an individual exposed to the same source of ionizing radiation.

In certain embodiments, the present invention contemplates methods of treating an individual exposed to ionizing radiation, such methods comprising administering to the individual an effective amount of a calorie restriction mimetic (e.g., an agent that inhibits the level and/or activity of mTORC1 or an agent that increases the level and/or activity of Bst-1 or a product of Bst-1). In addition to, or in lieu of, administration of the calorie restriction mimetic, the individual exposed to ionizing radiation can be placed on a CR regimen.

In other embodiments, the present invention relates to a method of increasing tolerance to ionizing radiation in an individual, such method comprising administering to the individual an effective amount of a calorie restriction mimetic, wherein the calorie restriction mimetic increases the threshold dose of lethal ionizing radiation to above 8 Gy (e.g., the threshold dose of lethal ionizing radiation is increased to about 9 Gy, about 10 Gy, about 11 Gy, about 12 Gy, about 13 Gy, about 14 Gy, and up to about 15 Gy). In some embodiments, the calorie restriction mimetic increases a threshold dose of lethal ionizing radiation in a human mammal. In some embodiments, the calorie restriction mimetic increases a threshold dose of lethal ionizing radiation in a non-human mammal.

In still other embodiments, the present invention relates to methods of treating cancer, such methods comprising administering an effective amount of ionizing radiation to a patient in need thereof, and administering to the patient an effective amount of a calorie restriction mimetic (e.g., sirolimus or a derivative thereof or analog thereof, Bst-1 or a Bst-1 mimetic, cADPR or a cADPR mimetic, CD38 or a CD38 mimetic, etc.). One of ordinary skill in the art should appreciate that the calorie restriction mimetic can be employed in the course of treating any cancer that involves radiotherapy. In some instances, the method of treatment can include placing the patient on a CR regimen prior to, or during the course of, administering the ionizing radiation. In some instances, the method of treatment can also include administering to the patient an appetite suppressant, an antioxidant, an insulin inhibitor, a chemotherapeutic agent, surgery, and combinations thereof. The calorie restriction mimetic can be administered prior, during, or after administering the ionizing radiation to the patient. The present invention contemplates the use of any agent that is capable of reducing insulin levels in a patient (e.g., an insulin receptor antagonist).

In another aspect, the present invention includes a method for expanding and/or activating a population of intestinal stem cells, such method comprising contacting a population of Paneth cells or Paneth-like cells that is in cellular communication with the intestinal stem cells with an effective amount of an agent that inhibits the levels and or activity of mTORC1 in the Paneth cells or Paneth-like cells. Examples of suitable agents for inhibiting the levels and or activity of mTORC1 are described in further detail supra. For example, as noted above, in some embodiments, the agent comprises sirolimus or a derivative or analog thereof. Methods of screening for agents that are capable of inhibiting the level and/or activity of mTORC1 are described in further detail infra. In some embodiments, the method for expanding the ISCs is performed in vitro. In some embodiments, method for expanding the ISCs is performed ex vivo. It should be appreciated that the ex vivo methods and compositions of the present invention for generating ISCs and intestinal tissues, as well as grafting those generated cells and tissues, can be used for any condition that would benefit from restoration and/or augmentation of intestinal function. In some embodiments, the method for expanding ISCs can be used to maintain intestinal stem cells for a patient that may be preserved and eventually engrafted into an atrophic or damaged intestine or used ex vivo in the construction of an artificial organ which may subsequently be implanted into a subject. In some embodiments, the ex vivo methods of the present invention can be used to study intestinal transport, metabolism (of drugs, etc.) and drug design to enhance absorption and bioavailability.

In some embodiments, composition for ex vivo expansion of intestinal stem cells is disclosed, such composition comprising a population of intestinal stem cells and a calorie restriction mimetic. In some embodiments, a composition for ex vivo expansion of intestinal stem cells includes Paneth cells. In some embodiments, a composition for ex vivo expansion of intestinal stem cells includes Paneth-like cells. It should be appreciated that intestinal stem cells and/or Paneth or Paneth-like cells for use in the ex vivo expansion compositions and methods of the present invention can be autologous or non-autologous. Intestinal stem cells and/or Paneth cells are found within the crypts of the mucosa of the intestine, e.g., small intestines or colon. Such cells can be isolated and/or extracted according to routine methods (e.g., non-limiting examples of obtaining intestinal stem cells and/or Paneth cells include, surgery and biopsy, for example). In some instances, it may be preferable to utilize intact crypts, organoid bodies, intestinal stem cells and/or Paneth cells that have been removed from a patient during a small-intestine (or small-bowel) biopsy as part of diagnosis of a disease of the intestinal mucosa. In such instances, the cells thus obtained can be banked and maintained for subsequent use in the ex vivo expansion compositions and methods of the present invention. In some instances, the ISCs can be obtained from pluripotent stem cells (PSCs) or embryonic stem cells (ESCs) that have been induced or directed to differentiate into ISCs, for example, by a process to direct the differentiation of human PSCs into intestinal tissue in vitro using growth factors to simulate embryonic intestinal development (Wells et al. Nature. 470 (7332): 105-109, 2011). This process of directed differentiation can be used to produce ISCs, for example, from fibroblasts obtained from a skin biopsy of the patient. In some embodiments, a method for expanding ISCs of a patient comprises: (a) obtaining a pluripotent stem cell non-invasively from a patient (e.g., skin biopsy of fibroblast cells); (b) directing differentiation of the pluripotent stem cells obtained non-invasively in step (a) by manipulating the pluripotent stem cells with one or more appropriate growth factors, wherein the pluripotent stem cells differentiate into intestinal tissue; and (c) contacting a population of Paneth cells or Paneth-like cells in the intestinal tissue generated in step (b) with an effective amount of an agent that inhibits the level and/or activity of mTORC1, thereby activating and expanding the ISCs of the patient. In some embodiments, a composition for ex vivo expansion of intestinal stem cells includes a culture medium. Suitable culture mediums are apparent to those skilled in the art (see, for example, materials and methods below). In some embodiments, a pluripotent cell is an induced pluripotent stem (iPS) cell that has been derived in vitro from a non-pluripotent somatic cell such as a skin cell, fibroblast or myoblast (or is descended from a cell that has been so derived). An iPS cell can be derived using a variety of different protocols. In some embodiments an iPS cell is derived by causing a somatic cell to express at least one, two, or three of the pluripotency factors Oct4, Nanog, and Sox2. Optionally the cells are caused to overexpress c-Myc. In some embodiments an iPS cell is derived by causing a somatic cell to express at least one, two, three, or four of the transcription factors Oct4, Nanog, Sox2, and Lin28. In some embodiments viral transduction is used to cause a cell to express a reprogramming factor. In some embodiments an iPS cell is generated without use of retroviruses or other integrating viruses and/or without inserting exogenous DNA into the genome of the cell. A variety of techniques, e.g., involving small molecules and/or protein transduction and/or non-integrating vectors and/or introducing translatable RNA molecules (e.g., encoding one or more pluripotency factor(s)) into cells can employed in the generation of iPS cells in various embodiments. See, e.g., PCT/US2008/004516 (WO 2008/124133) REPROGRAMMING OF SOMATIC CELLS); Lyssiotis, Calif., Proc Natl Acad Sci USA. 2009 Jun. 2; 106(22):8912-7. Epub 2009 May 15; Carey B W, Proc Natl Acad Sci USA. 2009 Jan. 6; 106(1):157-62. Epub 2008 Dec. 24, and references cited in any of the foregoing, for additional information regarding iPS cells. Use of any of the compositions and methods described in PCT/US2009/057692, "Compositions and Methods for Enhancing Cell Reprogramming", filed 21 Sep. 2009, is contemplated.

In another aspect, the present invention includes a method for identifying an agent that is capable of stimulating the proliferation of and/or self-renewal of intestinal stem cells. In some embodiments, a method for identifying an agent that is capable of stimulating the proliferation of Paneth cells and/or stimulating the proliferation and/or self-renewal of intestinal stem cells comprises: (a) contacting a cell culture comprising small intestinal crypt cells with a candidate agent; and (b) assaying for an increase in the amount of an intestinal stem cell marker in the cell culture, wherein an increase in the amount of the intestinal stem cell marker in the cell culture is indicative of the proliferation and/or self-renewal of ISCs in the cell culture, and indicates that the candidate agent is an agent that is capable of stimulating the proliferation of Paneth cells and/or stimulating the proliferation and/or self-renewal of ISCs. In some embodiments, an intestinal stem cell marker comprises Olfacomedin-4 (Olmf4). In such embodiments, step (b) of the method comprises assaying for an increase in Olmf4 in the cell culture, wherein increase in the level of Olmf4 in the cell culture is indicative of the proliferation and self-renewal of ISCs in the cell culture.

In some embodiments, a method for identifying an agent that is capable of stimulating the proliferation of Paneth cells comprises: (a) contacting a cell culture comprising intestinal crypts, e.g., small intestinal crypts with a candidate agent; and (b) assaying Lgr5+ ISCs in the cell culture for an increase in the amount of organoid bodies formed, wherein an increase in the amount of organoid bodies formed by the Lgr5+ ISCs is indicative of the proliferation of Paneth cells in the culture.

In some embodiments, the present invention includes a method for identifying an agent that inhibits the level and/or activity of mTORC1. A non-limiting example of a method for identifying an agent that inhibits the level and/or activity of mTORC1 includes performing an mTORC1 kinase assay. Certain mTORC1 kinase assays measure the ability of mTORC1 to phosphorylate one of its targets (e.g., S6 ribosomal protein, which is a marker of mTORC1 activity). mTORC1 kinase assays are well known in the art. Agents identified with the mTORC1 assay that inhibit the ability of mTORC1 to phosphorylate one of its targets are candidate agents for inhibiting the level and/or activity of mTORC1. In some embodiments, a high-throughput method for identifying one or more agents that inhibit the level and/or activity of mTORC1 is disclosed. A non-limiting example of such a high-throughput method is disclosed in published PCT Application No. WO 2010/044885, the entirety of which is incorporated by reference herein. Briefly, such method includes: (a) introducing purified mTORC1, mTORC1 substrate, ATP, and one or more test agents into each of a plurality of reaction vessels; (b) incubating the vessels under conditions suitable for and for a time sufficient to allow phosphorylation of the mTORC1 substrate; and (c) assaying for the presence and/or amount of phosphorylated mTORC1 substrate, wherein a reduction in the presence and/or amount of phosphorylated mTORC1 substrate as compared to controls in which the test agent is not present indicates that the one or more test agents is capable of inhibiting the level and/or activity of mTORC1.

In another aspect, the present invention includes a method for identifying a radioprotective agent. In some embodiments, Paneth cells, Paneth-like cells and/or intestinal stem cells, which may be capable of proliferating and self-renewing, are exposed to ionizing radiation and are used in a screen to identify compounds that serve as radioprotective agents and can be used to stimulate the proliferation Paneth cells, Paneth-like cells, and/or stimulate the proliferation and/or self-renewal of intestinal stem cells. For example, in some embodiments a method for testing the ability of a compound to stimulate the proliferation of Paneth cells, Paneth-like cells, and/or stimulate the proliferation of intestinal stem cells, comprises (a) contacting a population of Paneth cells or Paneth-like cells, and/or intestinal stem cells with the compound wherein the population of Paneth cells, Paneth-like cells, and/or intestinal stem cells has been exposed to ionizing radiation; (b) detecting the survival, proliferation, and/or self-renewal of the Paneth cells, Paneth-like cells, and/or intestinal stem cells in the presence of the compound; and (c) comparing the survival, proliferation, and/or self-renewal of the Paneth cells, Paneth-like cells, and/or intestinal stem cells in the presence of the compound to a control or reference compound which is not capable of stimulating the proliferation of Paneth cells, Paneth-like cells, and/or stimulating the proliferation of intestinal stem cells, wherein the ability of the compound to promote increased survival, proliferation, and/or self-renewal of the Paneth cells, Paneth-like cells, and/or intestinal stem cells as compared to the control or reference compound is indicative that the compound is capable of stimulating the proliferation of Paneth cells, Paneth-like cells, and/or stimulating the proliferation of intestinal stem cells. Methods for evaluating survival, proliferation, and/or self-renewal of the cells are routine in the art, and include qualitative and quantitative methods, for example, flow cytometry, as described in the materials and methods infra.

In some embodiments, the present invention includes a high-throughput method for identifying agents that enhance the production of cADPR. A non-limiting example of a high-throughput method for identifying agents that enhance the production of cADPR is a cycling assay (Graeff and Lee. *Biochem. J.* 361, 379-384, 2002). Briefly, ADP-ribosyl cyclase usually catalyzes the synthesis of cADPR from NAD+, however, the reaction is reversible in the presence of high concentrations of nicotinamide, which results in the production of NAD+ from cADPR in a stoichiometric fashion. NAD+ from the reaction can be coupled to a cycling assay that involves alcohol dehydrogenase and diaphorase. Every time NAD+ cycles through the coupled reactions, a fluorescent resorufin molecule is produced. The reaction can cycle for hours amplifying cADPR more than a thousand-fold, and allowing nanomolar concentrations of cADPR to be measured. One of skill in the art can readily adapt the cycling assay thus described to identify agents that are capable of synthesizing cADPR. Another non-limiting example of a high-throughput assay for identifying agents that enhance the production of cADPR is a fluorometric assay (Graeff and Lee. *Comb Chem high Throughput Screen.* 6 (4): 367-78, 2003). Briefly, a cADPR fluorometric assay relies on coupled-enzyme amplification and can easily detect nanomolar concentrations of cADPR using a multi-well format using reagents that are commercially available. The enzyme assay particularly uses an NAD analog, nicotinamide guanine dinucleotide, which is not fluorescent but can be cyclized by the enzymes to a fluorescent analog of cADPR, cyclic GDP-ribose, as well as other NAD utilizing enzymes that are incapable of catalyzing cyclization of the analog and thus do not interfere with the reaction. Detection of cADPR levels for use in screening methods of the present invention can also be achieved by radioimmunoassay, detection of cADPR using antibodies (e.g., ELISA), and bioassays. (Lee, Hon Cheug (ed.) "Cyclic ADP-Ribose and NAADP, Structures, Metabolism, and Functions", Kluwer Academic Publishers, 2002).

In some embodiments, the present invention includes a method for identifying an mimetic of Bst-1 or CD38. Bst-1 and CD38 are enzymes that involved in the synthesis of cADPR using NAD+ as a substrate. In some embodiments, a method for identifying an mimetic of Bst-1 or CD38 comprises: (a) incubating ADPR and NAD+ in a reaction mixture under conditions suitable for synthesis of cADPR to occur; and (b) adding a test agent to the reaction mixture, wherein increased production of cADPR in the reaction mixture indicates that the test agent may be a potential mimetic of Bst-1 or CD38. In some embodiments, the method further comprises (c) evaluating the potential mimetic identified in step (b) for its ability to outperform Bst-1 or CD38 in synthesizing cADPR, for example, by measuring the amount of cADPR produced under similar conditions in comparison to Bst-1 or CD38. In some embodiments, the method further comprises (c) testing the effect of the potential mimetic on proliferation and/or self-renewal of ISCs, optionally in the presence of Paneth cells, ex vivo or in vivo. Suitable methods for measuring the amount of cADPR are apparent to those skilled in the art, for example, as noted above, cADPR cycling assays and fluormetric assays.

In some embodiments, the present invention includes a method for identifying an agent useful for enhancing the proliferation and/or self-renewal of ISCs, such method comprising: (a) incubating ADPR and NAD+ in a reaction mixture under conditions suitable for synthesis of cADPR to occur; and (b) adding a test agent to the reaction mixture, wherein increased production of cADPR in the reaction mixture, wherein increased production of cADPR in the reaction mixture indicates that the test agent may be a potential mimetic of Bst-1 or CD38 which may be useful for enhancing the proliferation and/or self-renewal of ISCs. In some embodiments, the method further comprises (c) evaluating the potential mimetic identified in step (b) for its ability to outperform Bst-1 or CD38 in synthesizing cADPR, for example, by measuring the amount of cADPR produced under similar conditions in comparison to Bst-1 or CD38. In some embodiments, the method further comprises (c) testing the effect of the potential mimetic on proliferation and/or self-renewal of ISCs, optionally in the present of Paneth cells, ex vivo or in vivo. In some embodiments, the method optionally comprises (d) administering the potential mimetic to a subject. As used here, "subject" can refer to a human or non-human mammal. In some embodiments, the method optionally comprises (e) detecting expression of an ISC marker in the subject (e.g., increased expression of Olmf4+ in ISCs and/or expression of Lgr5+ ISCs), wherein the expression of an ISC marker in the subject is indicative that the potential mimetic enhanced the proliferation and/or self-renewal of ISCs in the subject. In some embodiments, the method optionally comprises (e) detecting the formation of organoid bodies formed in Lgr5+ ISCs in small intestinal crypt cells of the subject, wherein, wherein an increase in the amount of organoid bodies formed by the Lgr5+ ISCs is indicative of the proliferation of ISCs in the subject.

A wide variety of test agents can be used in the methods. For example, a test agent can be a small molecule, polypeptide, peptide, nucleic acid, oligonucleotide, lipid, carbohydrate, or hybrid molecule. Compounds can be obtained from natural sources or produced synthetically. Compounds can be at least partially pure or may be present in extracts or other types of mixtures. Extracts or fractions thereof can be produced from, e.g., plants, animals, microorganisms, marine organisms, fermentation broths (e.g., soil, bacterial or fungal fermentation broths), etc. In some embodiments, a compound collection ("library") is tested. The library may comprise, e.g., between 100 and 500,000 compounds, or more. Compounds are often arrayed in multiwell plates. They can be dissolved in a solvent (e.g., DMSO) or provided in dry form, e.g., as a powder or solid. Collections of synthetic, semi-synthetic, and/or naturally occurring compounds can be tested. Compound libraries can comprise structurally related, structurally diverse, or structurally unrelated compounds. Compounds may be artificial (having a structure invented by man and not found in nature) or naturally occurring. In some embodiments, a library comprises at least some compounds that have been identified as "hits" or "leads" in other drug discovery programs and/or derivatives thereof. A compound library can comprise natural products and/or compounds generated using non-directed or directed synthetic organic chemistry. Often a compound library is a small molecule library. Other libraries of interest include peptide or peptoid libraries, cDNA libraries, and oligonucleotide libraries. A library can be focused (e.g., composed primarily of compounds having the same core structure, derived from the same precursor, or having at least one biochemical activity in common).

Compound libraries are available from a number of commercial vendors such as Tocris BioScience, Nanosyn, BioFocus, and from government entities. For example, the Molecular Libraries Small Molecule Repository (MLSMR), a component of the U.S. National Institutes of Health (NIH) Molecular Libraries Program is designed to identify, acquire, maintain, and distribute a collection of >300,000 chemically diverse compounds with known and unknown biological activities for use, e.g., in high-throughput screening (HTS) assays (see https://mli.nih.gov/mli/). The NIH Clinical Collection (NCC) is a plated array of approximately 450 small molecules that have a history of use in human clinical trials. These compounds are highly drug-like with known safety profiles. The NCC collection is arrayed in six 96-well plates. 50 µl of each compound is supplied, as an approximately 10 mM solution in 100% DMSO. In some embodiments, a collection of compounds comprising "approved human drugs" is tested. An "approved human drug" is a compound that has been approved for use in treating humans by a government regulatory agency such as the US Food and Drug Administration, European Medicines Evaluation Agency, or a similar agency responsible for evaluating at least the safety of therapeutic agents prior to allowing them to be marketed. The test agent may be, e.g., an antineoplastic, antibacterial, antiviral, antifungal, antiprotozoal, antiparasitic, antidepressant, antipsychotic, anesthetic, antianginal, antihypertensive, antiarrhythmic, antiinflammatory, analgesic, antithrombotic, antiemetic, immunomodulator, antidiabetic, lipid- or cholesterol-lowering (e.g., statin), anticonvulsant, anticoagulant, antianxiety, hypnotic (sleep-inducing), hormonal, or anti-hormonal drug, etc. In some embodiments, a compound is one that has undergone at least some preclinical or clinical development or has been determined or predicted to have "drug-like" properties. For example, the test agent may have completed a Phase I trial or at least a preclinical study in non-human animals and shown evidence of safety and tolerability. In some embodiments, a test agent is substantially non-toxic to cells of an organism to which the compound may be administered or cells in which the compound may be tested, at the concentration to be used or, in some embodiments, at concentrations up to 10-fold, 100-fold, or 1,000-fold higher than the concentration to be used. For example, there may be no statistically significant adverse effect on cell viability and/or proliferation, or the reduction in viability or proliferation can be no more than 1%, 5%, or 10% in various embodiments.

In various embodiments of any aspect herein pertaining to screening methods (e.g., methods of identifying agents), the screen may be performed using a single test agent or multiple test agents in a given reaction vessel. In various embodiments the number of reaction vessels and/or test agents is at least 10; 100; 1000; 10,000; 100,000, or more. In some embodiments of any aspect herein pertaining at least in part to screening methods (e.g., methods of identifying agents) a high throughput screen (HTS) is performed. High throughput screens often involve testing large numbers of test agents with high efficiency, e.g., in parallel. For example, tens or hundreds of thousands of agents may be routinely screened in short periods of time, e.g., hours to days. Such screening is often performed in multiwell plates (sometimes referred to as microwell or microtiter plates or microplates) containing, e.g., 96, 384, 1536, 3456, or more wells or other vessels in which multiple physically separated depressions, wells, cavities, or areas (collectively "wells") are present in or on a substrate. Different test agent(s) may be present in or added to the different wells. It will be understood that some wells may be empty, may comprise replicates, or may contain control agents or vehicle. High throughput screens may involve use of automation, e.g., for liquid handling, imaging, and/or data acquisition or processing, etc. In some embodiments an integrated robot system comprising one or more robots transports assay-microplates from station to station for, e.g., addition, mixing, and/or incubation of assay constituents (e.g., test agent, target, substrate) and, in some embodiments, readout or detection. A HTS system may prepare, incubate, and analyze many plates simultaneously. Certain general principles and techniques that may be applied in embodiments of a HTS are described in Macarrón R & Hertzberg R P. Design and implementation of high-throughput screening assays. Methods Mol Biol., 565:1-32, 2009 and/or An W F & Tolliday N J, Introduction: cell-based assays for high-throughput screening. Methods Mol Biol. 486:1-12, 2009, and/or references in either of these. Exemplary methods are also disclosed in High Throughput Screening: Methods and Protocols (Methods in Molecular Biology) by William P. Janzen (2002) and High-Throughput Screening in Drug Discovery (Methods and Principles in Medicinal Chemistry) (2006) by Jorg Hüser. Test agent(s) showing an activity of interest (sometimes termed "hits") may be retested and/or, optionally (e.g., depending at least in part on results of retesting) selected for further testing, development, or use. In some embodiments one or more structural analogs of a hit is synthesized. Such analogs may, for example, comprise substitution of one or more functional groups or heteroatoms present in the hit by a different functional group or heteroatom or substituting a heteroatom or functional group present in place of a hydrogen in the hit, etc. In some embodiments one or more such analog(s) are then tested for a property or activity of interest (e.g., ability to inhibit the level and/or activity of mTORC1, ability to increase the level and/or activity of Bst-1; ability to increase the level and/or activity of cADPR, ability to increase the level and/or activity of CD38, or the ability to mimic the biological function of Bst-1, cADPR, and/or CD38.).

Positive and/or negative controls may be used in any of the screens. An appropriate positive or negative control can be selected based at least in part on the assay. A negative control may be to perform the assay in the absence of a test agent.

In some embodiments, information derived from sequence analysis, mutational analysis, and/or structural analysis is used in the identification of a modulator, e.g., an inhibitor of mTORC1 or a mimetic of Bst-1, cADPR, or CD38. For example, in some embodiments a structure (e.g., a two-dimensional or three-dimensional structure) of a target, e.g., a TF, generated at least in part using, e.g., nuclear magnetic resonance, homology modeling, and/or X-ray crystallography is used. In some embodiments a structure obtained with a ligand (e.g., an inhibitor) bound to the target may be used. In some embodiments a computer-aided computational approach sometimes referred to as "virtual screening" is used in the identification of candidate modulators. Structures of compounds, e.g., small molecules may be screened for ability to bind to a region (e.g., a "pocket") accessible to the compound. The region may be any region accessible to the compound, e.g., a concave region on the surface or a cleft or a region involved in dimerization. A variety of docking and pharmacophore-based algorithms are known in the art, and computer programs implementing such algorithms are available. Commonly used programs include Gold, Dock, Glide, FlexX, Fred, and LigandFit (including the most recent releases thereof). See, e.g., Ghosh, S., et al., Current Opinion in Chemical Biology, 10(3): 194-2-2, 2006; McInnes C., Current Opinion in Chemical Biology; 11(5): 494-502, 2007, and references in either of the foregoing articles, which are incorporated herein by reference. In some embodiments a virtual screening algorithm may involve two major phases: searching (also called "docking") and scoring. During the first phase, the program automatically generates a set of candidate complexes of two molecules (test compound and target molecule) and determines the energy of interaction of the candidate complexes. The scoring phase assigns scores to the candidate complexes and selects a structure that displays favorable interactions based at least in part on the energy. To perform virtual screening, this process may be repeated with a large number of test compounds to identify those that, for example, display the most favorable interactions with the target. In some embodiments, low-energy binding modes of a small molecule within an active site or possible active site or other target region are identified. In some embodiments a compound capable of docking at a site where mutations are known to inhibit activity of the target is identified. Variations may include the use of rigid or flexible docking algorithms and/or including the potential binding of water molecules. In some embodiments the three-dimensional structure of an enzyme's active site may be used to identify potential inhibitors, Agent(s) that have the potential to bind in or near an active site may be identified. These predictions may then be tested using the actual compound. A new inhibitor thus identified may then be used to obtain a structure of the enzyme in an inhibitor/enzyme complex to show how the molecule is binding to the active site. Further changes may be made to the inhibitor, e.g., to try to improve binding. This cycle may be repeated until an inhibitor of sufficient predicted or actual potency (e.g., a desired potency for therapeutic purposes) is identified. Numerous small molecule structures are available and can be used for virtual screening. A collection of compound structures may sometimes referred to as a "virtual library". For example, ZINC is a publicly available database containing structures of millions of commercially available compounds that can be used for virtual screening (http://zinc.docking.org/; Shoichet, J. Chem. Inf. Model., 45(1):177-82, 2005). A database containing about 250,000 small molecule structures is available on the National Cancer Institute (U.S.) website (at http://129.43.27.140/ncidb2/). In some embodiments multiple small molecules may be screened, e.g., up to 50,000; 100,000; 250,000; 500,000, or up to 1 million, 2 million, 5 million, 10 million, or more. Compounds can be scored and, optionally, ranked by their potential to bind to a target, Compounds identified in virtual screens can be tested in cell-free or cell-based assays or in animal models to confirm their ability to inhibit activity of a target molecule, their ability to activate a target molecule, and/or to assess their biological and/or pharmacological activity. Computational approaches may be used to predict one or more physicochemical, pharmacokinetic and/or pharmacodynamic properties of compounds identified in a physical or virtual screen. Such information may be used, e.g., to select one or more hits for, e.g., further testing, development, or use. For example, small molecules having characteristics typical of "drug-like" molecules may be selected and/or small molecules having one or more undesired characteristics may be avoided.

In some aspects of any screening and/or characterization methods, test agents are contacted with test cells (and optionally control cells) or used in cell-free assays at a predetermined concentration. In some embodiment the concentration is about up to 1 nM. In some embodiments the concentration is between about 1 nM and about 100 nM. In some embodiments the concentration is between about 100 nM and about 10 µM. In some embodiments the concentration is at or above 10 µM, e.g., between 10 µM and 100 µM. Following incubation for an appropriate time, optionally a predetermined time, the effect of compounds or composition on a parameter of interest in the test cells is determined by an appropriate method known to one of ordinary skill in the art, e.g., as described herein. Cells can be contacted with compounds for various periods of time. In certain embodiments cells are contacted for between 12 hours and 20 days, e.g., for between 1 and 10 days, for between 2 and 5 days, or any intervening range or particular value. Cells can be contacted transiently or continuously. If desired, the compound can be removed prior to assessing the effect on the cells.

One skilled in the art readily appreciates that the present invention is well adapted to carry out the objects and obtain the ends and advantages mentioned, as well as those inherent therein. The details of the description and the examples herein are representative of certain embodiments, are exemplary, and are not intended as limitations on the scope of the invention. Modifications therein and other uses will occur to those skilled in the art. These modifications are encompassed within the spirit of the invention. It will be readily apparent to a person skilled in the art that varying substitutions and modifications may be made to the invention disclosed herein without departing from the scope and spirit of the invention.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention provides all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. It is contemplated that all embodiments described herein are applicable to all different aspects of the invention where appropriate. It is also contemplated that any of the embodiments or aspects can be freely combined with one or more other such embodiments or aspects whenever appropriate. Where elements are presented as lists, e.g., in Markush group or similar format, it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. For example, any one or more nucleic acids, polypeptides, cells, species or types of organism, disorders, subjects, or, combinations thereof, can be excluded.

Where the claims or description relate to a composition of matter, e.g., a nucleic acid, polypeptide, cell, or non-human transgenic animal, it is to be understood that methods of making or using the composition of matter according to any of the methods disclosed herein, and methods of using the composition of matter for any of the purposes disclosed herein are aspects of the invention, unless otherwise indicated or unless it would be evident to one of ordinary skill in the art that a contradiction or inconsistency would arise. Where the claims or description relate to a method, e.g., it is to be understood that methods of making compositions useful for performing the method, and products produced according to the method, are aspects of the invention, unless otherwise indicated or unless it would be evident to one of ordinary skill in the art that a contradiction or inconsistency would arise.

Where ranges are given herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. It is also understood that where a series of numerical values is stated herein, the invention includes embodiments that relate analogously to any intervening value or range defined by any two values in the series, and that the lowest value may be taken as a minimum and the greatest value may be taken as a maximum. Numerical values, as used herein, include values expressed as percentages. For any embodiment of the invention in which a numerical value is prefaced by "about" or "approximately", the invention includes an embodiment in which the exact value is recited. For any embodiment of the invention in which a numerical value is not prefaced by "about" or "approximately", the invention includes an embodiment in which the value is prefaced by "about" or "approximately". "Approximately" or "about" generally includes numbers that fall within a range of 1% or in some embodiments within a range of 5% of a number or in some embodiments within a range of 10% of a number in either direction (greater than or less than the number) unless otherwise stated or otherwise evident from the context (except where such number would impermissibly exceed 100% of a possible value). It should be understood that, unless clearly indicated to the contrary, in any methods claimed herein that include more than one act, the order of the acts of the method is not necessarily limited to the order in which the acts of the method are recited, but the invention includes embodiments in which the order is so limited. It should also be understood that unless otherwise indicated or evident from the context, any product or composition described herein may be considered "isolated".

EXAMPLES

Example 1 mTORC1 Signaling in the Paneth Cell Niche Regulates Intestinal Stem Cell Function in Response to Calorie Intake Mammalian tissue-specific stem cells are capable of maintaining tissue homeostasis by undergoing either self-renewing divisions that generate more stem cells or a series of divisions that give rise to the various differentiated cell types characteristic of the tissue[1]. These stem cells often require cues from their microenvironment or "niche" for their maintenance and function. In the *Drospholia* mid-gut, for example, intestinal stem cells, which are the only mitotic cells of the fly mid-gut, control intestinal remodeling in response to fasting and refeeding by an insulin signal emanating from the niche[4]. Calorie restriction (CR), an intervention in which caloric intake is reduced while maintaining adequate nutrition, promotes longevity in diverse organisms in part by enhancing the function of stem and progenitors cells[2,5]. In mice, CR promotes the generation of new neurons from neural progenitors and prevents the decline in hematopoietic stem cell numbers and function in certain strains of mice with age[2,6-9]. These findings raise the question of how CR mediates these effects, and whether CR directly affects stem cell function or whether the mammalian stem cell niche orchestrates these changes.

We chose to interrogate this question in the rapidly renewing mammalian small intestine. In response to fasting and re-feeding the intestine undergoes structural alterations such as changes in villi length, crypt depth, and cell turnover, suggesting that organismal physiology may modify intestinal progenitor function[10,11]. Recent studies have begun to define the identity of intestinal stem cells as well as their interaction with their Paneth cell niche in the mammalian intestine[3,12-15]. Although no single marker identifies the entire ISC pool, Lgr5 is expressed by a majority of ISCs throughout the intestinal tract[15,16]. These Lgr5+ ISCs (aka crypt base columnar cells or CBCs) can self-renew and differentiate for the life of the organism, and they reside at the base of intestinal crypts sandwiched between Paneth cells[15,17]. Loss of Paneth cells in vivo leads to reduced numbers of Lgr5+ ISCs, while the addition of Paneth cells to in vitro cultures dramatically increases the potential of Lgr5+ ISCs to form multipotent, self-renewing organoid bodies reminiscent of "mini-intestines"[3]. Thus, Paneth cells constitute a critical component of the stem cell niche both in vivo and in vitro[3,15]. Although Paneth cells provide key signals that allow for the maintenance of Lgr5+ ISCs, it is unknown whether Paneth cells couple organismal physiology with stem cell function.

Figure 5A:
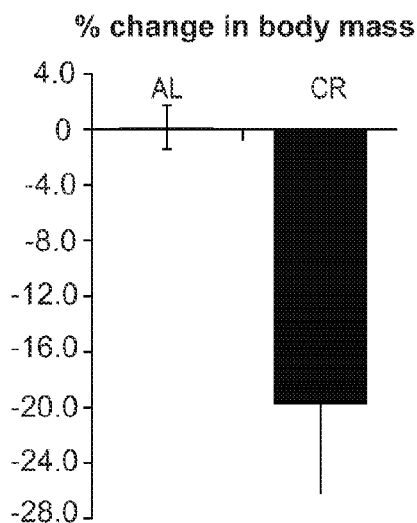
FIGS. 5a-k. Calorie restriction increases the proliferation of ISCs but reduces the proliferation and migration of differentiated progenitors into the villi. (a-f) Mice on calorie restriction (CR) lost on average 20% of their mass (a, n=34-39), had reduced small intestinal mass (b, 1.8±0.4 vs 1.4±0.2 g), shorter villi (f, 477±25 vs 423±35 µm, n=3-5), and fewer mature villous enterocytes (c, 119±2 vs 105±4, n=3). Representative histology of the proximal jejunum in CR mice showed a small reduction in villi length (n=4-5). The proximal jejunum was defined as the length between 6 to 9 cm as measured from the pylorus (distal portion of the stomach). CR did not change small intestinal length (c, n=3) or the density of crypts in the jejunum (d, n=3). g-h. CR enhanced the proliferation of $Lgr5^{hi}$ ISCs as assessed 4 hours after a pulse of BrdU assessed in cytospun preparations (h) and histology (g, n=3). Representative crypts (g) demonstrate increased BrdU positivity in crypt base columnar cells (CBCs, cells adjacent to Paneth cells at the bottom of crypts and designated by arrowheads). i-l. Cell migration was determined by administering a single dose of BrdU, which predominantly labels the proliferating transient amplifying cells (TA-cells) that compose most of the crypt, and then mice were sacrificed 24 hours later, 24 hours after a pulse of BrdU (i), CR reduced the migration of labeled BrdU labeled cells into the villi (j, n=3). However, normalized to the total number of villous enterocytes, there is no significant difference in the percentage of BrdU positive cells in CR villi compared to AL controls, indicating that at equilibrium in CR mice TA-cells have lower output for shorter, less cellular villi (k, n=3). Values±s.d. scale bar 50 µm.
Figure 5B:
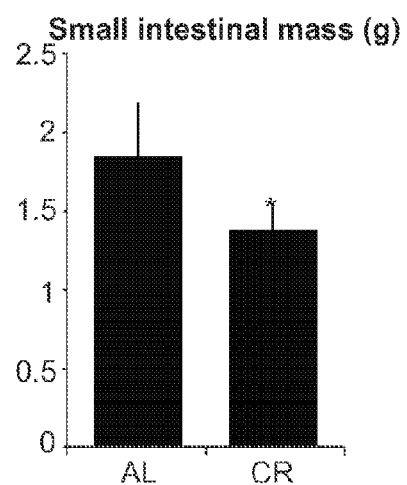
Figure 5C:
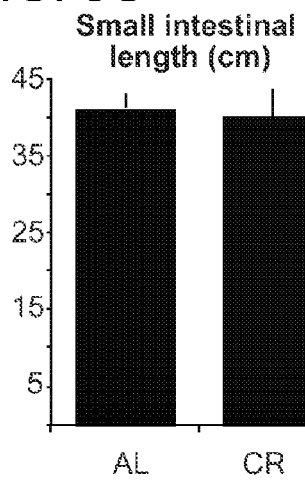
Figure 5D:
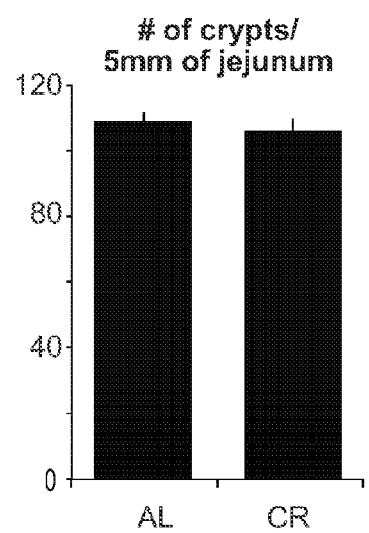
Figure 5E:
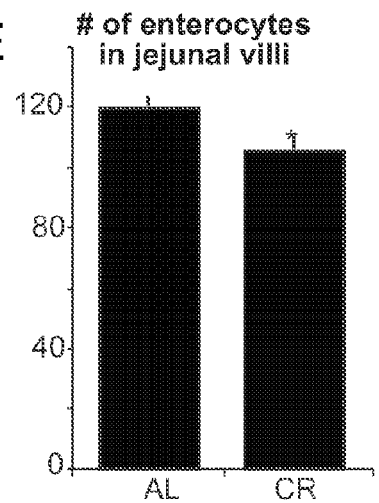
Figure 5F:
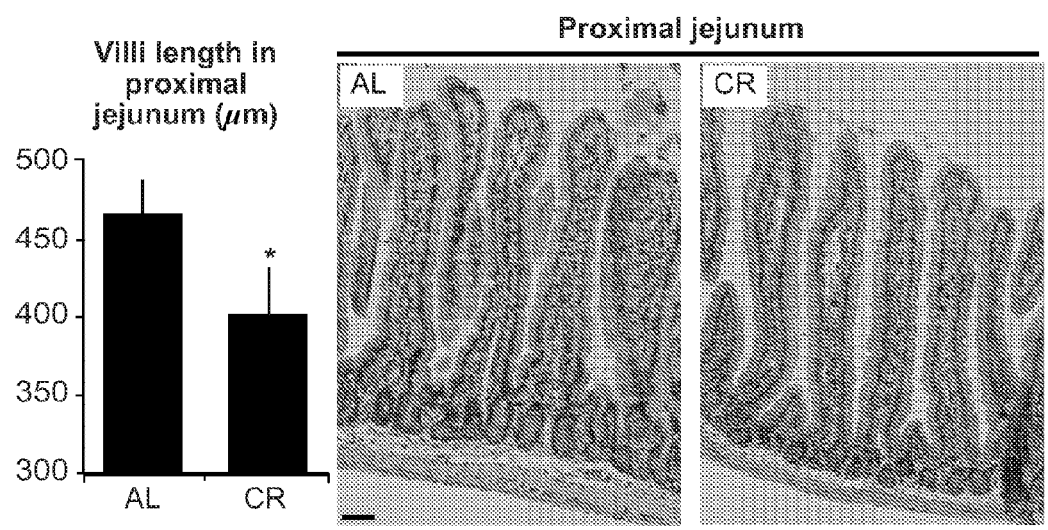
Figure 6A:
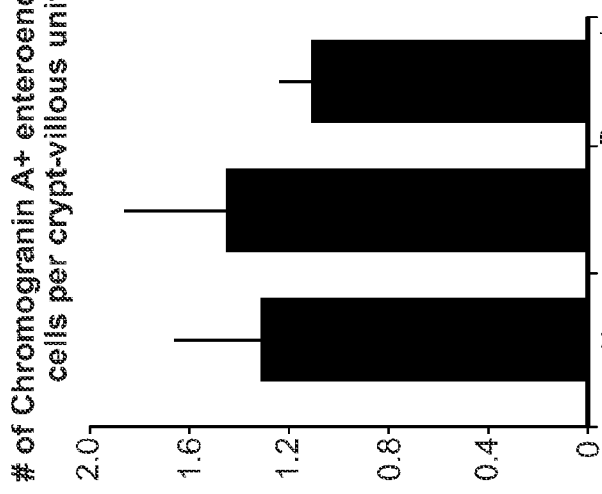
FIGS. 6a-b. Calorie restriction and rapamycin treatment have minimal effects on enteroendocrine and goblet cell differentiation (a) An immunostain for chromogranin A revealed no difference in the numbers of jejunal enteroendocrine cells (arrow, n=3) per crypt-villous unit in mice from calorie restriction (CR) compared to those in ad libitum (AL) fed controls. (b) An Alcian blue stain showed a mild reduction in mucinous goblet cells (arrow) in CR compared to rapamycin treated and AL controls. Values±s.d. scale bar 20 µm.
Figure 6A:
Figure 6B:
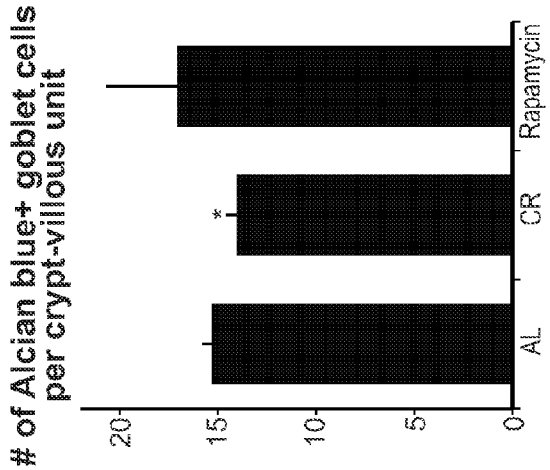
Figure 6B:
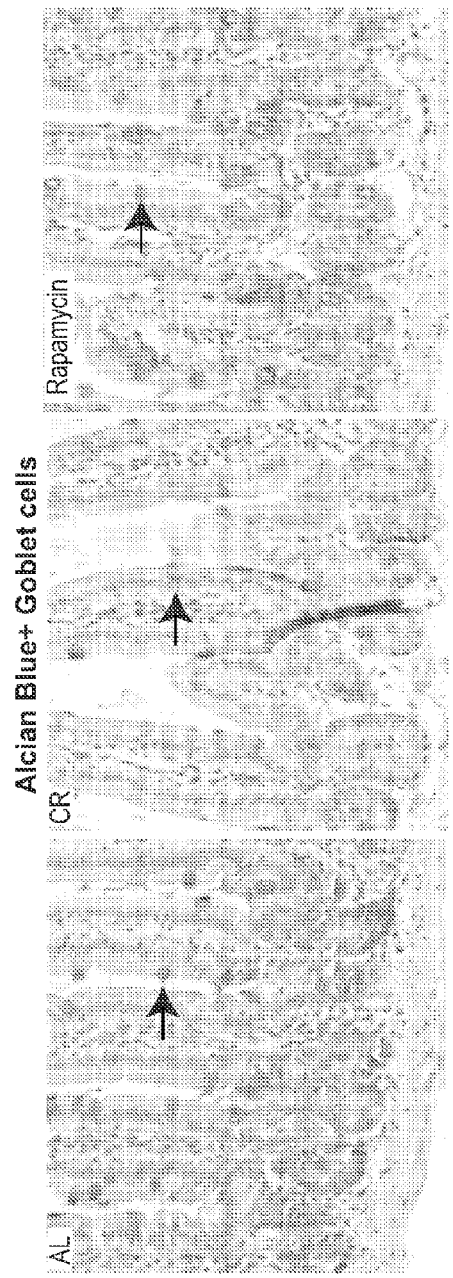
Figure 7:
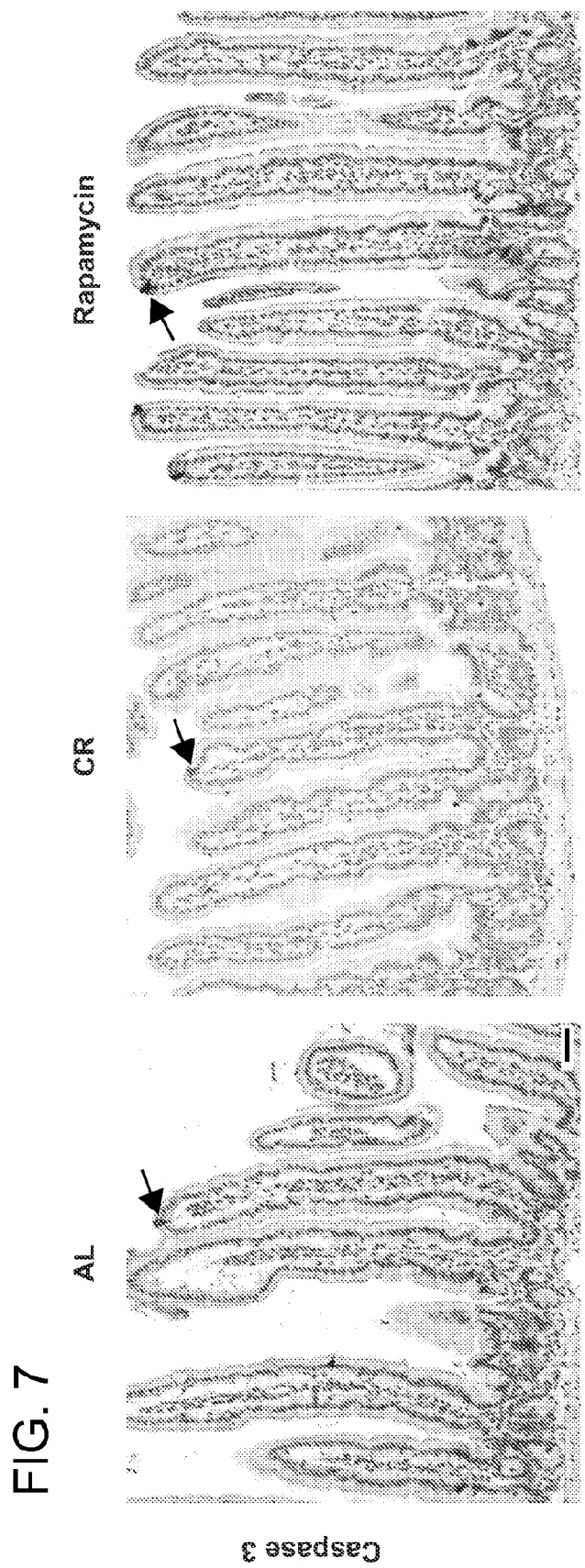
FIG. 7. Enterocyte apoptosis is not affected by calorie restriction. Immunostains for cleaved caspase 3 demonstrated no increase by calorie restriction (CR) or rapamycin treatment compared to ad libitum (AL) fed controls. The arrow indicates apoptotic cells at the tips of the villi. (n=3 per group, scale bar 50 µm).
Figure 8A:
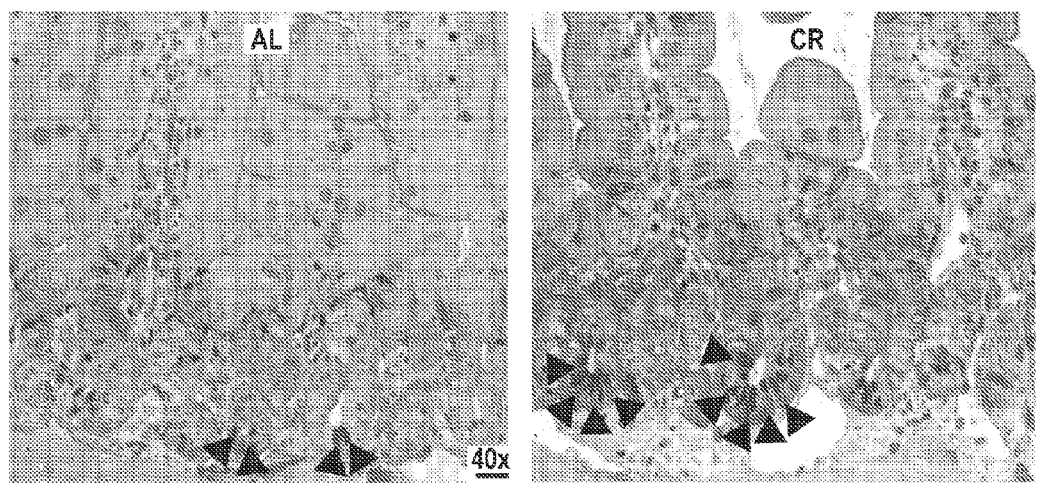
FIGS. 8a-b. Paneth cell ultrastructure is not altered by calorie restriction. (a) One micron sections of proximal jejunum counterstained with Toluidine Blue revealed increased numbers of Paneth cells (arrowheads) in calorie restriction (CR) compared to ad libitum (AL) fed controls. The proximal jejunum was defined as the length between 6 to 9 cm as measured from the pylorus (distal portion of the stomach). (b) Electron microscopy images of representative crypts from AL and CR jejunum demonstrated no differences in the morphologic ultrastructure of crypt base columnar cells (arrow) and Paneth cells (arrowhead). Scale bar 2 µm.
Figure 8B:
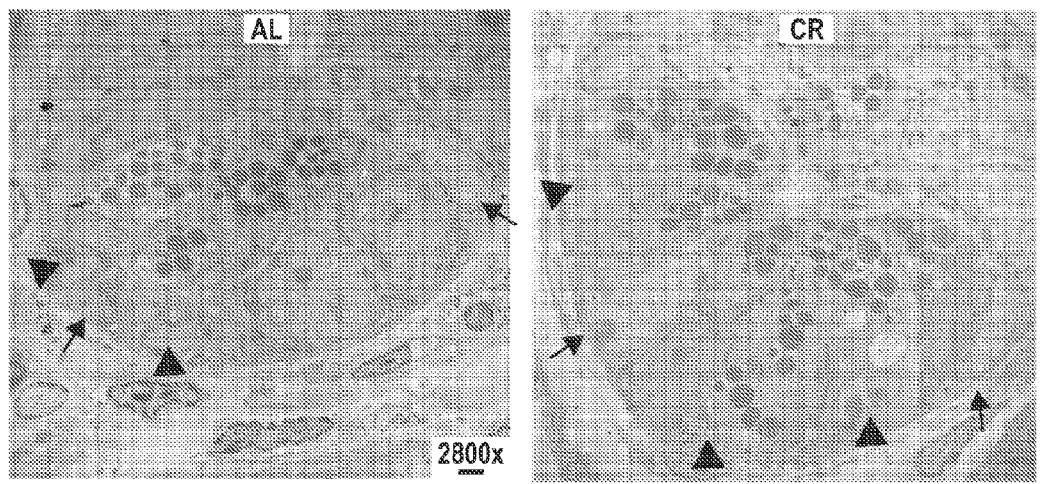
Figure 9A:
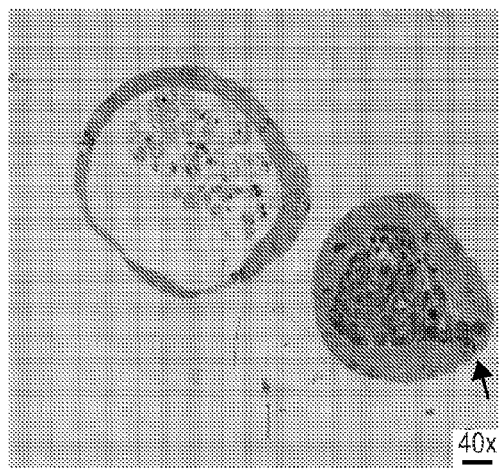
FIGS. 9a-d. Organoid bodies recapitulate normal intestinal morphology and possess all intestinal cell types. Organoid bodies derived from the coculture of sorted Paneth cells and ISCs were harvested after 10 days of incubation. (a) An H&E-stained section of an organoid body illustrates crypt domains (arrow) and the myriad cell types observed in the small intestine. (b-d) Election microscopy images of organoid bodies highlight the various cell types associated with the mammalian small intestine including Paneth cells (b, arrowheads), crypt base columnar cells that are adjacent to the Paneth cells (b, arrow, scale bar 10 µm), mucinous goblet cells (c, arrow, scale bar 2 µm), and mature enterocytes with their microvilli (d, arrow, scale bar 2 µm).
Figure 9B:
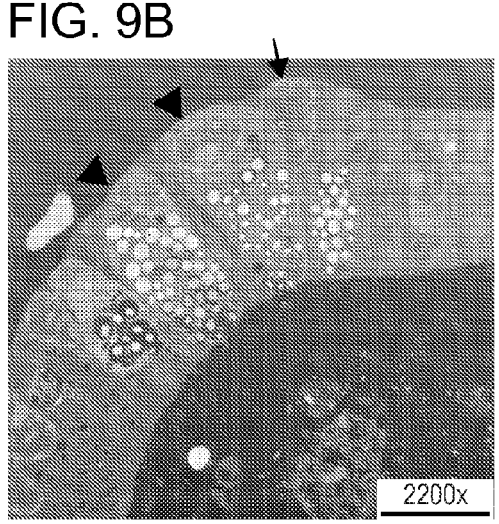
Figure 9C:
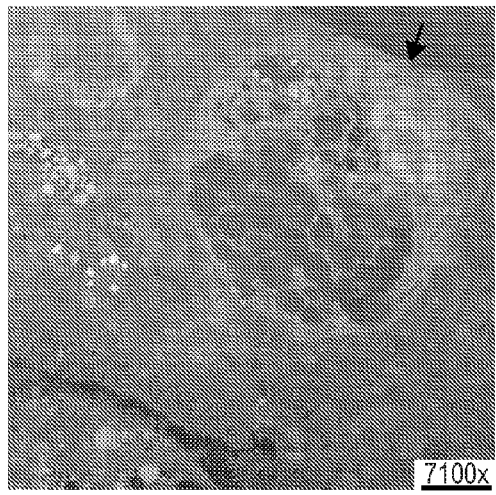
Figure 9D:
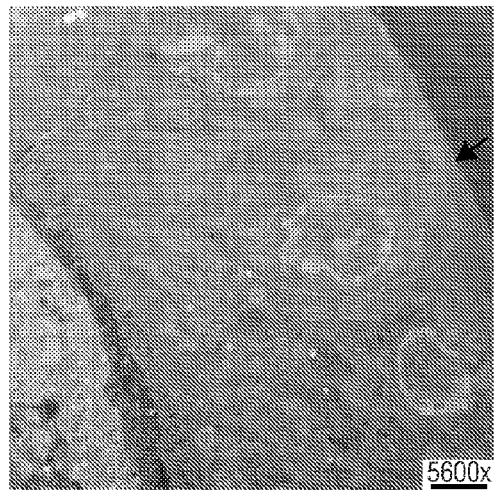
Figure 10A:
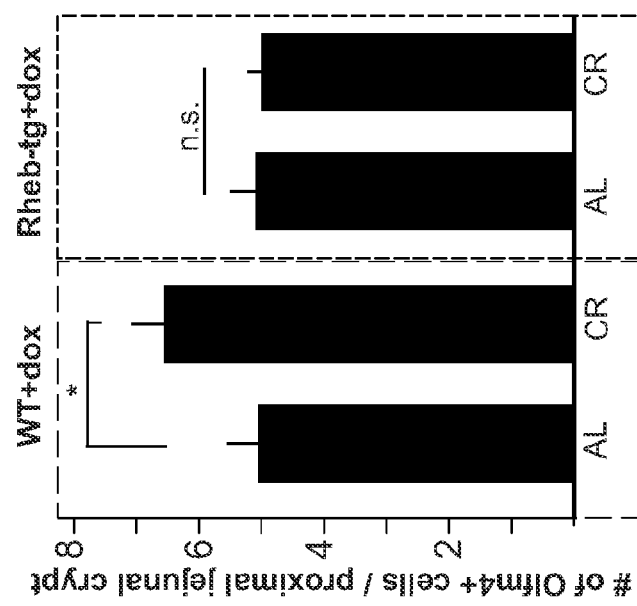
FIGS. 10a-c. Activation of the Rheb2 transgene blunts the increase in intestinal stem cell and Paneth cell frequency that is observed in calorie restriction. (a-b) Calorie restriction (CR) increased the frequency of Olfactomedin-4+ (Olfm4) intestinal stem cells (a, ISCs) and of Cryptdin4+ Paneth cells (b) by in situ hybridization. This increase in ISCs and Paneth cells was abrogated when the Rheb2 transgene (Rheb-tg) was induced during the onset of CR with doxycycline. Representative images of the proximal jejunum stained for Olfm4 and Cryptidin4 by in situ hybridization. (c) To independently confirm that persistent mTORC1 activity negated the increase in Paneth cell frequency observed in CR, TSC1—a known negative regulator of mTORC1—was excised using $TSC1^{loxp/loxp}$; Rosa26(R26)-CreERT2 mice. The excision of TSC1 during CR prevented the increase of Paneth cells ($CD24^{hi}SideScatter^{hi}Lgr5-EGFP^-Epcam^+CD31^-Ter119^-CD45^-$ live cells) as assessed by flow cytometry. 5 injections of tamoxifen were administered to $TSC1^{loxp/loxp}$; Rosa26(R26)-CreERT2 mice during the onset of CR and the mice were analyzed 3-4 weeks from the start of CR (n=5-18). Values±s.d., * denotes p<0.05, and scale bar 50 µm.
Figure 10A:
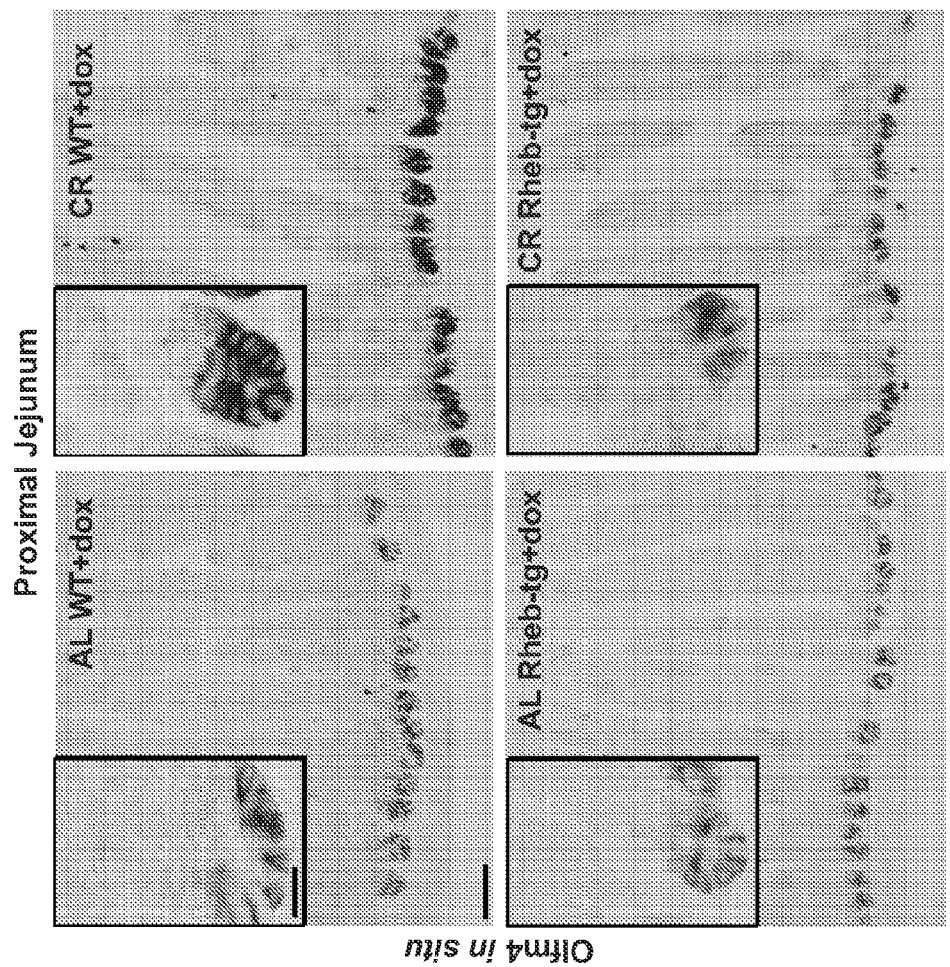

To assess the effects of CR on intestinal homeostasis, we calorically restricted mice for 4 to 28 weeks, which is sufficient to observe many of the metabolic phenotypes of CR[18,19]. The small intestine is organized into crypts that contain the stem cells and the rapidly dividing transient amplifying cells (TA-cells), and villi that are composed primarily of post-mitotic absorptive enterocytes. Consistent with prior reports, mice on CR had a 19.7±5.8% loss in body mass compared to ad libitum (AL) fed counterparts (FIG. 5a)[20]. The small intestine from CR mice was morphologically normal (FIG. 5f), with no change in the density of crypts (FIG. 5d), no difference in intestinal length (FIG. 5c), and no increase in apoptosis (FIG. 7). However, small intestine from CR mice had reduced mass (1.8±0.4 vs 1.4±0.2 g, FIG. 5b), and the villi were 15% shorter and possessed fewer enterocytes than to those in the intestines of AL mice (FIG. 5e and FIG. 5f). CR did not affect the frequency of chromogranin A+ enteroendocrine cells but caused a mild reduction in alcian blue+ secretory goblet cells (FIG. 6a and FIG. 6b). To address how CR influenced the frequency of ISCs, we performed in situ hybridization for Olfactomedin-4 (Olfm4), a recently described marker that is coexpressed by Lgr5+ ISCs as well as by other undifferentiated intestinal progenitors[21]. CR led to a 35% increase in Olfm4+ primitive intestinal progenitors compared to those in AL mice (FIG. 1a, FIG. 10a). Surprisingly, we also observed a commensurate increase in Cryptdin4+ Paneth cells in CR mice (FIG. 1a), which we confirmed by independently examining Paneth cells morphologically in one-micron tissue sections at the same distance along the small intestine (FIG. 8a) and by electron microscopy (FIG. 8b). These findings illustrate two intriguing observations: First, CR promotes the preservation and self-renewal of ISCs (increased Olfm4+ ISCs) at the expense of differentiation (shorter villi with fewer mature enterocytes). Second, ISC and their Paneth cell numbers increase in tandem, raising the possibility that the Paneth cell niche may coordinate ISC adaptation to CR.

Figure 5G:
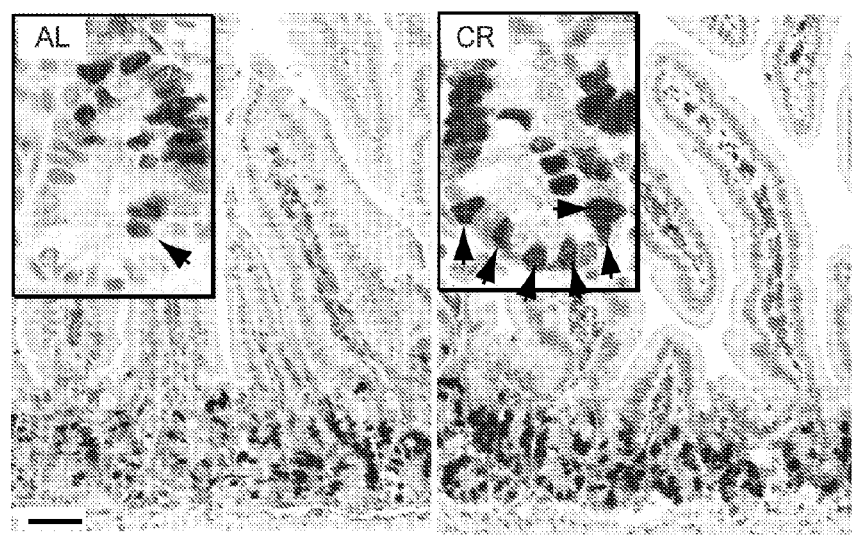
Figure 5H:
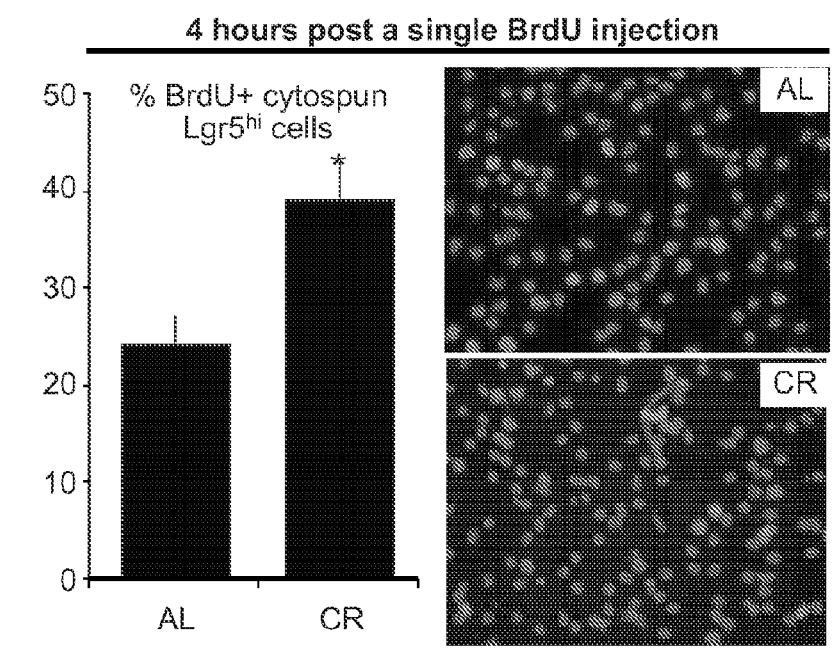
Figure 5I:
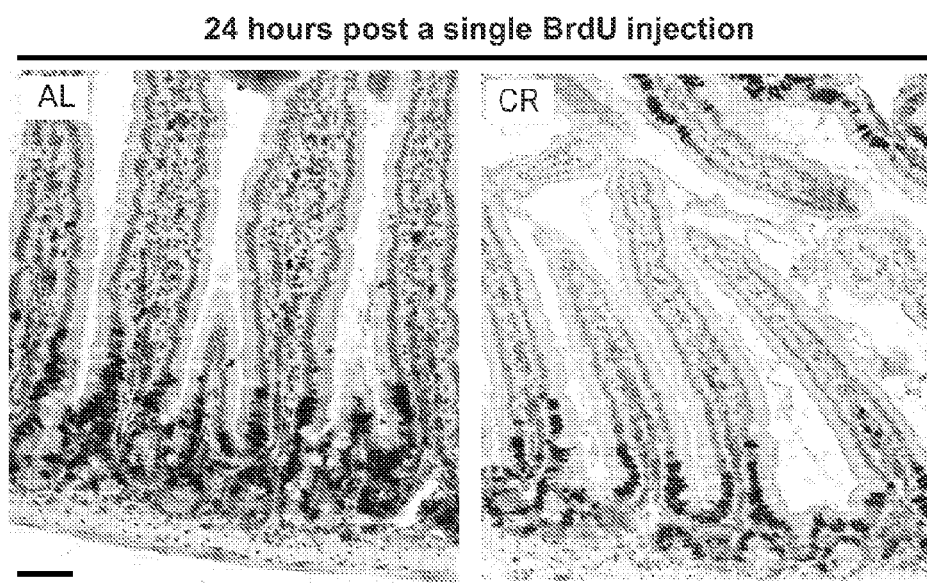
Figure 5J:
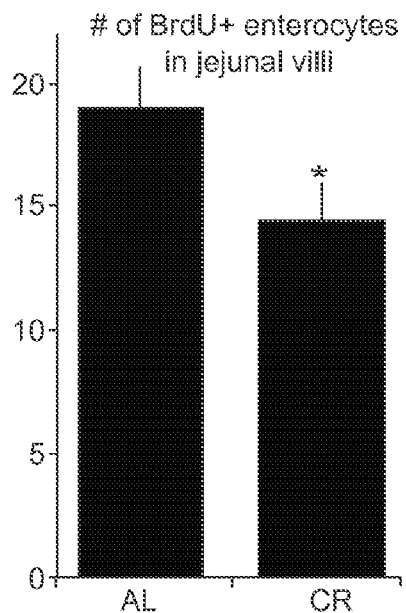
Figure 5K:
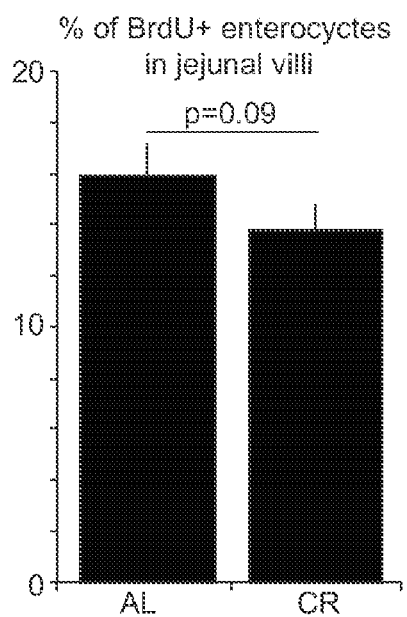

The fact that CR augmented ISC numbers while reducing the total number of differentiated enterocytes raised the question of whether CR enhanced the proliferation of ISCs and reduced the proliferation of more differentiated progenitors (TA-cells). To address this question, we assessed incorporation of BrdU, a thymidine analog that incorporates into the DNA of dividing cells, in ISCs and TA-cells. ISCs in CR mice, after a 4 hour pulse of BrdU, had nearly 2-fold as many BrdU+ cells compared to AL controls (4.3±0.3 vs 2.4±0.2, FIG. 1b, FIG. 5g, and FIG. 5h). However, even though CR increased ISC proliferation, it reduced by 20% the number of BrdU+ cells in the much larger pool of TA-cells (11.0±0.9 vs 9.4±0.5; FIG. 1b). Our finding that CR decreased TA-cell proliferation suggested that output from this compartment, as assessed by migration of BrdU labeled cells up the villi, may also be reduced. To assess this, we counted the number of BrdU positive cells in the villi 24 hours after a single dose of BrdU. CR mice, consistent with the reduced proliferation of TA-cells, had fewer absolute numbers of BrdU labeled cells in the villi compared to AL controls (14.5±1.5 vs 19.0±1.7, FIG. 5*i* and FIG. 5*j*). However, when normalized to total villous enterocytes, there was no significant difference in the percentage of BrdU+ villous enterocytes in the CR villi compared to those in AL controls, indicating that at equilibrium in CR mice TA-cells have lower output for shorter, less cellular villi (FIG. 5*k*). While CR increased the number of BrdU+ ISCs, the reduced proliferation and output of TA-cells into the villi may account for the shorter villi observed in CR. These data demonstrate that CR uncouples stem cell and TA-cell proliferation in vivo as a mechanism to achieve intestinal adaptation to a low calorie state.

Because CR increased the phenotypic frequency and proliferation of ISCs we asked whether it also promoted the regeneration of the small intestinal epithelium. To address this question, we isolated crypts, which are the functional units of the intestine that possess all of the stem and progenitor cells, and assayed their unbiased potential to form clonal, multipotent organoid bodies that possess all intestinal cell types in vitro[22]—independent of intestinal stem cell markers (FIG. 9). Isolated crypts from CR mice were nearly 2-fold more likely to give rise to organoid bodies compared to crypts from AL mice (FIG. 1*c*). Collectively, these data suggest that CR leads to a functional increase in stem cell activity per crypt, as only stem cells are capable of self-renewing and differentiating into the various cell types that are required for organoid body formation and maintenance.

Figure 1E:
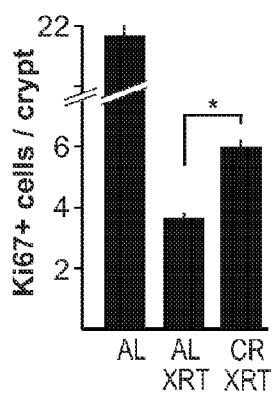

To validate whether CR also augmented crypt regeneration in vivo, we used the established clonogenic microcolony assay for testing ISC activity[23]. In AL and CR mice exposed to lethal doses of radiation and examined 72 hours later, we found that, per unit length of intestine, CR significantly increased the number of surviving and regenerating crypts and Ki67+ intestinal progenitors (FIG. 1*d* and FIG. 1*e*). These data are consistent with our in vivo and in vitro data showing that CR increases the numbers and regenerative capacity of ISCs.

Figure 10B:
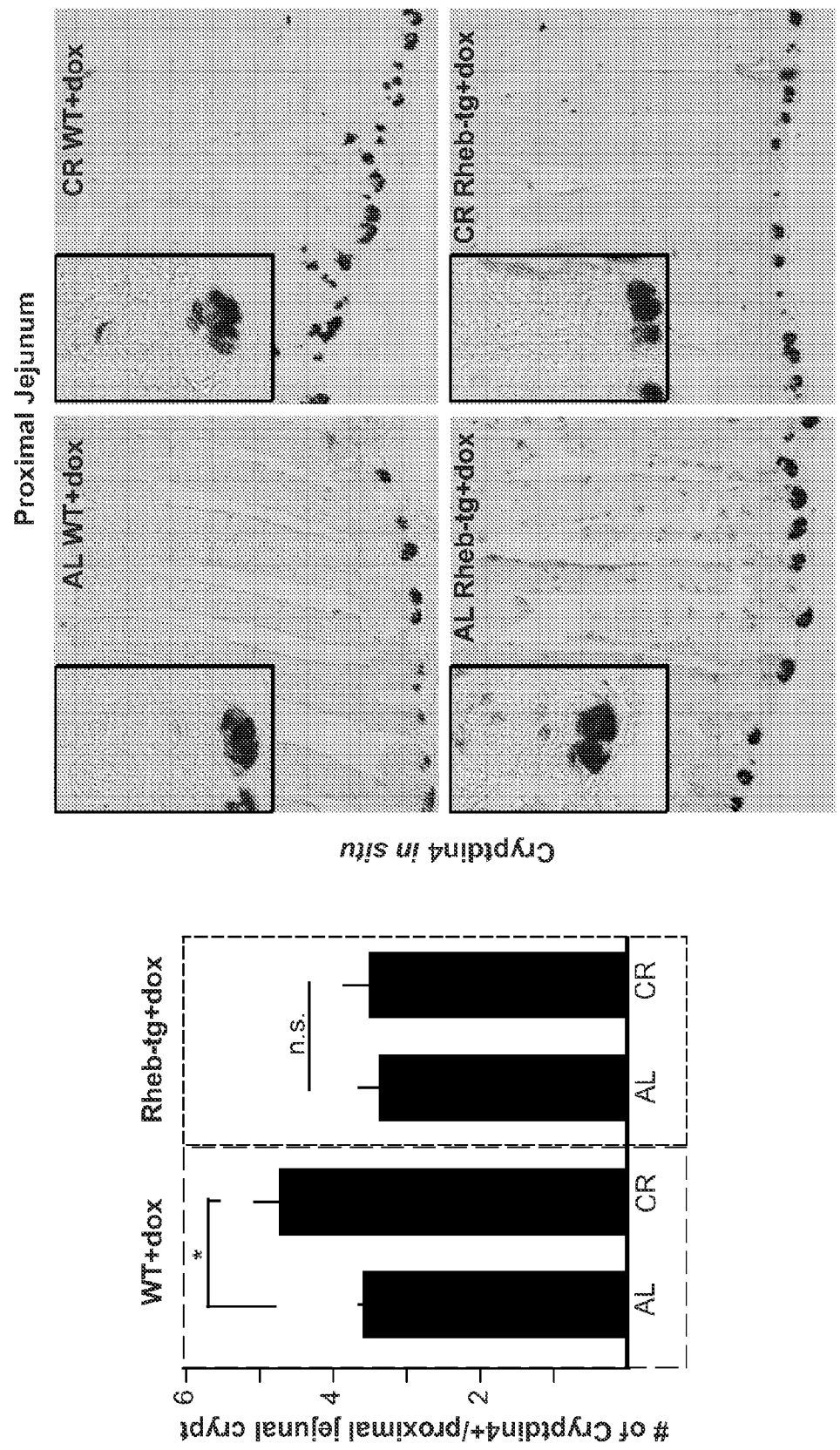

To better understand how CR affects the frequency and function of ISCs and their Paneth cell niche, we performed CR experiments on Lgr5-EGFP-IRES-CreERT2 knock-in mice; these mice allow for the prospective isolation by flow cytometry of Lgr5-EGFP$^{hi}$ ISCs and their daughter, more differentiated EGFP$^{low}$ cells[17]. Compared to AL feeding, CR increased the frequency of Lgr5-EGFPhi ISCs (5.6±2.1% vs. 4.3±1.9%, FIG. 1*f*) as well as Paneth cells by 1.5-fold (9.8±3.3% vs. 6.7±3.3%, FIG. 1*f*). The frequency of EGFP$^{low}$ differentiated progenitors, however, was lower in CR (8.1±3.0% vs. 10.1±4.3% FIG. 1*f*). First, these data corroborate the phenotypic expansion of ISCs and Paneth cells observed independently with the Olfm4 and Cryptdin4 markers, respectively (FIG. 1*a*, FIG. 10*a*, and FIG. 10*b*). Second, these data suggest that while CR expands the pool of ISCs it leads to a reduction of more differentiated progenitors. Thus, CR has opposing effects on stem cells and their immediate progeny, shifting the equilibrium towards stem cell self-renewal.

Figure 1G:
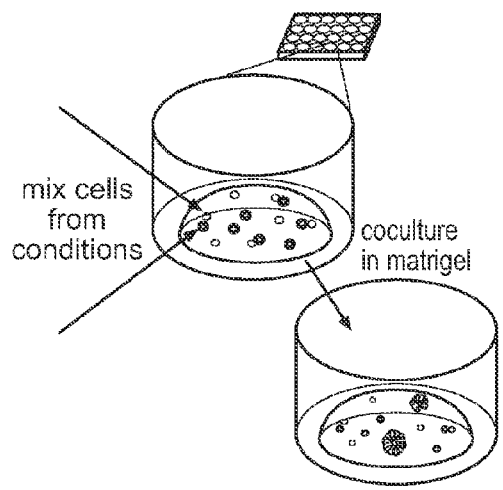
Figure 1F:
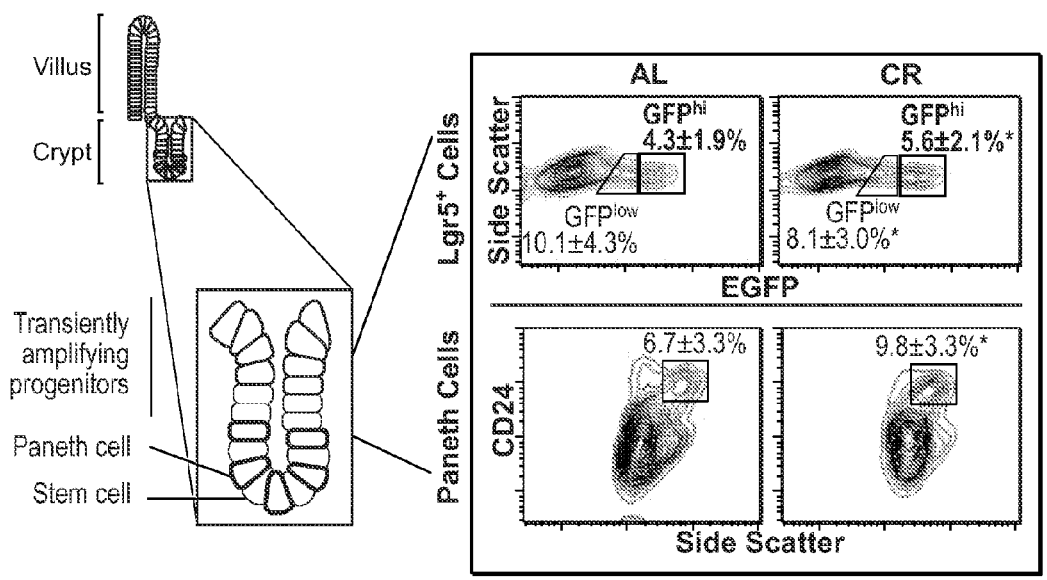
Figure 1H:
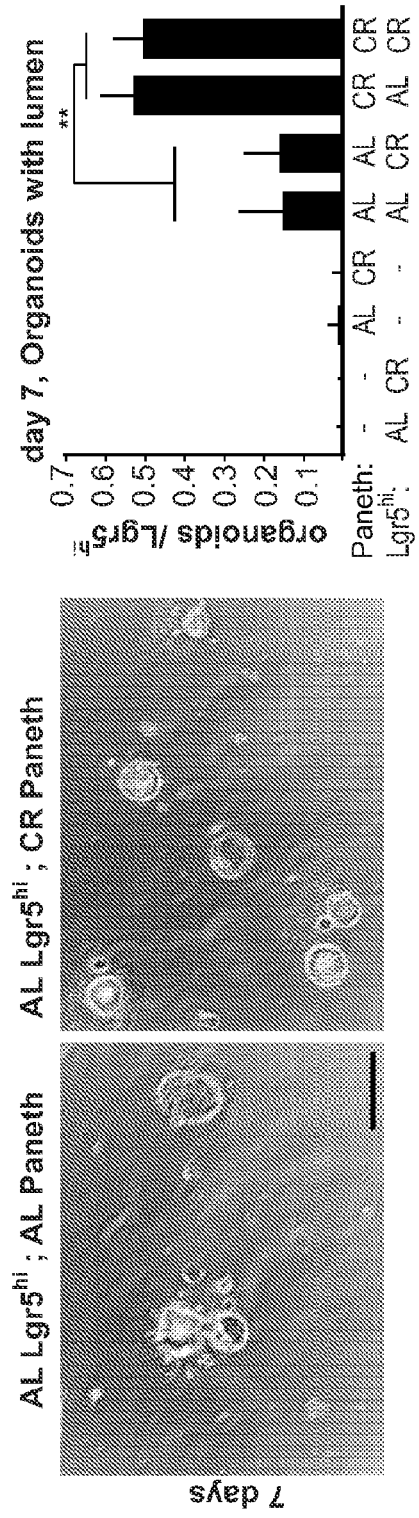
Figure 1I:
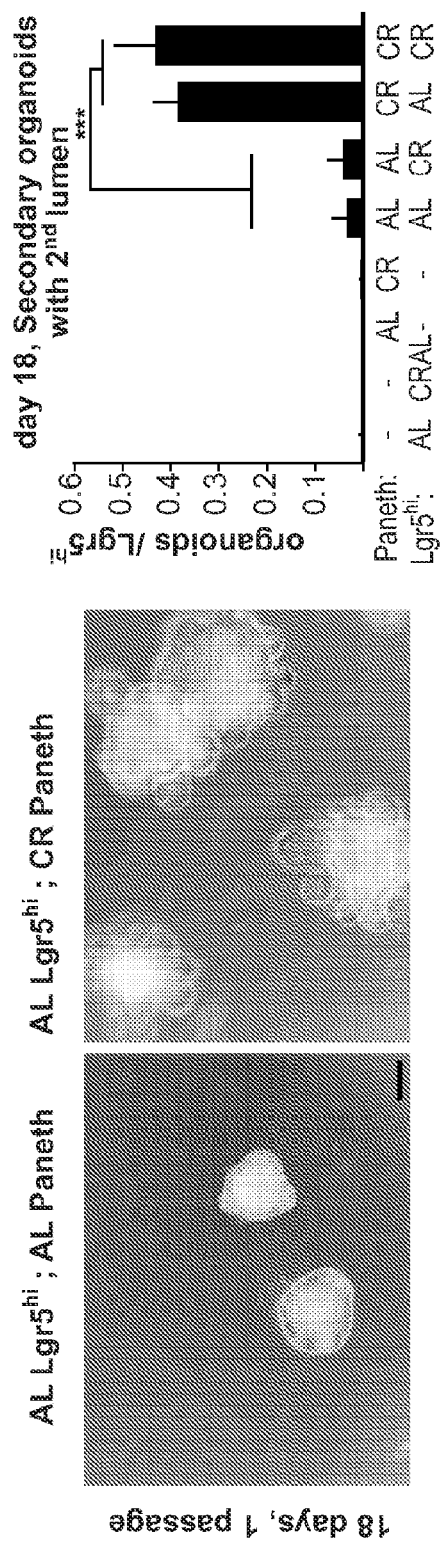
Figure 1J:
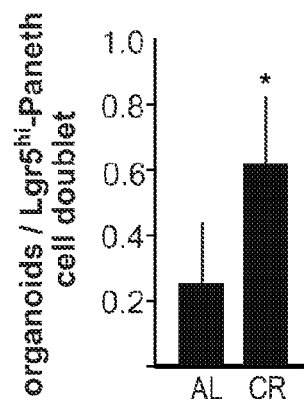
Figure 1K:
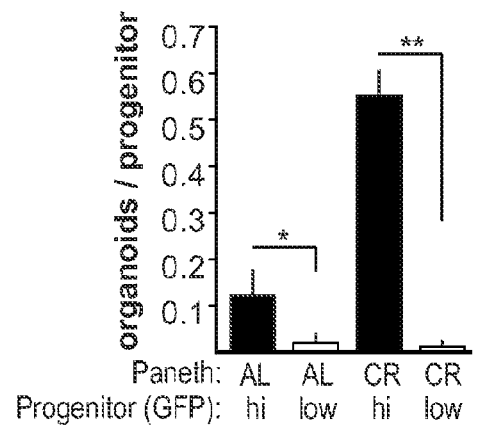
Figure 1L:
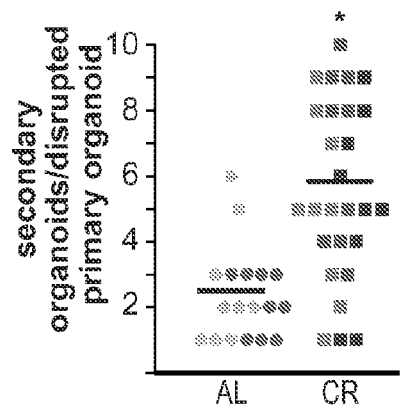

The enhanced functional activity of CR crypts led us to ask whether ISCs respond to CR autonomously or non-autonomously through the Paneth cells. To distinguish between these possibilities, we combined ISCs and Paneth cells isolated from CR and AL mice and assessed their ability to form organoid bodies in culture (FIG. 1*g*). Consistent with prior studies[3, 22], on their own Lgr5-EGFP$^{hi}$ISCs or Paneth cells did not establish organoid bodies, but, when cocultured, 15% of ISCs did initiate organoid bodies (FIG. 1*g* and FIG. 1*h*). Interestingly, Paneth cells isolated from CR mice were 3 to 4 fold more likely than those from AL mice to promote organoid body formation when mixed with ISCs (FIG. 1*h*), and this augmentation persisted even after 7 months of CR (0.08±0.05 vs. 0.42±0.19, p=0.02). In contrast, CR had neither a direct effect on ISC function (as CR or AL ISCs behaved similarly), nor did it boost the potential of EGFP$^{low}$ progenitors to form organoid bodies (FIG. 1*h* and FIG. 1*k*). To rule out the possibility that this enhancement of CR Paneth cells resulted from an increased ability to home and attach to ISCs in culture, we sorted ISC-Paneth cell doublets from AL and CR mice and observed a similar 3-fold increase in the potential of CR-derived doublets to give rise to organoid bodies (FIG. 1*j*). Not only did CR-derived Paneth cells promote primary organoid body formation, these primary organoid bodies gave rise to more and larger secondary organoid bodies, even when individually subcloned (FIG. 1*i* and FIG. 1*l*). Thus, individual organoid bodies from CR-derived Paneth cells possess a greater ability to self-renew and this enhancement persists in culture (FIG. 1*l*). The fact that Lgr5-EGFP$^{hi}$ ISCs—and not EGFP$^{low}$ progenitors— form more organoid bodies when co-cultured with CR-derived Paneth cells indicates that most Lgr5-EGFP$^{hi}$ cells harbor stem cell potential when exposed to the appropriate niche signals (FIG. 1*h* and FIG. 1*k*).

Figure 2A:
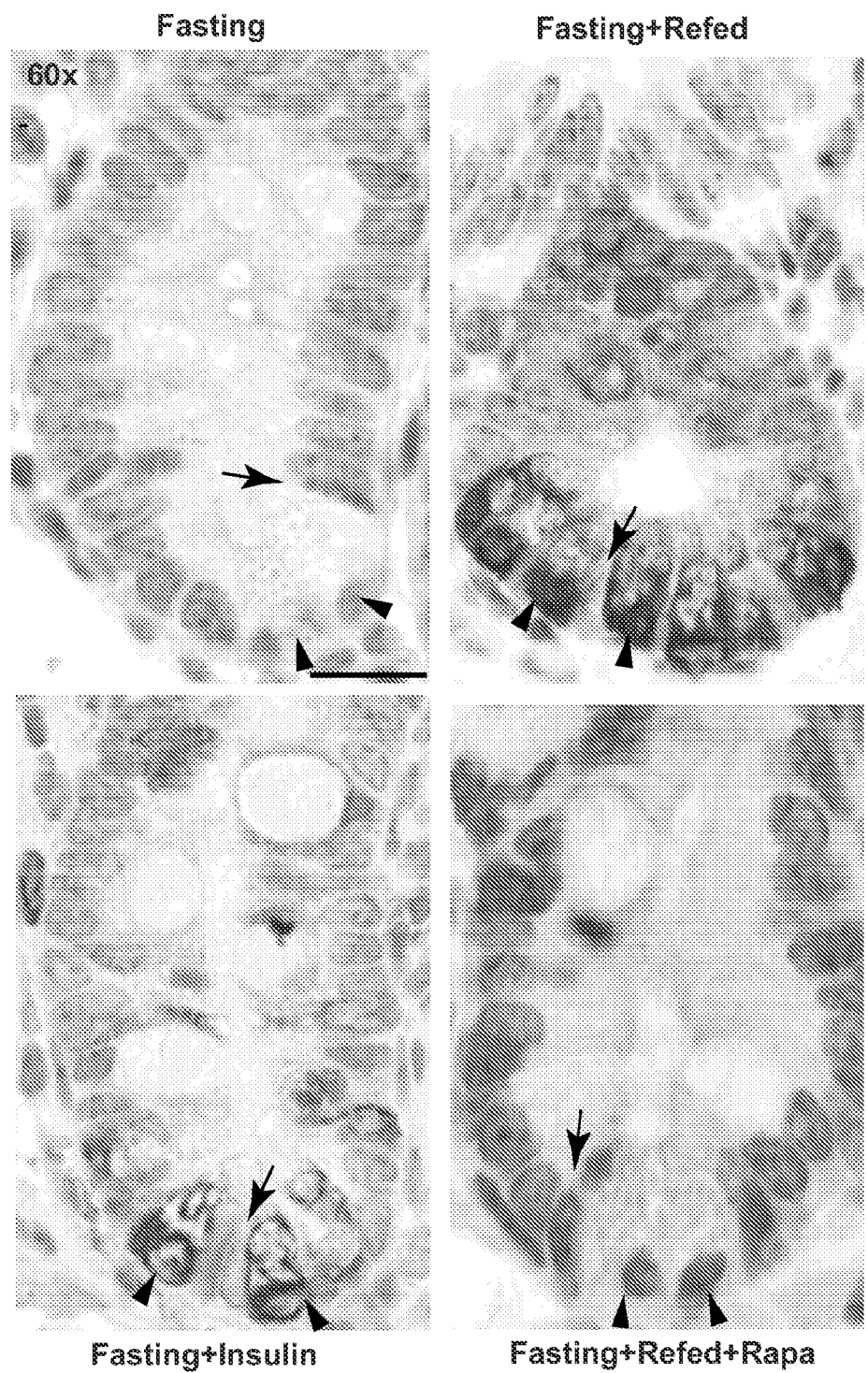
FIGS. 2a-c. Nutritional regulation of mTORC1 in Paneth cells. (a) Re-feeding or administration of insulin activates mTORC1 in Paneth cells (arrow heads) but not ISCs (arrows, n=3-5, scale bar 20 µm). Overnight fasted mice treated without or with rapamycin were refed for 5 hours and intestinal sections immunostained for phospho-S6 (P-S6), an established mTORC1 reporter. (b) P-S6 was reduced in sorted Paneth cells from fasted mice and was induced 20 minutes after injection with insulin. Similar results were observed in cytospun preparations of sorted Paneth cells that were confirmed to be greater than 95% positive for the Paneth cell marker Lysozyme (n=3). (c) Immunoblots of isolated crypts from CR mice showing reduced phosphorylation of known mTORC1 substrates phospho-S6K (P-S6K) and P-S6.
Figure 2B:
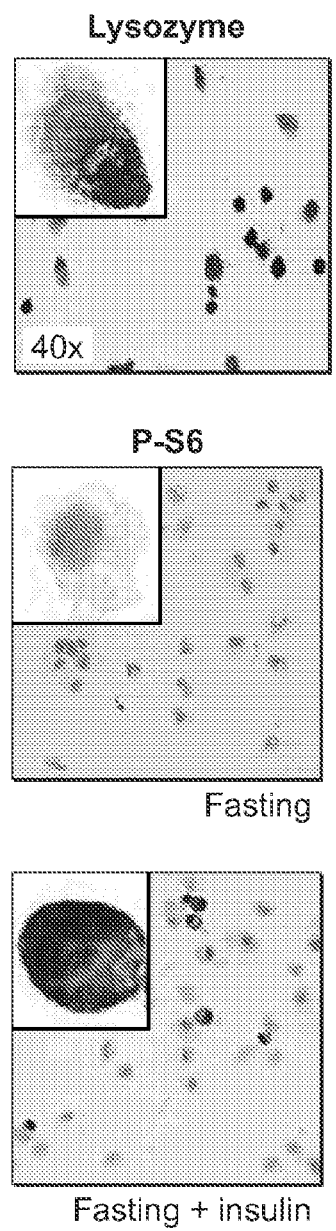
Figure 2C:
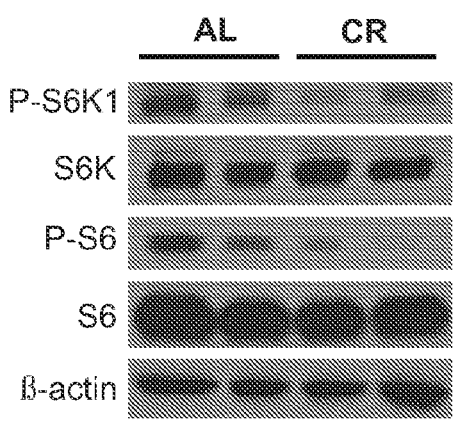

Because the multi-component kinase mTORC1 (mechanistic target of Rapamycin complex 1) is a major sensor of the organismal nutritional state, we asked whether CR mediates its effects on Paneth cells by attenuating mTORC1 activity[24]. Consistent with this, overnight fasting attenuated phosphorylation of S6 ribosomal protein (P-S6), a classical marker of mTORC1 activity in the intestines (FIG. 2*a*). Interestingly, feeding or insulin activated mTORC1 in Paneth cells but not in ISCs (FIG. 2*a*). Treatment of mice before feeding with Rapamycin, an allosteric inhibitor of mTORC1, blocked this activation (FIG. 2*a*). To confirm that we were observing Paneth cells, we cytospun isolated populations of Paneth cells (>95% lysozyme+; FIG. 2*b*) and found that P-S6 expression was indeed induced in the Paneth cells of fasted mice by insulin administration. Similarly, in immunoblots from isolated CR crypts, phosphorylation of S6 ribosomal protein and S6K1, the latter being a direct substrate of mTORC1, were diminished (FIG. 2*c*). These data suggest that Paneth cells may modulate ISC function by sensing organismal nutritional status in an mTORC1 dependent manner.

Figure 10C:
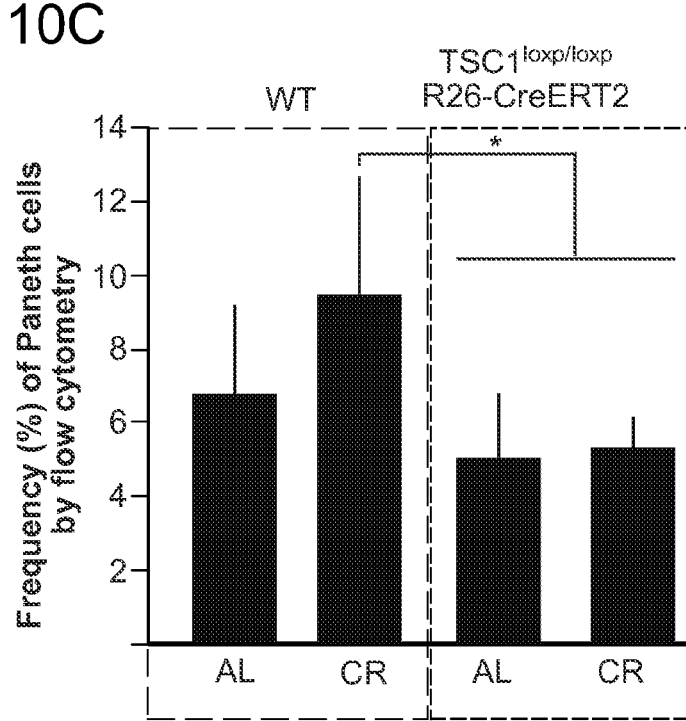
Figure 11A:
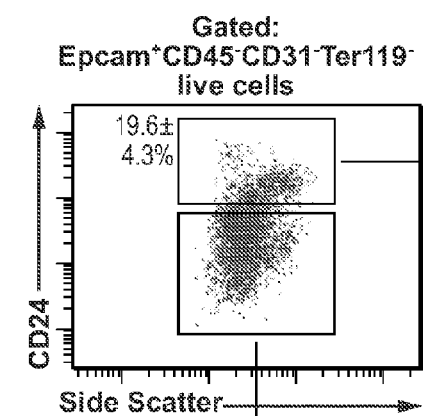
FIGS. 11a-c. CD24 positivity identifies a majority of Paneth cells in the murine small intestine. (a-c) To ascertain the reliability of CD24 in marking Paneth cells within the $Epcam^+CD31^-Ter119^-CD45^-$ live cell (a, all epithelial cells excluding hematopoietic and endothelial contaminants) compartment of the small intestine, CD24+ (a) and CD24− $Epcam^+CD31^-Ter119^-CD45^-$ (b) live cells were isolated, cytospun, and examined for the expression of known Paneth cell marker lysozyme and by morphology on H&E-stained preparations (b,c). 81.4±9.5% of $Epcam^+CD31^-Ter119^-$ CD45⁻ live cells expressed lysozyme (b, red immunofluorescence). As shown in reference³, FIG. 2b, and Supplemental FIG. 8b, Paneth cells could be further purified by gating on the SideScatter$^{hi}$ subset of CD24⁺Lgr5-EGFP⁻ Epcam⁺CD31⁻Ter119⁻CD45⁻ live cells to greater than 95% lysozyme positivity. In contrast, only 5.3±4.2% of the CD24- subset of Epcam⁺CD31⁻Ter119⁻CD45⁻ live cells was lysozyme positive. The simplest interpretation of these findings is that most Paneth cells are CD24⁺; however, it is unclear whether the CD24⁻ subset are truly negative or have lost the CD24 antigen during enzymatic tissue dissociation. Values±s.d.
Figure 11B:
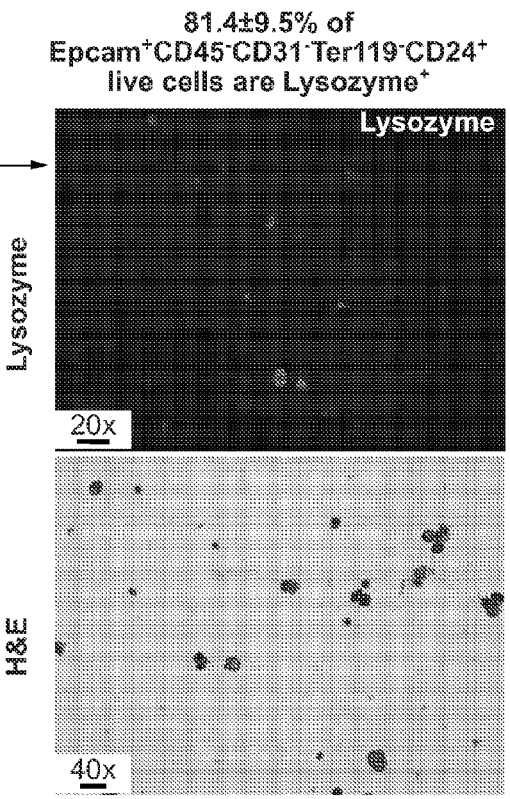
Figure 11C:
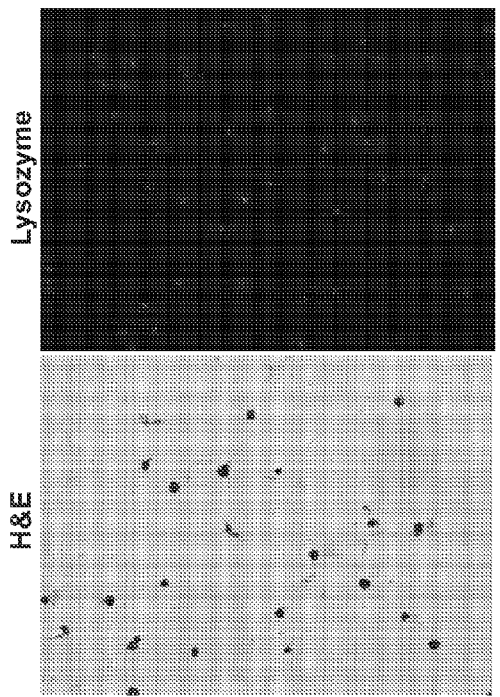
Figure 12A:
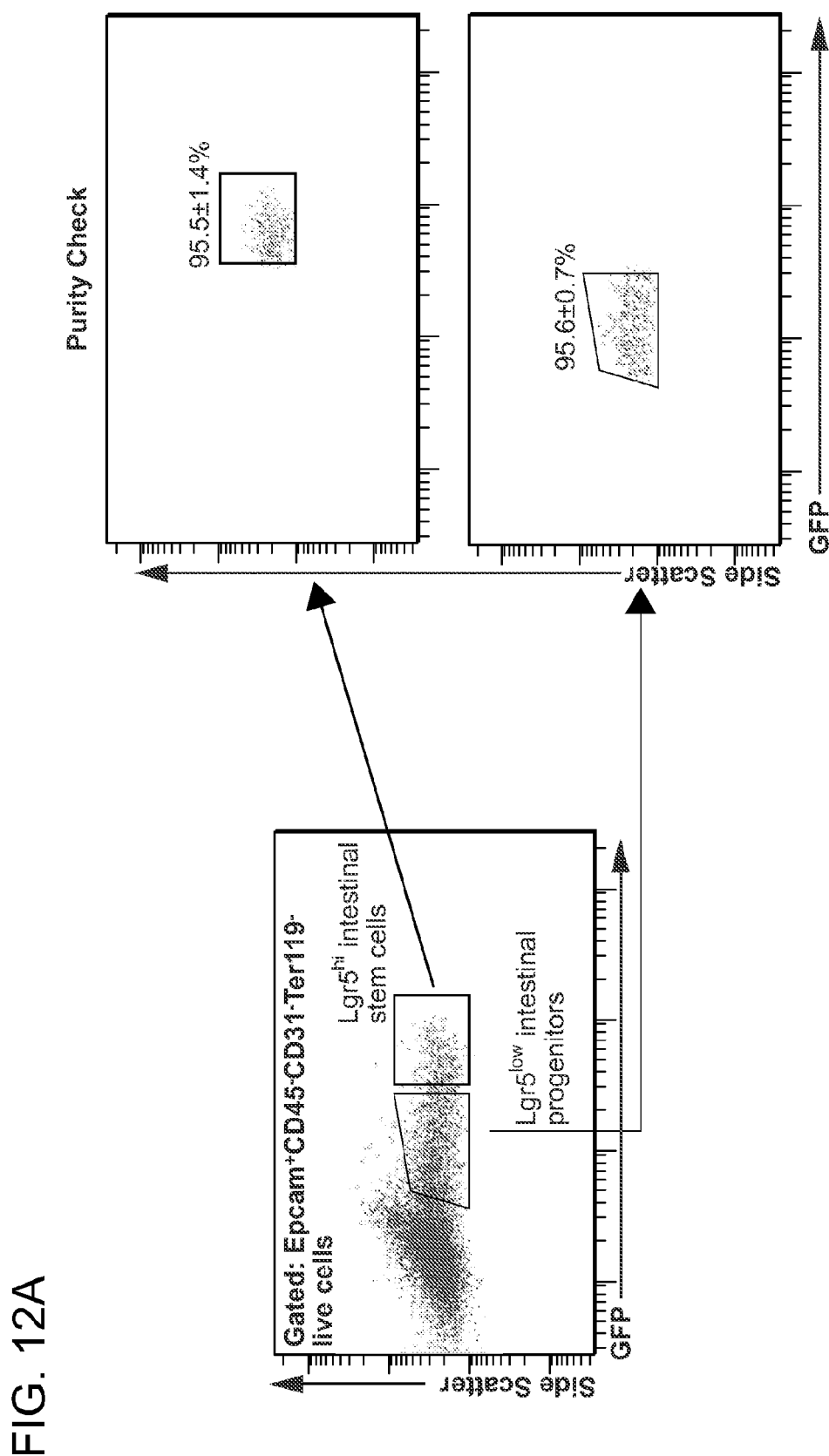
FIGS. 12a-b. Intestinal stem cells and Paneth cells can be isolated to near phenotypic purity. (a-b) Sorted and analyzed Lgr5-EGFP$^{hi}$ and EGFP$^{low/-}$Epcam⁺CD24$^{low/-}$CD31⁻Ter119⁻CD45⁻ live cells were 95.5=1.4% and 95.6±0.7% phenotypically pure, respectively (a, n=3). Similarly, sorted and analyzed CD24$^{hi}$SideScatter$^{hi}$Lgr5-EGFP⁻Epcam⁺CD31⁻Ter119⁻CD45⁻ live Paneth cells were 95.3±0.4% phenotypically pure (b, n=3). The SideScatter$^{hi}$ subset of CD24⁺Lgr5-EGFP⁻Epcam⁺CD31⁻Ter119⁻CD45⁻ live cells were greater than 95% Paneth cells based on immunostains for lysozyme, a known Paneth cell marker, in sorted and cytospun preparations. The lysozyme image is a lower magnification of the same slide from FIG. 2b. Values±s.d. and scale bar 100 μm.
Figure 12B:
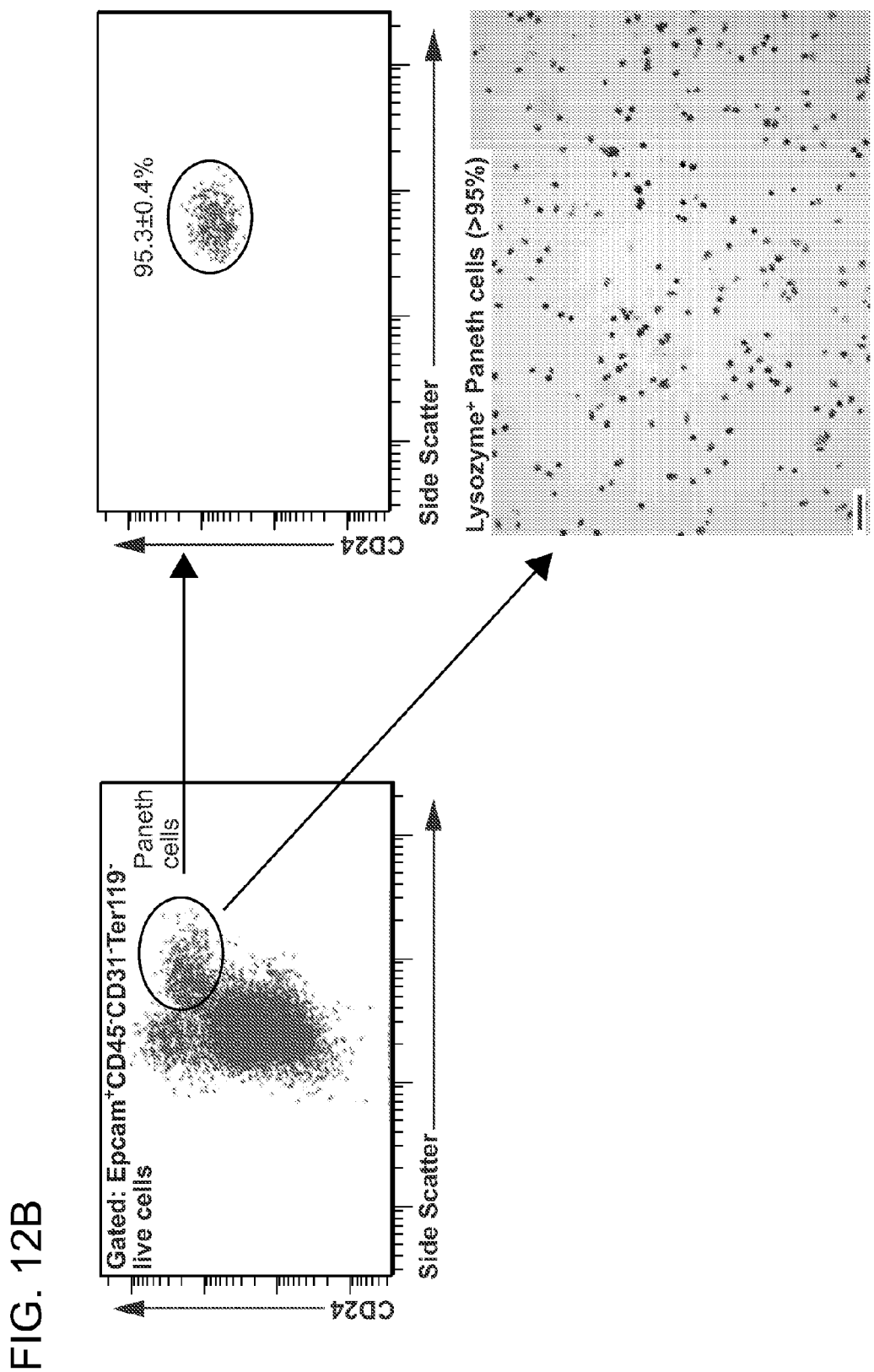

To address whether reduced mTORC1 signaling in Paneth cells enhances ISC function in CR, we generated mice in which the expression of Rheb2 (a specific activator of mTORC1) can be induced by doxycycline from the ubiquitously expressed ColA1 promoter (Rheb-tg) (FIG. 3*a* and FIG. 3*b*). We confirmed that induction of Rheb2 in Rhebtg mice was sufficient to activate mTORC1 signaling in the intestines of mice fasted overnight as well as in cytospun preparations of sorted Paneth cells (FIG. 3*c* and FIG. 3*d*). Interestingly, Rheb2 induction during CR blocked the increase in the clonogenicity per crypt (FIG. 3*e*) normally caused by CR, prevented Paneth cells isolated from the mice from enhancing organoid formation when cultured with ISCs (FIG. 3*f*), and abolished the increase in Olfm4+ ISC and Cryptdin4+ Paneth cell numbers observed in CR in vivo (FIG. 10*a* and FIG. 10*b*). To independently confirm that persistent mTORC1 activity negated the increase in Paneth cell frequency observed in CR, TSC1—a known negative regulator of mTORC1—was excised using TSC1$^{loxp/loxp}$; Rosa26-CreERT2 mice. The excision of TSC1 during CR (similar to Rheb induction) prevented the increase in Paneth cell frequency as assessed by flow cytometry (FIG. 10c). Thus, persistent mTORC1 activity during CR is sufficient to prevent CR Paneth cells from promoting ISC function (FIG. 3e, FIG. 3f, FIG. 10a, FIG. 10b, and FIG. 10c).

As constitutive activation of mTORC1 abrogated the effects of CR, we asked whether inhibition of mTORC1 with Rapamycin mimics the effects of CR on ISCs. Indeed, administration of Rapamycin to mice increased the frequency of ISCs and Paneth cells by more than 1.5-fold (FIG. 3g and FIG. 3h), and crypts isolated from mice treated for just 1 week with Rapamycin were as capable of forming organoid bodies as those from mice on CR (FIG. 3i). Because rapamycin can disrupt mTOR complex 2 (mechanistic target of rapamycin complex 2, mTORC2), we confirmed that the effects of Rapamycin on ISC function were specific to mTORC1 by showing that rapamycin increased the clonogenicity of crypts irrespective of whether they were isolated from adult intestines expressing or lacking Rictor, a necessary and specific component of mTORC2 (FIG. 3k)[25]. These data indicate that rapamycin mediates this enhancement in crypt clonogenicity by inhibition of mTORC1 activity and independently of mTORC2. Like CR, rapamycin acts non-autonomously as when Paneth cells isolated from rapamycin-treated mice were mixed with ISCs from control or rapamycin-treated mice, they caused a prominent increase in the formation of primary and subcloned secondary organoid bodies (FIG. 3j, FIG. 3l, and FIG. 3m). Moreover, rapamycin treatment and CR did not have additive effects on either the ability of crypts (FIG. 3i) or Paneth cells (FIG. 3j) to form organoid bodies, suggesting that CR mediates many of its effects by reducing mTORC1. These data, together with the finding that CR and rapamycin have non-additive effects (FIG. 4g), demonstrate that CR and rapamycin indirectly promote ISC function and do so by reducing mTORC1 signaling in Paneth cells.

Figure 1M:
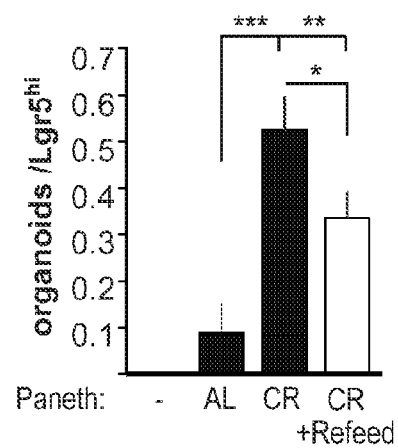
Figure 4A:
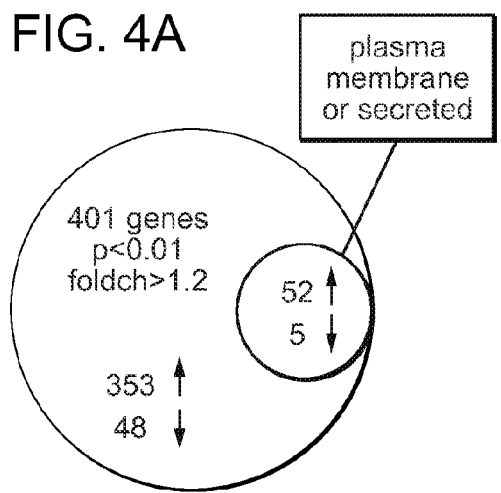
Figure 4B:
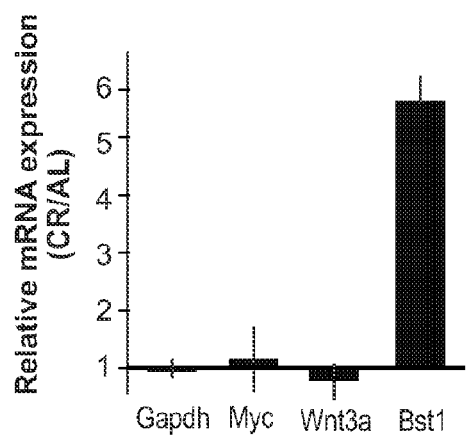
Figure 4C:
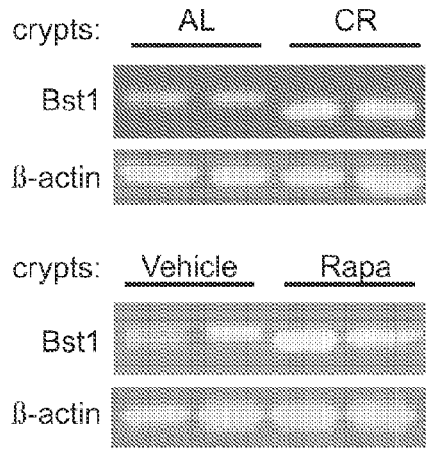
Figure 4D:
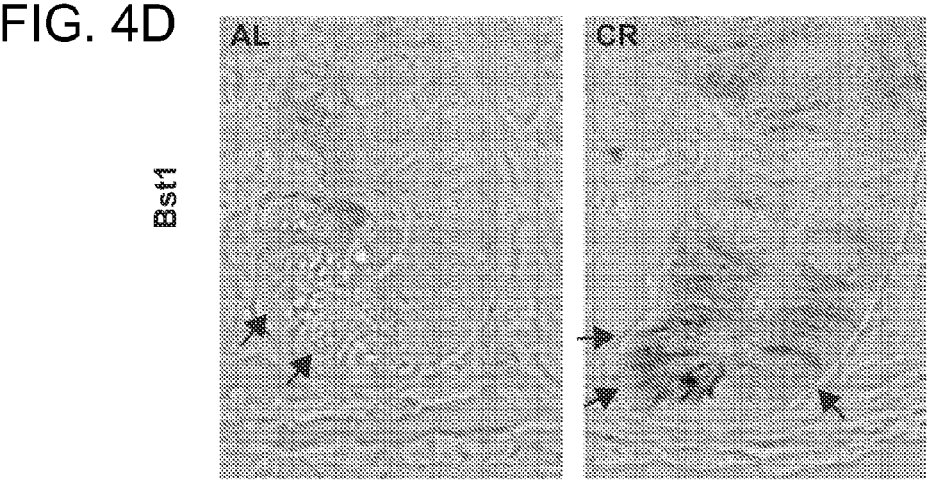

Several observations suggest that CR and rapamycin induce a state in Paneth cells that is quite stable. For example, Paneth cells taken from CR- or rapamycin-treated mice maintain their augmented capacity to promote ISC self-renewal even when placed in nutrient rich media that activates mTORC1. Similarly, Paneth cells isolated from mice that had been on CR, but were returned to an AL diet for 3 days, also retain an enhanced capacity to promote ISC function in the organoid assay (FIG. 1m). To gain mechanistic insight into how CR mediates its effects in Paneth cells, we undertook gene expression profiling on Paneth cells isolated by flow cytometry from AL and CR mice (n=3 and 4, respectively). CR significantly changed the expression of 401 genes (p<0.01), including 57 that encode cell surface or secreted proteins, but there were no significant expression changes components of the Wnt or Notch pathways that were previously shown to play important roles in the signaling between ISCs and Paneth cells (FIG. 4a and FIG. 4b)[3].

Figure 4G:
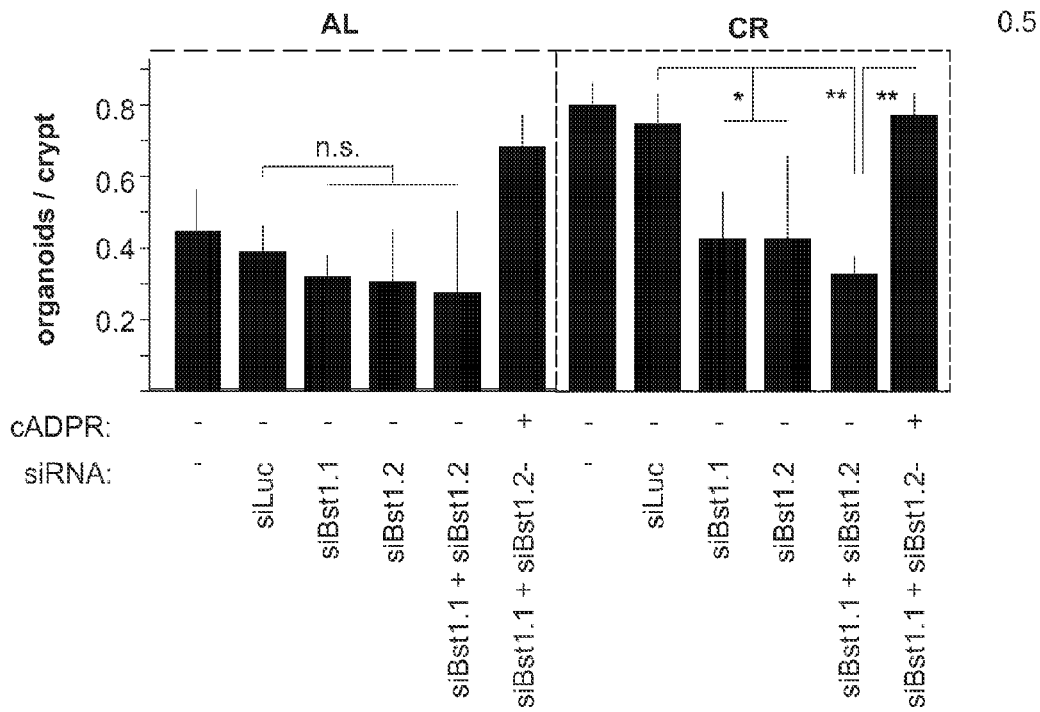
Figure 4H:
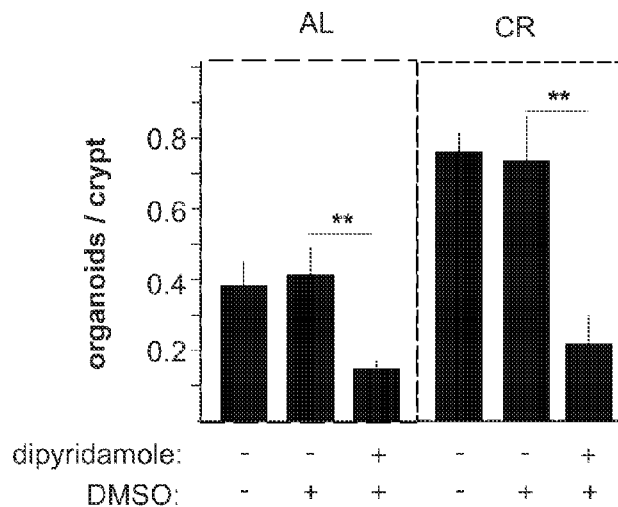
Figure 4I:
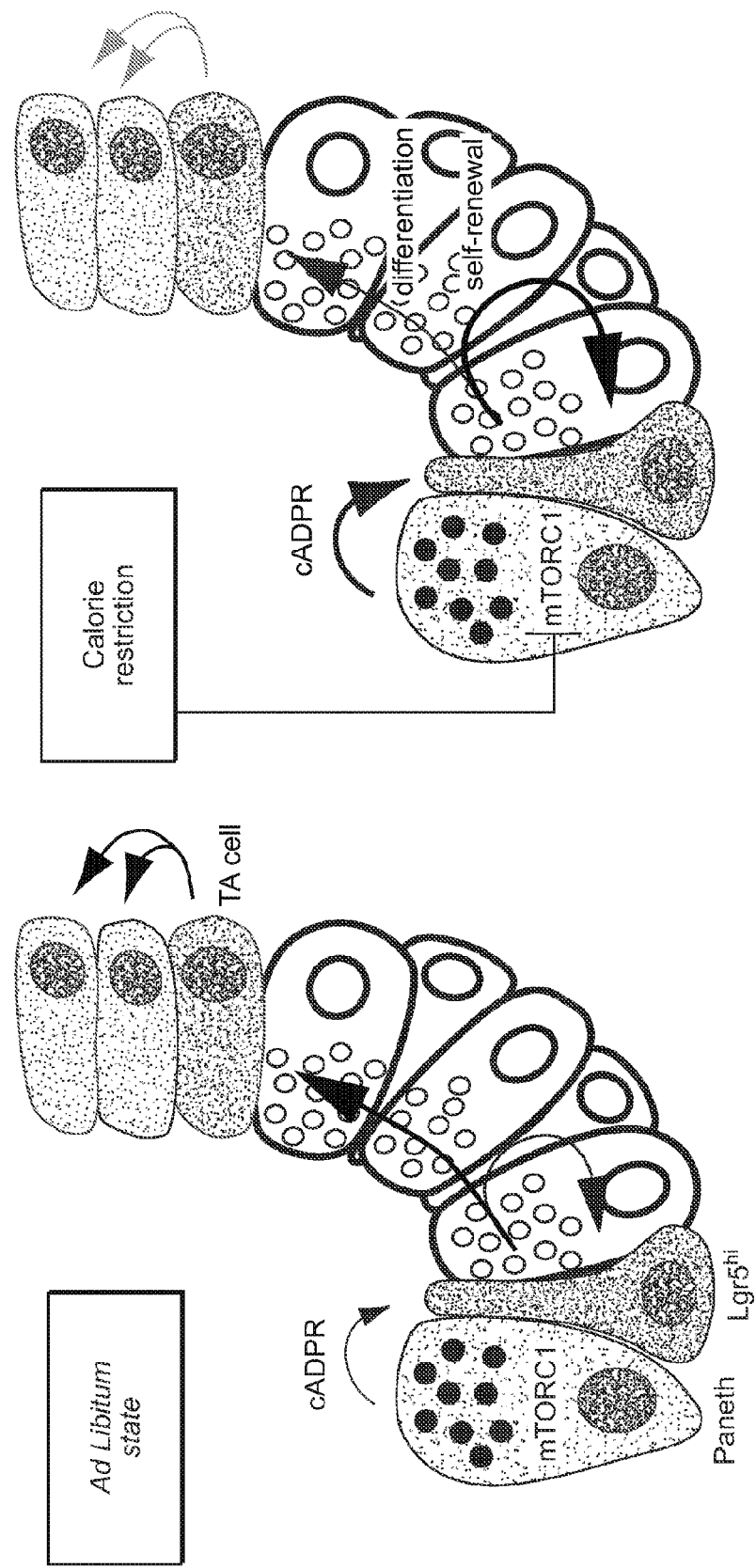

We chose to focus on bone stromal antigen 1 (Bst-1) as previous work shows that its expression in bone marrow stromal cells promotes the proliferation of hematopoietic progenitors[26]. Bst-1 is an ectoenzyme that converts NAD+ to cyclic ADP ribose (cADPR), a paracrine effector that enters responder cells via nucleoside transporters. Inside cells, cADPR activates calcium signaling and promotes proliferation. We validated that CR increased Bst-1 mRNA and protein expression in Paneth cells as well as caused a shift in its SDS-PAGE mobility, indicating CR-stimulated processing (FIG. 4b, FIG. 4c, FIG. 4d, and FIG. 4e). Interestingly, the addition of cADPR to crypt culture significantly improved the clonogenicity and size of AL-derived organoid bodies to a similar extent to those of CR-derived (FIG. 4e). We then asked whether Bst-1 was necessary to mediate many of the effects of CR in the organoid formation assay and whether depletion of Bst-1 abolished the enhanced function of CR crypts (FIG. 4f and FIG. 4g). Indeed, knockdown of Bst-1 mRNA with 2 independent siRNAs abrogated the increase in CR crypt clonogenicity, and the addition of cADPR was sufficient to rescue the function of these crypts. Lastly, the addition of dipyridamole, a compound that blocks nucleoside transporters and prevents cADPR from entering cells, reduced the clonogenicity of CR and AL-derived crypts to same level, suggesting that cADPR not only mediates the enhanced function of CR-derived crypts but is also important for the baseline activity of AL-derived crypts (FIG. 4h). These data demonstrate that CR, in an mTORC1-dependent manner, increases the expression in Paneth cells of Bst-1, whose paracrine product cADPR enhances ISC function.

Our data support the idea that the mammalian intestinal stem cell niche couples organismal nutritional status to stem cell function, allowing for dynamic tissue remodeling. Reduced calorie intake for just a few weeks leads to more ISC self-renewal (expansion of phenotypic ISCs in vivo), an accompanying increase in the ISC niche, and to an increase in ISC function and regeneration in vivo and in vitro. Although it is unclear why CR increases ISC numbers and function, one possibility is that in low calorie conditions it may be advantageous for ISCs to slightly shift the balance towards self-renewal while reducing the pool (EGFP$^{low}$) and proliferation of more differentiated TA-cells. Preserving or increasing the stem cell pool may better prepare the intestine for rapid regeneration once nutrients become abundant.

CR mediates many of its effects on ISCs by reducing mTORC1 signaling in the ISC niche, emphasizing the importance of non-cell autonomous mechanisms in intestinal adaptation and regeneration. Moreover, our data raise the intriguing possibility that the use mTORC1 inhibitors or Bst-1 mimetics, such as FDA-approved drugs like rapamycin or cADPR, may play a role in improving intestinal regeneration and function in patients.

Experimental Procedures Used in the Examples
Materials and Method
Mice and Short-Term Calorie Restriction Mice were housed in the Unit for Laboratory Animal Medicine at the Whitehead Institute for Biomedical Research. Lgr5-EGFP-IRES-CreERT2 mice (Strain name: B6.129P2-Lgr5tm1(cre/ERT2)Cle/J, Stock Number: 008875) were purchased from Jackson Laboratories. UbiquitinC-CreERT2 mice were obtained from the Jackson Laboratory (Strain Name: B6; 129S-Tg(UBC-cre/ERT2)1Ejb/J, Stock Number: 007001). Rictor floxed mice were generated as described in[27] and backcrossed to C57BL/6 for at least 6 generations. TSC1$^{loxp/loxp}$ mice were the generous gift of D. Kwiatkowski (Harvard Medical School) and backcrossed to C57BL/6 for at least 6 generations. Rosa26-CreERT2 mice (Rosa26 or R26) were obtained from the Jackson Laboratory (Strain 15 Name: B6.129-Gt(ROSA)26Sor$^{tm1(cre/ERT2)Tyj}$/J, Stock Number 008463). CR was achieved by providing individual or paired mice a daily portion of a chow diet fortified with vitamins and minerals amounting to 60% of the daily food intake of their ad libitum counterparts[20]. All adult mice used in CR experiments were between the ages of 10 to 24 weeks and were sacrificed prior to their daily feeding. Rictor or TSC1 was excised by treatment with tamoxifen suspended in corn or sunflower seed oil (Spectrum) at a concentration of 10 mg/mL, and 200 µl per 25 g of body weight was injected intraperitoneally into mice once daily for 5-7 days. Control animals received an equal volume of the tamoxifen suspension, but did not express the CreERT2 fusion protein. Mice were allowed to recover for at least 7 days after the last tamoxifen injection prior to any experiments. In vivo fate mapping in Lgr5-EGFP-IRES-reERT2; Rosa26loxpstoploxp-LacZ compound mice was done with a single injection of tamoxifen given at 200 µl per 25 g. As described previously[28], Rapamycin (LC Laboratories) was administered by intraperitoneal injection for 7 to 28 consecutive doses at 4 mg/kg. It was reconstituted in absolute ethanol at 10 mg/ml and diluted in 5% Tween-80 (Sigma) and 5% PEG-400 (Hampton Research) before injection. The final volume of all injections was 200 µl. Regular insulin (Lilly) was administered at 0.75 U/kg diluted in PBS 20 minutes prior to sacrificing fasted mice.

Generation of Rheb2 Transgenic Mouse

The Rheb2 transgenic mouse was produced as described before in[29]. Briefly, mouse embryonic stem cells (KH2) were obtained containing a neomycin resistance gene as well as a hygromycin resistance gene lacking a promoter and an ATG start codon at the 16 ColA1 locus. The presence of frt sites flanking the neomycin and hygromycin resistant genes allows site-specific integration of the transgene at the ColA1 locus. These embryonic cells also contain a M2rtTA transactivator at the endogenous Rosa26 promoter which, in the presence of doxycycline, leads to the transactivation of tetOpromoter driven transgenes. The human Rheb2 (hsRheb2) coding sequence was cloned into a vector downstream of a tetO promoter that also contained a PKG-ATG-frt element necessary for frt-site integration. This vector, along with another vector contained the FLPe recombinase, were then electroporated into the KH2 cells. As a result, the coding sequence for hsRheb2 along with a PGK promoter and the ATG initiation codon necessary for the expression of the hygromycin resistance gene is integrated into the genomic DNA of the KH2 cells at the ColA1 locus. Cells with properly integrated hsRheb2 were then selected by hygromycin resistance and subsequently injected into blastocysts. Chimeric mice were then mated with C57BL/6J mice until germline transmission of the transgene was achieved. PCR genotyping of the hsRheb2 transgenic mouse was performed with the following primers: Rheb-tg_F: CCAATTTGTGGAAGGCGAGTT (SEQ ID NO. 1), Rheb2-TG_R:CCATGGCCTTCATGTAGCTT (SEQ ID NO.2).

Immunohistochemistry/Fluorescence

Tissues were fixed in 10% formalin, paraffin embedded, and sectioned. Antigen retrieval was performed with Borg Decloaker RTU solution (Biocare Medical) in a pressurized Decloaking Chamber (Biocare Medical) for 3 minutes. Antibodies: rat anti-BrdU (1:2000; Abeam 6326), rabbit phospho-S6 Ser235/236 (1:500, CST 4858), rabbit cleaved caspase 3 (1:500; CST 9664), rabbit chromogranin A (1:3000, Abeam 15160), rabbit Lysozyme (1:2000; Thermo), rabbit Bst-1 (1:1000, Abeam 74301) and mouse Bst-1 (1:100 to 500, BD Pharmingen). For mouse Bst-1, the M.O.M (mouse on mouse) kit was used according to the manufacturer's instructions (Vector labs PK-2200). Biotin conjugated secondary donkey anti-rabbit or rat antibodies were used from Jackson ImmunoResearch. The Vectastain Elite ABC immunoperoxidase detection kit (Vector Labs PK-6101) followed by Dako Liquid DAB+ Substrate (Dako) was used for visualization. For immunofluorescence Alexa Fluor 568 secondary antibodies (Invitrogen) were used. All antibody incubations were performed with Common Antibody Diluent (Biogenex).

In Situ Hybridization

The in situ probes used in this study correspond to expressed sequence tags or fully sequenced cDNAs obtained from Open Biosystems. The accession numbers (IMAGE mouse cDNA clone in parenthesis) for these probes are as follow: mouse OLFM4 BC141127 (9055739), mouse crypt-din4 BC134360 (40134597). To ensure the specificity of the probes, we generated both sense and antisense probes by in vitro transcription using DIG RNA labelling mix (Roche) according to the manufacturer's instructions and to previously published detailed methods[21,30].

Immunoblotting

Antibodies: rabbit anti phospho-T389 S6K1, phospho-S240/244 S6, S6K1, and S6 from CST; rabbit Bst-1 (ab74301) from Abeam; mouse anti_-actin (clone AC-15) from Sigma. Crypts or tissue were rinsed once with ice-cold PBS and lysed in ice-cold lysis buffer (50 mM HEPES [pH 7.4], 40 rnM NaCl, 2 mM EDTA, 1.5 mM sodium orthovanadate, 50 mM NaF, 10 mM pyrophosphate, 10 mM glycerophosphate, and 1% Triton X-100, and one tablet of EDTA-free protease inhibitors [Roche] per 25 ml). The soluble fractions of cell lysates were isolated by centrifugation at 13,000 rpm for 10 min. Proteins extracts were denatured by the addition of sample buffer, boiled for 5 mM, resolved by SDS-PAGE, and analyzed by immunoblotting.

Flow Cytometry and Isolation of ISCs and Paneth Cells

Small intestines were removed and the fat/mesentery was dissected away. The intestinal lumen was washed with ice cold PBS (Mg—/Ca—) using a 18 G feeding needle (Roboz FN-7905) until the intestines appeared white/pink. They were then opened longitudinally. The mucous was removed by gently rubbing the intestine between fingers in cold PBS. The intestines were cut into 3 to 5 mm fragments and placed into 50 ml conical tubes that were fill with ice cold 30 ml of PBS (Mg—/Ca—)/EDTA (10 mM). The samples were incubated and shook intermittently on ice for 30 minutes continuously discarding and replacing (at least 3 times) the supernatant. The fragments were then continually resuspended with ice cold 30 ml PBS (Mg—/Ca—)/EDTA (10 mM) and intermittently shook on ice for 10 minutes, discarding the supernatant again for 3 times. The fragments were resuspended again with ice cold 30 ml PBS (Mg—/Ca—)/EDTA (10 mM) and incubated and intermittently shook while waiting on ice for 20 to 40 minutes. The samples were then triturated with a 10 ml pipette 1 to 2 times, and the contents were filtered twice through a 70-µm mesh (BD Falcon) into a 50 ml conical tube to remove villous material and tissue fragments. At this point the suspension was mainly composed of crypts. Crypts were removed from this step for crypt culture experiments and embedded in matrigel with crypt culture media. For ISC isolation, the crypt suspensions were centrifuged for 5 minutes at 250 g (4 C or room temperature). The pellets were gently resuspended in 1.0 ml of undiluted TrypLE Express (Invitrogen)+120 µl of DNase I (10 U/µl, Roche) and transferred to 15 ml conical tubes. The samples were incubated in a 32° C. water bath for 1.25 to 2 minutes, were not titurated, and were then placed on ice. 12 ml of cold SMEM was added to each sample and were gently triturated twice. The samples were then centrifuged for 5 minutes at 250 g. The pellets were resuspended and incubated for 15 minutes on ice in 0.5 to 1 ml SMEM that contained an antibody cocktail consisting of CD45-PE (eBioscience, 30-F11), CD31-PE (Biolegend, Mec13.3), Ter119-PE (Biolegend, Ter119), CD24-Pacific Blue (Biolegend, M1/69) and EPCAM-APC (eBioscience, G8.8). 12 ml of SMEM were added and the samples were centrifuged for 5 minutes at 250 g. The pellets were resuspended with 0.5-2 ml (depending on the size of the pellet) of SMEM/7-AAD solution (1:500 dilution).

The samples were filtered through a 40-µm mesh (BD Falcon) prior to cell sorting. ISCs were isolated as Lgr5-EGFPhiEpcam+CD24low/-CD31-Ter119-CD45-7-AAD- and Paneth cells were isolated as CD24hiSideScatterhiLgr5-EGFP-Epcam+CD31-Ter119-CD45-7-AAD- with a BD FACS Aria II SORP cell sorter into supplemented crypt culture medium.

When indicated, populations were cytospun (Thermo Cytospin 4) at 800 rpm for 2 min, or allowed to settle at 37° C. in fully humidified chambers containing 6% CO2 onto poly-L-lysine coated slides (Polysciences). The cells were subsequently fixed in 4% paraformaldehyde (pH=7.4, Electron Microscopy Sciences) prior to staining.

Crypt Culture Media

Isolated crypts were counted and embedded in matrigel (BD Bioscience 356231 growth factor reduced) that contains 1 µM Jagged (Ana-Spec) at 5-10 crypts/µl and cultured in a modified form of medium as described in[3]. Briefly, DMEM/F12 (Gibco) was supplemented by EGF 40 ng/ml (R&D), Noggin 200 ng/ml (Peprotech), R-spondin 500 ng/ml (R&D or Sino Biological), N-Acetyl-L-cysteine 1 µM (Sigma-Aldrich) and Y-27632 dihydrochloride monohydrate 20 ng/ml (Sigma-Aldrich). cADPR (Sigma), when indicated, was added to culture at 50 µM. 30-50 µl drops of matrigel with crypts were plated onto a flat bottom 48-well plate (Corning 3548) and allowed to solidify for 20 to 30 minutes in a 37° C. incubator. 350 µl of crypt culture medium was then overlaid onto the matrigel, changed every other day, and maintained at 37° C. in fully humidified chambers containing 6% CO2.

Culture of Isolated Cells in Supplemented Crypt Culture Medium

Isolated ISCs or Paneth cells were centrifuged for 5 minutes at 250 g and then resuspended in the appropriate volume of crypt culture medium (500-1000 cells/µl) supplemented with 1×N2 (Invitrogen), 1×B27 (Invitrogen), 100 ng/ml Wnt-3A (R&D), and with additional 500 ng/ml R-Spondin to yield 1 µg/ml final concentration. ISCs were then seeded into matrigel (BD Bioscience 356231 growth factor reduced) containing 1 µM Jagged (Ana-Spec) up to 5,000-10,000 cells/30-50 µl. 30 µl drops of 65% matrigel were plated onto a flat bottom 48-well plate (Corning 3548) and then Paneth cells were added at the same cell count to the top of the matrigel drop. Alternatively, ISCs and Paneth cells were mixed after sorting in a 1:1 ratio, centrifuged, and then seeded into matrigel. The matrigel drops with ISCs and Paneth cells were allowed to solidify for 20 to 30 minutes in a 37° C. incubator. 350 µl of crypt culture medium was then overlayed onto the drops of matrigel and maintained at 37° C. in fully humidified chambers containing 6% CO2. The crypt media was changed every second day. Organoid bodies were quantitated on days 3, 7, and 9 days of culture, unless otherwise specified. In subcloning experiments, either individual or cultures of organoids were manually disrupted as indicated in the text on day 7-9 by rigorous tituration and replated into fresh matrigel; these secondary organoid bodies were quantitated on day 18 after initiation of the primary cultures. When indicated, crypts were transfected with 100 nM siRNAs targeting the Bst-1 (Thermo Scientific, J-044021-11 and J-044021-12) using the XTremegene siRNA transfection reagent, by incubating the crypts at +37° C. for 30 min with transfection mixture in crypt medium before mounting to matrigel.

Microarray Analysis and Validation

Approximately 100,000 Paneth cells were harvested directly to the RLT buffer of the RNeasy plus extraction kit (Qiagen) by the flowcytometry isolation protocol. Total RNA extracts were subjected to microarray analysis by standard protocols of the Whitehead Institute Genome Technology Core (http://jura.wi.mit.edu/genomecorewiki/index.php/Main_Page) using GeneChip Mouse Gene 1.0 ST arrays (Affymetrix). Expression analysis was conducted with the help of Whitehead Institute Bioinformatics and Research Computing. Shortly, CEL-files were preprocessed with RMA using Bioconductor and the package oligo, and differential expression was assayed by moderated t-test, as implemented by limma. Expression changes were validated by qRT-PCR using oligos:

```
                                             (SEQ ID NO. 3)
     Bst-1 ACCCCATTCCTAGGGACAAG, (SEQ ID NO. 4)
     GCCTCCAATCTGTCTTCCAG, (SEQ ID NO. 5)
     Wnt3a GGGAGAAATGCCACTGTGTT, (SEQ ID NO. 6)
     TCTCCGCCCTCAAGTAAGAA, (SEQ ID NO. 7)
     Myc TCTCCACTCACCAGCACAAC, (SEQ ID NO. 8)
     TCGTCTGCTTGAATGGACAG, (SEQ ID NO. 9)
     Gapdh TGTTCCTACCCCAATGTGT, (SEQ ID NO. 10)
     TGTGAGGGAGATGCTCAGTG.
```

Electron Microscopy

Immediately after removal from the animal, 1.0 mm sections of mouse intestine were placed into Karnovsky's KII Solution (2.5% glutaraldehyde, 2.0% paraformaldehyde, 0.025% calcium chloride, in a 0.1 M sodium cacodylate buffer, pH 7.4), fixed overnight at 4° C., and stored in cold buffer. Subsequently, they were post-fixed in 2.0% osmium tetroxide, stained en bloc with uranyl acetate, dehydrated in graded ethanol solutions, infiltrated with propylene oxide/Epon mixtures, flat embedded in pure Epon, and polymerized over night at 60° C. One micron sections were cut, stained with toluidine blue, and examined by light microscopy. Representative areas were chosen for electron microscopic study and the Epon blocks were trimmed accordingly. Thin sections were cut with an LKB 8801 ultramicrotome and diamond knife, stained with Sato's lead, and examined in a FEI Morgagni transmission electron microscope. Images were captured with an AMT (Advanced Microscopy Techniques) 2K digital CCD camera.

REFERENCES

1. Simons, B. D. & Clevers, H. Strategies for homeostatic stem cell self-renewal in adult tissues. *Cell* 145, 851-862 (2011).
2. Nakada, D., Levi, B. P. & Morrison, S. J. Integrating physiological regulation with stem cell and tissue homeostasis. *Neuron* 70, 703-718 (2011).

3. Sato, T. et al. Paneth cells constitute the niche for Lgr5 stem cells in intestinal crypts. *Nature* 469, 415-418 (2010).
4. O'Brien, L. E., Soliman, S. S., Li, X. & Bilder, D. Altered modes of stem cell division drive adaptive intestinal growth. *Cell* 147, 603-614 (2011).
5. McCay, C. M., Maynard, L. A., Sperling, G. & Barnes, L. L. The Journal of Nutrition. Volume 18 July-December, 1939. Pages 1-13. Retarded growth, life span, ultimate body size and age changes in the albino rat after feeding diets restricted in calories. *Nutr Rev* 33, 241-243 (1975).
6. Bondolfi, L., Ermini, F., Long, J. M., Ingram, D. K. & Jucker, M. Impact of age and caloric restriction on neurogenesis in the dentate gyrus of C57BL/6 mice. *Neurobiol Aging* 25, 333-340 (2004).
7. Ertl, R. P., Chen, J., Astle, C. M., Duffy, T. M. & Harrison, D. E. Effects of dietary restriction on hematopoietic stem-cell aging are genetically regulated. *Blood* 111, 1709-1716 (2008).
8. Chen, J., Astle, C. M. & Harrison, D. E. Hematopoietic senescence is postponed and hematopoietic stem cell function is enhanced by dietary restriction. *Exp Hematol* 31, 1097-1103 (2003).
9. Yilmaz, O. H., Kiel, M. J. & Morrison, S. J. SLAM family markers are conserved among hematopoietic stem cells from old and reconstituted mice and markedly increase their purity. *Blood* 107, 924-930 (2006).
10. Dunel-Erb, S. et al. Restoration of the jejunal mucosa in rats refed after prolonged fasting. *Comp Biochem Physiol A Mol Integr Physiol* 129, 933-947 (2001).
11. Altmann, G. G. Influence of starvation and refeeding on mucosal size and epithelial renewal in the rat small intestine. *The American journal of anatomy* 133, 391-400 (1972).
12. Zhu, L. et al. Prominin 1 marks intestinal stem cells that are susceptible to neoplastic transformation. *Nature* 457, 603-607 (2009).
13. Sangiorgi, E. & Capecchi, M. R. Bmi1 is expressed in vivo in intestinal stem cells. *Nat Genet* 40, 915-920 (2008).
14. Breault, D. T. et al. Generation of mTert-GFP mice as a model to identify and study tissue progenitor cells. *Proc Natl Acad Sci USA* 105, 10420-10425 (2008).
15. Barker, N. et al. Identification of stem cells in small intestine and colon by marker gene Lgr5. *Nature* 449, 1003-1007 (2007).
16. Takeda, N. et al. Interconversion between intestinal stem cell populations in distinct niches. *Science* 334, 1420-1424 (2011).
17. Snippert, H. J. et al, Intestinal crypt homeostasis results from neutral competition between symmetrically dividing Lgr5 stem cells. *Cell* 143, 134-144 (2010).
18. Hempenstall, S., Picchio, L., Mitchell, S. E., Speakman, J. R. & Selman, C. The impact of acute caloric restriction on the metabolic phenotype in male C57BL/6 and DBA/2 mice. *Mech Ageing Dev* 131, 111-118 (2010).
19. Cohen, D. E., Supinski, A. M., Bonkowski, M. S., Donmez, G. & Guarente, L. P. Neuronal SIRT1 regulates endocrine and behavioral responses to calorie restriction. *Genes Dev* 23, 2812-2817 (2009).
20. Kalaany, N. Y. & Sabatini, D. M. Tumours with PI3K activation are resistant to dietary restriction. *Nature* 458, 725-731 (2009).
21. van der Flier, L. G. et al. Transcription factor achaete scute-like 2 controls intestinal stem cell fate. *Cell* 136, 903-912 (2009).
22. Sato, T. et al. Single Lgr5 stem cells build crypt-villus structures in vitro without a mesenchymal niche. *Nature* 459, 262-265 (2009).
23. Marsh, V. et al. Epithelial Pten is dispensable for intestinal homeostasis but suppresses adenoma development and progression after Apc mutation. *Nat Genet* 40, 1436-1444 (2008).)
24. Sengupta, S., Peterson, T. R., Laplante, M., Oh, S. & Sabatini, D. M. mTORC1 controls fasting-induced ketogenesis and its modulation by ageing. *Nature* 468, 1100-1104 (2010).
25. Sarbassov, D. D. et al. Prolonged rapamycin treatment inhibits mTORC2 assembly and Akt/PKB. *Mol Cell* 22, 159-168 (2006).
26. Podesta, M. et al. Concentrative uptake of cyclic ADP-ribose generated by BST-1+ stroma stimulates proliferation of human hematopoietic progenitors. *The Journal of biological chemistry* 280, 5343-5349 (2005).
27. Guertin, D. A. et al. mTOR complex 2 is required for the development of prostate cancer induced by Pten loss in mice, *Cancer Cell* 15, 148-159 (2009).
28. Yilmaz, O. H. et al. Pten dependence distinguishes haematopoietic stem cells from leukaemia-initiating cells. *Nature* 441, 475-482 (2006).
29. Beard, C., Hochedlinger, K., Plath, K., Wutz, A. & Jaenisch, R. Efficient method to generate single-copy transgenic mice by site-specific integration in embryonic stem cells. *Genesis* 44, 23-28 (2006).
30. Gregorieff, A. & Clevers, H. In situ hybridization to identify gut stem cells. *Curr Protoc Stem Cell Biol* Chapter 2, Unit 2F 1.

What is claimed is:

1. A method of stimulating the proliferation and/or self-renewal of one or more intestinal stem cells in mammalian intestinal tissue comprising contacting a population of Paneth cells or Paneth-like cells in the mammalian intestinal tissue with an effective amount of a calorie restriction mimetic, wherein the calorie restriction mimetic comprises an agent that increases the level and/or activity of bone stromal antigen 1 (Bst-1) or a product of Bst-1.

2. A method according to claim 1 wherein the agent stimulates intracellular release of $Ca^{2+}$.

3. A method according to claim 1 wherein the agent induces the ryanodine receptor to release $Ca^{2+}$ into the cytosol.

4. A method according to claim 1 wherein the product of Bst-1 comprises cyclic ADP ribose.

5. A method according to claim 1 wherein the calorie restriction mimetic comprises cADPR.

6. A method according to claim 1, wherein the contacting occurs in vitro.

7. A method according to claim 1, wherein the contacting occurs in vivo.

* * * * *

SEQUENCE LISTING

```
<160> NUMBER OF SEQ ID NOS: 10

<210> SEQ ID NO 1
<211> LENGTH: 21
<212> TYPE: DNA
<213> ORGANISM: Artificial
<220> FEATURE:
<223> OTHER INFORMATION: primer

<400> SEQUENCE: 1
ccaatttgtg gaaggcgagt t                                          21

<210> SEQ ID NO 2
<211> LENGTH: 20
```

```
<212> TYPE: DNA
<213> ORGANISM: Artificial
<220> FEATURE:
<223> OTHER INFORMATION: primer

<400> SEQUENCE: 2
ccatggcctt catgtagctt                                               20

<210> SEQ ID NO 3
<211> LENGTH: 20
<212> TYPE: DNA
<213> ORGANISM: Artificial
<220> FEATURE:
<223> OTHER INFORMATION: qRT-PCR oligo

<400> SEQUENCE: 3
accccattcc tagggacaag                                               20

<210> SEQ ID NO 4
<211> LENGTH: 20
<212> TYPE: DNA
<213> ORGANISM: Artificial
<220> FEATURE:
<223> OTHER INFORMATION: qRT-PCR oligo

<400> SEQUENCE: 4
gcctccaatc tgtcttccag                                               20

<210> SEQ ID NO 5
<211> LENGTH: 20
<212> TYPE: DNA
<213> ORGANISM: Artificial
<220> FEATURE:
<223> OTHER INFORMATION: qRT-PCR oligo

<400> SEQUENCE: 5
gggagaaatg ccactgtgtt                                               20

<210> SEQ ID NO 6
<211> LENGTH: 20
<212> TYPE: DNA
<213> ORGANISM: Artificial
<220> FEATURE:
<223> OTHER INFORMATION: qRT-PCR oligo

<400> SEQUENCE: 6
tctccgccct caagtaagaa                                               20

<210> SEQ ID NO 7
<211> LENGTH: 20
<212> TYPE: DNA
<213> ORGANISM: Artificial
<220> FEATURE:
<223> OTHER INFORMATION: qRT-PCR oligo

<400> SEQUENCE: 7
tctccactca ccagcacaac                                               20

<210> SEQ ID NO 8
<211> LENGTH: 20
<212> TYPE: DNA
<213> ORGANISM: Artificial
<220> FEATURE:
<223> OTHER INFORMATION: qRT-PCR oligo

<400> SEQUENCE: 8
```

```
tcgtctgctt gaatggacag                                            20

<210> SEQ ID NO 9
<211> LENGTH: 20
<212> TYPE: DNA
<213> ORGANISM: Artificial
<220> FEATURE:
<223> OTHER INFORMATION: qRT-PCR oligo

<400> SEQUENCE: 9
tgttcctacc cccaatgtgt                                            20

<210> SEQ ID NO 10
<211> LENGTH: 20
<212> TYPE: DNA
<213> ORGANISM: Artificial
<220> FEATURE:
<223> OTHER INFORMATION: qRT-PCR oligo

<400> SEQUENCE: 10
tgtgagggag atgctcagtg                                            20
```